United States Patent
Quake et al.

(10) Patent No.: US 7,501,245 B2
(45) Date of Patent: Mar. 10, 2009

(54) METHODS AND APPARATUSES FOR ANALYZING POLYNUCLEOTIDE SEQUENCES

(75) Inventors: Stephen Quake, Stanford, CA (US); Emil Paskalev Kartalov, Pasadena, CA (US)

(73) Assignee: Helicos BioSciences Corp., Cambridge, MA (US)

( * ) Notice: Subject to any disclaimer, the term of this patent is extended or adjusted under 35 U.S.C. 154(b) by 764 days.

(21) Appl. No.: 11/002,479

(22) Filed: Dec. 1, 2004

(65) Prior Publication Data

US 2006/0019263 A1    Jan. 26, 2006

Related U.S. Application Data

(60) Continuation-in-part of application No. 09/908,830, filed on Jul. 18, 2001, now Pat. No. 6,911,345, which is a division of application No. 09/707,737, filed on Nov. 6, 2000, now Pat. No. 6,818,395, and a continuation-in-part of application No. 09/605,520, filed on Jun. 27, 2000.

(60) Provisional application No. 60/163,742, filed on Nov. 4, 1999, provisional application No. 60/141,503, filed on Jun. 28, 1999, provisional application No. 60/147,199, filed on Aug. 3, 1999, provisional application No. 60/186,856, filed on Mar. 3, 2000, provisional application No. 60/526,162, filed on Dec. 1, 2003.

(51) Int. Cl.
*C12Q 1/68* (2006.01)

(52) U.S. Cl. .............................. 435/6; 435/7.9

(58) Field of Classification Search ........................ None
See application file for complete search history.

(56) References Cited

U.S. PATENT DOCUMENTS

| | | | |
|---|---|---|---|
| 5,632,957 | A | 5/1997 | Heller et al. |
| 5,795,782 | A | 8/1998 | Church et al. |
| 6,015,714 | A | 1/2000 | Baldarelli et al. |
| 6,020,457 | A | 2/2000 | Klimash et al. |
| 6,077,674 | A | 6/2000 | Schleifer et al. |
| 6,355,420 | B1 | 3/2002 | Chao |
| 6,818,395 | B1 | 11/2004 | Quake et al. |
| 6,911,345 | B2 | 6/2005 | Quake et al. |
| 2002/0025529 | A1 | 2/2002 | Quake et al. |
| 2002/0164629 | A1 | 11/2002 | Quake et al. |

(Continued)

FOREIGN PATENT DOCUMENTS

EP    0223618 A2    5/1987

(Continued)

OTHER PUBLICATIONS

Kartalov et al. "Polyelectrolyte Surface Interface for Single-Molecule Fluorescence Studies of DNA Polymerase", Biotechniques, 2003, v. 24, No. 3, pp. 505-510.*

(Continued)

*Primary Examiner*—Yelena G Gakh
(74) *Attorney, Agent, or Firm*—Cooley Godward Kronish LLP; Thomas C. Meyers, Esq.; Konstantin M. Linnik, Esq.

(57) ABSTRACT

Methods for high speed, high throughput analysis of polynucleotide sequences, and apparatuses with which to carry out the methods are provided in the invention.

4 Claims, 22 Drawing Sheets

U.S. PATENT DOCUMENTS

| | | |
|---|---|---|
| 2003/0003272 A1 | 1/2003 | Laguitton |
| 2003/0008413 A1 | 1/2003 | Kim et al. |
| 2003/0044816 A1 | 3/2003 | Denison et al. |
| 2005/0014175 A1 | 1/2005 | Quake et al. |
| 2005/0147992 A1 | 7/2005 | Quake et al. |
| 2005/0170367 A1 | 8/2005 | Quake et al. |

FOREIGN PATENT DOCUMENTS

| | | |
|---|---|---|
| EP | 0579997 A1 | 1/1994 |
| EP | 0706004 A2 | 4/1996 |
| EP | 0779436 A2 | 6/1997 |
| EP | 0845603 A1 | 6/1998 |
| EP | 0932700 B1 | 8/1999 |
| EP | 0946752 B1 | 10/1999 |
| EP | 0955085 A2 | 11/1999 |
| EP | 0999055 A2 | 5/2000 |
| EP | 0706004 B1 | 8/2003 |
| GB | 2155152 A | 9/1985 |
| GB | 2308460 A | 6/1997 |
| GB | 2400518 A | 10/2004 |
| SE | 9500589 | 2/1995 |
| WO | 89/03432 A1 | 4/1989 |
| WO | 89/09283 A1 | 10/1989 |
| WO | 90/13666 A1 | 11/1990 |
| WO | 90/15070 A1 | 12/1990 |
| WO | 91/06678 A1 | 5/1991 |
| WO | 92/10092 A1 | 6/1992 |
| WO | 92/10587 A1 | 6/1992 |
| WO | 93/05183 A1 | 3/1993 |
| WO | 93/06121 A1 | 4/1993 |
| WO | 93/21340 A1 | 10/1993 |
| WO | 95/12608 A1 | 5/1995 |
| WO | 95/27080 A1 | 10/1995 |
| WO | 96/04547 A1 | 2/1996 |
| WO | 96/12014 A1 | 4/1996 |
| WO | 96/12039 A1 | 4/1996 |
| WO | 96/27025 A1 | 9/1996 |
| WO | 97/02488 A1 | 1/1997 |
| WO | 97/22076 A1 | 6/1997 |
| WO | 97/23650 A2 | 6/1997 |
| WO | 97/37041 A2 | 10/1997 |
| WO | 97/39150 A1 | 10/1997 |
| WO | 97/40184 A1 | 10/1997 |
| WO | 97/41258 A1 | 11/1997 |
| WO | 97/41259 A1 | 11/1997 |
| WO | 97/42348 A1 | 11/1997 |
| WO | 98/00708 A1 | 1/1998 |
| WO | 98/02575 A1 | 1/1998 |
| WO | 98/03684 A1 | 1/1998 |
| WO | 98/07069 A1 | 2/1998 |
| WO | 98/13523 A1 | 4/1998 |
| WO | 98/08978 A1 | 5/1998 |
| WO | 98/20019 A1 | 5/1998 |
| WO | 98/20020 A2 | 5/1998 |
| WO | 98/20166 A2 | 5/1998 |
| WO | 98/21361 A1 | 5/1998 |
| WO | 98/27228 A1 | 6/1998 |
| WO | 98/28440 A1 | 7/1998 |
| WO | 98/33939 A1 | 8/1998 |
| WO | 98/40520 A1 | 9/1998 |
| WO | 98/41650 A2 | 9/1998 |
| WO | 98/41657 A1 | 9/1998 |
| WO | 98/44152 A1 | 10/1998 |
| WO | 98/45481 A1 | 10/1998 |
| WO | 98/53300 A2 | 11/1998 |
| WO | 98/54669 A1 | 12/1998 |
| WO | 98/55593 A1 | 12/1998 |
| WO | 99/01768 A1 | 1/1999 |
| WO | 99/05221 A1 | 2/1999 |
| WO | 99/05315 A2 | 2/1999 |
| WO | 99/06422 A2 | 2/1999 |
| WO | 99/13109 A1 | 3/1999 |
| WO | 99/13110 A1 | 3/1999 |
| WO | 99/09616 A1 | 4/1999 |
| WO | 99/17093 A1 | 4/1999 |
| WO | 99/19516 A1 | 4/1999 |
| WO | 99/24797 A1 | 5/1999 |
| WO | 99/27137 A1 | 6/1999 |
| WO | 99/31278 A1 | 6/1999 |
| WO | 99/37810 A1 | 7/1999 |
| WO | 99/39001 A2 | 8/1999 |
| WO | 99/40105 A2 | 8/1999 |
| WO | 99/40223 A1 | 8/1999 |
| WO | 99/41410 A1 | 8/1999 |
| WO | 00/30591 A1 | 9/1999 |
| WO | 99/44045 A2 | 9/1999 |
| WO | 99/45153 A2 | 9/1999 |
| WO | 99/47539 A1 | 9/1999 |
| WO | 99/47706 A1 | 9/1999 |
| WO | 99/53423 A1 | 10/1999 |
| WO | 99/57321 A1 | 11/1999 |
| WO | 99/61888 A2 | 12/1999 |
| WO | 99/64437 A1 | 12/1999 |
| WO | 99/64840 A1 | 12/1999 |
| WO | 99/65938 A2 | 12/1999 |
| WO | 99/66076 A1 | 12/1999 |
| WO | 99/66313 A1 | 12/1999 |
| WO | 00/00637 A2 | 1/2000 |
| WO | 00/06770 A1 | 2/2000 |
| WO | 00/09753 A1 | 2/2000 |
| WO | 00/11223 A1 | 3/2000 |
| WO | 00/17397 A1 | 3/2000 |
| WO | 00/26935 A2 | 5/2000 |
| WO | 00/34523 A1 | 6/2000 |
| WO | 00/37680 A1 | 6/2000 |
| WO | 00/40750 A1 | 7/2000 |
| WO | 00/40758 A2 | 7/2000 |
| WO | 00/42223 A1 | 7/2000 |
| WO | 00/43540 A1 | 7/2000 |
| WO | 00/43752 A1 | 7/2000 |
| WO | 00/50642 A1 | 8/2000 |
| WO | 00/53805 A1 | 9/2000 |
| WO | 00/53812 A2 | 9/2000 |
| WO | 00/56937 A2 | 9/2000 |
| WO | 00/58507 A1 | 10/2000 |
| WO | 00/58516 A2 | 10/2000 |
| WO | 00/68410 A1 | 11/2000 |
| WO | 00/70073 A1 | 11/2000 |
| WO | 00/71755 A2 | 11/2000 |
| WO | 00/79007 A1 | 12/2000 |
| WO | 01/01025 A3 | 1/2001 |
| WO | 01/16375 A2 | 3/2001 |
| WO | 01/23610 A2 | 4/2001 |
| WO | 01/24937 A2 | 4/2001 |
| WO | 01/25480 A2 | 4/2001 |
| WO | 01/31055 A2 | 5/2001 |
| WO | 01/32930 A1 | 5/2001 |
| WO | 01/38574 A1 | 5/2001 |
| WO | 01/48184 A2 | 5/2001 |
| WO | 01/42496 A2 | 6/2001 |
| WO | 01/57248 A2 | 8/2001 |
| WO | 01/57249 A1 | 8/2001 |
| WO | 01/61044 A1 | 8/2001 |
| WO | 01/64838 A2 | 9/2001 |
| WO | 01/75154 A2 | 10/2001 |
| WO | 01/79536 A1 | 10/2001 |
| WO | 01/85991 A2 | 11/2001 |
| WO | 01/92284 A1 | 12/2001 |
| WO | 01/96607 A2 | 12/2001 |
| WO | 02/00343 A2 | 1/2002 |
| WO | 02/02584 A1 | 1/2002 |
| WO | 02/02795 A2 | 1/2002 |
| WO | 02/02813 A2 | 1/2002 |

| | | |
|---|---|---|
| WO | 02/03305 A2 | 1/2002 |
| WO | 02/04680 A2 | 1/2002 |
| WO | 02/20836 A2 | 3/2002 |
| WO | 02/20837 A2 | 3/2002 |
| WO | 02/27032 A1 | 4/2002 |
| WO | 02/29106 A2 | 4/2002 |
| WO | 02/30486 A3 | 4/2002 |
| WO | 02/35441 A2 | 5/2002 |
| WO | 02/36832 A2 | 5/2002 |
| WO | 02/44414 A2 | 6/2002 |
| WO | 02/061126 A2 | 8/2002 |
| WO | 02/061127 A2 | 8/2002 |
| WO | 02/072779 A2 | 9/2002 |
| WO | 02/072892 A1 | 9/2002 |
| WO | 02/077694 A1 | 10/2002 |
| WO | 02/079519 A1 | 10/2002 |
| WO | 02/088381 A2 | 11/2002 |
| WO | 02/088382 A2 | 11/2002 |
| WO | 02/097113 A2 | 12/2002 |
| WO | 02/099398 A1 | 12/2002 |
| WO | 03/002767 A1 | 1/2003 |
| WO | 03/016565 A2 | 2/2003 |
| WO | 03/020895 A2 | 3/2003 |
| WO | 03/020968 A2 | 3/2003 |
| WO | 03/021010 A2 | 3/2003 |
| WO | 03/031947 A2 | 4/2003 |
| WO | 03/044678 A1 | 5/2003 |
| WO | 03/048178 A2 | 6/2003 |
| WO | 03/048991 A2 | 6/2003 |
| WO | 03/062897 A1 | 7/2003 |
| WO | 03/106642 A2 | 12/2003 |
| WO | 2004/061119 A2 | 7/2004 |
| WO | 2004/074503 A2 | 9/2004 |
| WO | 2005/047523 A2 | 5/2005 |
| WO | WO-2005/054441 A2 | 6/2005 |
| WO | 2005/080605 A2 | 9/2005 |

OTHER PUBLICATIONS

Adam et al., "Individual genomes targeted in sequencing revolution", Nature, vol. 411, p. 402 (May 2001).
Agrawal, S. et al., "Site Specific Functionalization of Oligodeoxynucleotides for Non-Radioactive Labelling", Tetrahedron Letters, vol. 31, No. 11, pp. 1543-1546 (1990).
Ambrose, W. et al., "Single Molecule Detection With Total Internal Reflection Excitation: Comparing Signal-to-Background and Total Signals in Different Geometries", Cytometry, vol. 36, pp. 224-231 (1999).
Amit, B. et al., "Photosensitive Protecting Groups of Amino Sugars and Their Use in Glycoside Synthesis . . . Derivatives", 1. Org. Chem., 39(2):192-6 (1974).
Arndt-Jovin, D. et al., "Immunofluorescence Localization of Z-DNA in Chromosomes: Quantitation by Scanning Microphotometry and Computer-assisted Image Analysis", 1. The Journal of Cell Biology, vol. 101, pp. 1422-1433, (Oct. 1985).
Augustin, M.A., W. Ankenbauer, and B. Angerer, "Progress towards single-molecule sequencing: enzymatic synthesis of nucleotide-specifically labeled DNA." Journal of Biotechnology, 8(13): 289-301 (2001).
Axelrod, D., "Cell-Substrate Contacts Illuminated by Total Internal Reflection Fluorescence", 1. The Journal of Cell Biology, vol. 89, pp. 141-145, (Apr. 1981).
Axelrod, D. et al., "Total internal reflection fluorescent microscopy", J Microscopy, vol. 129, pp. 19-28, (1983).
Bai, X., et al., "Photocleavage of a 2-nitrobenzyl linker bridging a fluorophore to the 5' end of DNA." Proc Natl Acad Sci USA, 2003, vol. 100(2). p. 409-13.
Basche, T. et al., "Single Molecule Optical Detection, Imaging and Spectroscopy", Chs. 2 and 3, Weinheim:VCM, Germany (1997).
Beaucage, S. et al., "Advances in the Synthesis of Oligonucleotides by the Phosphoramidite Approach" Tetrahedron, 48:2223-2311 (1992).

Beese, L. et al., "Structure of DNA Polymerase I Klenow Fragment Bound to Duplex DNA", Science, 260:352-355 (1993).
Bennett et. al., "Solexa Sequencing chemistry can be applied to different platforms which will have common elements in detection and data processing", Pharmacogenomics 5(4), pp. 433-438, (2004).
Biesalski et al., "Preparation and Characterization of a Polyelectrolyte Monolayer Covalently Attached to a Planar Solid Surface", Macromolecules 111, 32, 2309-2316. Article was published on the web Mar. 10, 1999.
Black, D.L., "Protein diversity from alternating splicing: A challenge for bioinformatics and post genome biology", Cell, 2000. 103(3): p. 367-370.
Blattner, F.R., et al., "The Complete genome sequence of Escherichia coli K-12.", Science, 277: 1453-74 (1997).
Boles et. al., "High-Resolution Mapping of Carcinogen Binding Sites on DNA", Biochemistry, 1986, 25, 3039-3043.
Brakmann, S. and P. Nieckchen, "The large fragment of Escherichia coli DNA polymerase I can synthesize DNA exclusively from fluorescently labeled nucleotides." Chembiochem, 2(10): 773-777 (2001).
Brakmann et. al, "Optimal Enzymes for Single-Molecule Sequencing", Current Pharmaceutical Biotechnology, 5, pp. 119-126 (2004).
Braslavsky, I. et al., "Sequence information can be obtained from single DNA molecules", PNAS, vol. 100, No. 7, pp. 3960-3964 (Apr. 2003).
Braslavsky, I. et al., "Objective-type dark-field illumination for scattering from microbeads", Applied Optics, vol. 40, No. 31, pp. 5650-5657, (Nov. 2001).
Braslavsky, I. et al., "Single Molecule Measurements of DNA Polymerase Activity: A Step Towards Single Molecule Sequencing", Biophys. 1. Abstracts, p. 507A (2002).
Brechtel, R. et al., "Control of the electro osmotic flow by metal-salt-containing buffers", J Chromatoraphy A, vol. 716, pp. 97-105, (1995).
Bridgman, A. et al., "An improved method for the synthesis of mercurated dUTP. Enzymatic synthesis of Hg-labelled DNA of high molecular weight suitable for use in an image based DNA sequencing strategy", DNA Seq., vol. 6, No. 4, pp. 199-209 (1996).
Bruggert, J. et al., "Microfabricated tools for nanoscience", J. Micromech. Microeng., 3, pp. 161-167 (1993).
Bryzek, J. etal., "Micromachines on the march", IEEE Spectrum, vol. 31, No. 5, pp. 20-31, (1994).
Buchaillot, L. et al., "Silicon Nitride Thin Films Young's Modulus Determination by an Optical Non Destructive Method", Jpn. J. Appl. Phys., vol. 36, pp. L794-L797, (Jun. 1997).
Burghardt, T. et al., "Total Internal Reflection Fluorescence Study of Energy Transfer in Surface-Adsorbed and Dissolved Bovine Serum Albumin", Biochemistry, vol. 22, pp. 979-985 (1983).
Burghardt, et al., "Total Internal Reflection/Fluorescence Photobleaching Recovery Study of Serum Albumin Adsorption Dynamics", Biophys. Journal, vol. 33, pp. 455-468 (Mar. 1981).
Butler, D. et al., "Draft data leave geneticists with a mountain still to climb", Nature, vol. 405, Issue 6782, pp. 984-985 (May 2000).
Canard, B., B. Cardona, .and R.S. Sarfati, "Catalytic editing properties of DNA polymerases," Proc Natl Acad Sci USA, 92(24): p. 10859-63 (1995).
Canard, et al., "DNA polymerase fluorescent substrates with reversible 3'-tags", Gene, 148(1): 1-6 (1994).
Cheng et al., "High-speed DNA sequence analysis," Prog. in Biochem. and Biophys., vol. 22, pp. 223-227 (1995).
Chicurel, M., "Faster, better, cheaper genotyping", Nature, vol. 412, Issue 6847, pp. 580-582, (Aug. 2001).
Chidgeavadze et al., 2',3'-Dideoxy-3' aminonucleoside 5'-triphosphates are the terminators of DNA synthesis catalyzed by DNA polymerases, Nuc. Acids Res., 12(3):1671-1686 (1984).
Chidgeavadze, Z. et al., "3'-Fluro-2',3'-dideoxyribonucleoside 5'-triphosphates: terminators of DNA synthesis", FEBS Letters, 183(2):275-278 (1985).
Chiu, D. et al., "Patterned deposition of cells and proteins onto surfaces by using three-dimensional microfluidic systems," PNAS, vol. 97, No. 6, pp. 2408-2413 (2000).

Chou et al., "A microfabricated device for sizing and sorting DNA molecules", Applied Sciences, Biophysics: Proc. Natl. Acad. Sci. USA 96, pp. 11-13 (1999).

Chou et al., "A Microfabricated Rotary Pump", Biomedical Microdevices. vol. 3: p. 323-330 (2001).

Close, D. et al., "Ultraviolet Photobleaching of Free Radicals Created in y-Irradiated Amino Acids", *Radiation Research*, vol. 53, pp. 349-357 (1973).

Cooper, J. et al., "Analysis of Fluorescence Energy Transfer in Duplex and Branched DNA Molecules", *Biochemistry*, vol. 29, pp. 9261-9268 (1990).

Crocker, J.C. and D.G. Grier, "Methods of digital video microscopy for colloidal studies." *Journal of Colloid and Interface Science*, 179(1): p. 298-310 (1996).

Dapprich, J., "Single-molecule DNA digestion by lambda-exonuclease." *Cytometry*, 36(3): p. 163-168 (1999).

Debenham, J.S., et al., "Two New Orthogonal Amine-Protecting Groups that can be Cleaved under Mild or Neutral Conditions." *Journal of the American Chemical Society*, 117(11): p. 3302-3 (1995).

Decher, G. et al. "Buildup of ultrathin multiplayer films by a self-assembly process: III. Consecutively alternating absorption of anionic and cationic polyelectrolytes on charged surfaces", *Thin Solid Films*, 210:831-835 (1992).

Decher G.;et al., "Fuzzy nanoassemblies : Toward layered polymeric multicomposites." *Science*, 277(5330): p. 1232-1237 (1997).

Delamarche, E. et al., "Patterned Delivery of Immunoglobulins to Surfaces Using Microfluidic Networks", *Science* 276:779-781 (1997).

Dickson et al., "Simultaneous Imaging of Individual Molecules aligned both parallel and perpendicular to the optic axis", *The American Physical Society*, vol. 81, No. 24, pp. 5322-5325 (1998).

Doktycz, M. et al., "Genosensors and Model Hybridization Studies", *Automation Technologies for Genome Characterization*, Ch. 10 T. Beugelsdijk (Ed), John Wiley & Sons, Inc., pp. 205-225 (1997).

Doublie, S. et al., "Crystal structure of a bacteriophage T7 DNA replication complex at 2.2 A resolution", *Nature*, vol. 391, pp. 251-258 (Jan. 1998).

Driscoll et al., "Atomic-Scale Imaging of DNA Using Scanning Tunneling Microscopy." *Nature*, 346(6281): p. 294-296 (1990).

Drmanac, R. et al., "Sequencing by hybridization: Towards an automated sequencing of one million M13 clones arrayed on membranes", *Electrophoresis*, 13:566-573 (1992).

Duffy et al., "Patterning Electroluminescence Materials with Feature Sizes as Small as 5 um Using Elastomeric Membrains as Masks for Dry Lift-Off," *Advanced Materials* vol. 11, No. 7, pp. 546-552 (1999).

Duffy et al., "Rapid prototyping of microfluidic switches in poly(dimethyl siloxane) and their acuation by electroosmotic flow," *J. Micromech. Microeng.*, vol. 9, pp. 211-217 (1999).

Duffy et al., "Rapid Prototyping of Microfluidic Systems in Poly(dimethylsiloxane)", *Analytical Chemistry*, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).

Effenhauser et al., "Integrated chip-based capillary electrophoresis," *Electrophoresis*, vol. 18, pp. 2203-2213 (1997).

Eigen, M. et al., "Sorting single molecules: Application to diagnostics and evolutionary biotechnology", *PNAS*, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," *J. Micromech. Microeng.*, vol. 5, pp. 169-171(1995).

Ferguson, et al., "A fiber-optic DNA biosensor microarray for the analysis of gene expression," *Nature Biotechnology*, vol. 14, pp. 1681-1684 (1996).

Forster, T., "Delocalized Excitation and Excitation Transfer", Modern Quantum Chem., *Istanbul Lectures*, Part TII, pp. 93-137, Academic Press, New York (1965).

Fritz, I. et al., "Electronic detection of DNA by its intrinsic molecular charge", *PNAS*, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual ATP turnovers by single myosin molecules in aqueous solution", *Nature*, vol. 374, pp. 555-559 (Apr. 1995).

Garcia, A., "Determination of Ion Penneability by Fluorescence Quenching", *Meth. in Enzymology*, 207:501-511 (1992).

Gardner, A., et al., "Acyclic and dideoxy terminator preferences denote divergent sugar recognition by archaeon and *Taq* DNA polymerases", *Nucleic Acids Research*, vol. 30, No. 2, pp. 605-613 (2002).

Gardner et al., "Comparative kinetics of nucleotide analog incorporation by Vent DNA polymerase," *J. Biol. Chem.*, 279, No. 12, p. 11834-11842 (2004).

Giller et al., "Incorporation of reporter molecule-labeled nucleotides by DNA polymerases. I. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5' -Fluorescent-dye-labeled Oligonucleotides", *PCR Methods and Applications*, 2:223-227 (1993).

Goll et al., "Microvalves with bistable buckled polymer diaphragms," *J. Micromech. Microeng.*, vol. 6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley & Sons, Inc.: New York, 1999 3rd Ed.

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C. et al., "A general method for the synthesis of 3'-sulfhydryl and phosphate group containing oligonucleotides", *Nucleic Acids Res.*, 1901:3019-25 (1991).

Gyllenstein, U. et al., "Generation of single-stranded DNA by the polymerase chain reaction and its application to direct sequencing of the *HLA-DQA* locus", *PNAS*, 85:7652-56 (1988).

Ha, "Single molecule dynamics studied by polarization modulation," Phys. Rev. Lett., 77, No. 19, 3979-3982 (1996).

Ha, "Single molecule spectroscopy with automated positioning," Appl. Phys. Lett. 70, No. 6, 782-784 (1997).

Ha, "Single-molecule fluorescence methods for the study of nucleic acids," Current Opinion in Struct Bio, 11, 287-292 (2001).

Ha et al., "Single-molecule fluorescence spectroscopy of enzyme conformational dynamics and cleavage mechanism," *PNAS*, 96(3): p. 893-898 (1999).

Ha, T., "Single-molecue fluorescence resonance energy transfer," *Methods*, 25(1): p. 78-86 (2001).

Hanna, M. et al., "Synthesis and characterization of a new photocrosslinking CTP analog and its use in photoaffmity labeling *E. coli* and T7 RNA polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99 (26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and biomedical applications of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp. 895-897 (1993).

Harrison, D., et al., "Towards miniaturized electrophoresis and chemical analysis systems on silicon: an alternative to chemical sensors", Sensors and Actuators B, 10, pp. 107-116 (1993).

Hasan, A. et al., "Photolabile Protecting Groups for Nucleosides: Synthesis and Photodeprotection Rates", Tetrahedron, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," Anal. Chem., vol. 71, No. 20, pp. 4781-4785 (1999).

Houseal, T. et al., "Real-time imaging of single DNA molecules with fluorescence microscopy", Biophys. 1., vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct observation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", BioTechniques, vol. 10, No. 1, pp. 84-93 (1991).

Hyman, E., "A New Method of Sequencing DNA", Anal. Biochem., 174:423-436 (1988).

Ikuta et al., "Three dimensional micro integrated fluid systems (MIFS) fabricated by stereo lithography", IEEE Kyushu Institute of Technology, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", Cell, vol. 92, pp. 161-171, (Jan. 1998).

Ishikawa, M. et al., "Single-Molecule Detection by Laser-Induced Fluorescence Technique with a Position-Sensitive Photon-Counting Apparatus", Appl. Phys., vol. 33, Part 1, No. 3A, pp. 1571-1576 (1994).

Jacobs et al., "Combinatorial chemistry—applications of light-directed chemical synthesis", TIBTech, vol. 12, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", J. Biomolecular Structure & Dynamics, vol. 7, No. 2, pp. 301-309, (1989).

Johnston, R. et al., "Autoradiography using storage phosphor technology", Electrophoresis, 11 :355-360 (1990).

Jongeneel, C.V., et al., "Comprehensive sampling of gene expression in human cell lines with massively parallel signature sequencing". Proc Natl Acad Sci U S A, 100(8): p. 636-639 (2003).

Joos, B. et al., "Covalent Attachment of Hybridizable Oligonucleotides to Glass Supports", Anal. Biochem. 247(1):96-101 (1997).

Kambara, H. et al., "Optimization of Parameters in a DNA Sequenator using Fluorescence Detection", Biotechnology, vol. 6, pp. 816-821 (1988).

Kartalov, Emil P., et al., "Microfluidic device reads up to four consecutive base pairs in DNA sequencing-by-synthesis", Nucleic Acids Research, vol. 32, No. 9, pp. 2873-2879 (2004).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass", http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", Analytical Biochemistry, 209:63-69 (1993).

Kelso et al., "Single-cell analysis by RT-PCR reveals differential expression of multiple type 1 and 2 cytokine genes among cells within polarized CD4+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", Mole. Bio, Rep. 11: 107-115 (1986).

Khrapko, K. et al., "A method for DNA sequencing by hybridization with oligonucleotide matrix", DNA Sequence-J. DNA Sequencing and Mapping, vol. 1, pp. 375-388 (1991).

Kiefer, J. et al., "Crystal structure of a thermostable Bacillus DNA polymerase I large fragment at 2.1 A resolution", Structure, 5:95-108 (1997).

Kim, Y. et al., "Crystal structure of Thermus aquaticus DNA polymerase", Nature, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R.R. Schmidt, "Application of a ring-closing-metathesis-based linker to the solid phase synthesis of oligosaccharides" Synlett, 11: p. 1802-1804 (1999).

Kopp, et al., "Chemical Amplification: Continuous-Flow PCR on a Chip", Science, vol. 280, pp. 1046-1048 (May 1998).

Korolev, S. et al., "Crystal structure of the large fragment of Thermus aquaticus DNA polymerase I at 2.5 A resolution: Structural basis for thermo stability", PNAS, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch. 1 and Table Ix, Academic Press, New York, pp. 3-40, (1995).

Krider, E. et al., "2'-Modified Nucleosides for Site-Specific Labeling of Oligonucleotides", Bioconjugate Chem., vol. 13, No. 1, pp. 155-162 (2002).

Kuhn, L. et al., "Silicon Charge Electrode Array for Ink Jet Printing", IEEE Trans. On Electron Dev., vol. ED-25, No. 10, pp. 1257-1260 (Oct. 1978).

Lacoste, T. et al., "Ultrahigh-resolution multicolor colocalization of single fluorescent probes", PNAS, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", Antisense and Nucleic Acid Drug Dev., vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", Anal. Chem., vol. 66, pp. 4142-4149 (1994).

Levene, M. et al., "Zero-Mode Waveguides for Single-Molecule Analysis at High Concentrations", Science, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", Anal. Chem., 75:1664-1670 (2003).

Li, Y. et al., "Design, Synthesis, and Spectroscopic Properties of Peptide-Bridged Fluorescence Energy-Transfer Cassettes", *Bioconjuate Chem.*, 10:241-245 (1999).

Li, Y. et al., "Structural Studies of the Klentaq1 DNA Polymerase", *Current Organic Chem.*, 5:871-883 (2001).

Li, Z. et al., "A photocleavable fluorescent nucleotide for DNA sequencing and analysis", *PNAS*, vol. 100, No. 2, pp. 414-419 (2003).

Lin, L. et al., "Free-Space Micromachined Optical Switches for Optical Networking", *IEEE J. of Selected Topics in Quanturn Electronics*, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2002).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", *Science* 243:217-220 (1989).

Lok, Corie, "Deciphering DNA, Top Speed—Helicos BioSciences aims to expedite sequencing, enable genomic medicine," *Technology Review*, pp. 27-28 (May 2005).

Lopez, G. et al., "Fabrication and Imaging of Two-Dimensional Patterns of Proteins Adsorbed on Self-Assembled Monolayers by Scanning Electron Microscopy", *J. Arner. Chem. Soc.*, 115:10774-81 (1993).

Lotters et al., "The mechanical properties of the rubber elastic polymer polydimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'-0-(1-Thiotriphosphates), 5'-triphosphates and 2',3'-Cyclophosphorothioates Using 2-Chloro-4H-1,3,2-benzodioxaphosphorin- 4-one." Journal of Organic Chemistry, 54(3): p. 631-635 (1989).

Lvov, Yu. et al., "Assembly of Thin Films by Means of Successive Deposition of Alternate Layers of DNA and Poly(allylamine)", *American Chemical Society, Macromolecules*, 26, pp. 5396-5399, (1993).

Macklin, J. et al., "Imaging and Time-Resolved Spectroscopy of Single Molecules at an Interface", *Science*, vol. 272, No. 5259, pp. 255-258 (Apr. 1996).

Maier, B., D. Bensimon, and V. Croquette, "Replication by a single DNA polymerase of a stretched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", *Biophys. J.*, vol. 60, pp. 1374-1387 (Dec. 1991).

Marziali, A. and M. Akeson, "New DNA sequencing methods." Annual Review of Biomedical Engineering, 3: p. 195-223 (2001).

Mastrangelo, C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA molecules." Phys Rev Lett, 84(21): p. 5014-7 (2000).

Meldrum, Kevin, "Microfluidics-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." *PNAS*, 97(3): p. 1079-1084 (2000).

Mertz, J. et al., "Single-molecule detection by two-photon-excited fluorescence", *Optics Letters*, vol. 20, No. 24, pp. 2532-2534 (Dec. 1995).

Metzker et al., "Elimination of residual natural nucleotides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'-triphosphates." Nucleic Acids Res, 22(20): p. 4259-67 (1994).

Mitra, Robi, et al., "Fluorescent in situ sequencing on polymerase colonies", *Analytical Biochemistry*, 320, pp. 55-65 (2003).

Moe et al., "Rapid Detection of Clinically Relevant Baceteria in Platelets Using the Hybriscan Bacerterial Detection system, Journal of the American Society of Hematology, 96, No. 11, 4155 (2000).

Moore, P., "To affinity and beyond", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

NIE, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, vol. 208, pp. 171-175 (1993).

Ochman, H. et al., "Genetic Applications of an Inverse Polymerase Chain Reaction", *Genetics* 120:621-623 (1988).

Ohara, To et at, "'Wired' Enzyme Electrodes for Amperometric Determination of Glucose or Lactate in the Presence of Interfering Substances", Ana/. Chem., vol. 66, No. 15, pp. 2451-2457 (Aug. 1994).

Ohara, T. et al., "Glucose Electrodes Based on Cross-Linked [Os(bpY)2CltH Complexed Poly(1-vinylimidazole) Films", *Ana/. Chem.*, vol. 65, pp. 3512-3517 (1993).

Okabe, S. et al., "Do Photobleached Fluorescent Microtubules Move?: Re-evaluation of Fluorescence Laser Photobleaching both In Vitro and in Growing Xenopus Axon", *J. Cell Bio.*, vol. 120, No. 5, pp. 1177-1186 (1993).

Ollis, D. et al., Structure of large fragment of *E. coli* DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Arner. Chem. Soc.*, 92(21):6333-37 (1970).

Padmaja, T., et al., "Enzymatically degradable prodrugs: a novel methodology for drug linkage." Journal of Applied Polymer Science, 85(10): p. 2108-2118 (2002).

Pennisi, E., "Gene researchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et at, "Applications of dielectrophoresis in biotechnology", *Tibtech*, vol. 15, pp. 426-432 (Oct. 1997).

Pisani, F. et at, "Domain Organization and DNA-Induced Conformational Changes of an Archaeal Family B DNA Polymerase", *Biochemistry*, vol. 35, pp. 9158-9166 (Jul. 1996).

Plakhotnik, T. et at, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Laser Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Rapp, R. et al., "LIGA micropump for gases and liquids", *Sensors and Actuators A*, vol. 40, pp. 57-61 (1994).

Rasolonjatovo I. and S.R. Sarfati, "6-N-(N-methylanthranyamido)-4-oxo-hexanoic acid: a new florescent protecting group applicable to a new DNA sequencing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides, 18(4 & 5): p. 1021-1022 (1999).

Reha-Krantz, L., et al., "Genetic and Biochemical Studies of Bacteriophage T4 DNA Polymerase 3'→5'-Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primer Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Ronaghi, M et al., "Real-Time DNA Sequencing Using Detection of Pyrophosphate Release." *Analytical BioChemistry*, 242, No. 0432, (1996).

Rosenblum, B. et al., "New dye-labeled terminators for improved DNA sequencing patterns",*Nucleic Acids Research*, vol. 25, No. 22, pp. 4500-4504 (Nov. 1997).

Rosenblum, B. et al., "Improved single-stranded DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917 (1979).

Ruparel, Hameer, "Design and synthesis of a 3'-O-allyl photocleavable fluorescent nucleotide as a reversible terminator for DNA sequencing by synthesis", *PNAS*, vol. 102, No. 17, pp. 5932-5937 (Apr. 26, 2005).

Ruth, J. et al., "Nucleoside Analogues with Clinical Potential in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-O-(6-aminohexanoyl)-pyrimidine nucleosides 5'-triphosphates that act as DNA polymerase substrates reversibly tagged at C-3'." Journal of the Chemical Society, Perkin Transactions 1: Organic and Bio-Organic Chemistry, 9: p. 1163-71 (1995).

Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts*, vol. 110, No. 16, pp. 409-413 (1988).

Sauer, M., et al.., "Single molecule DNA sequencing in submicrometer channels: state of the art and future prospects." Journal of Biotechnology, 86(3): p. 181-201 (2001).

Schasfoort et al., "Field-effect flow control for microfabricated fluidic networks," Science, vol. 286, pp. 942-945 (1999).

Schueller, O., et al., "Reconfigurable diffraction gratings based on elastomeric microfluidic devices", *Sensors and Actuators*, 78, pp. 149-159 (1998).

Seeger, S. et al., "Single molecule fluorescence—High Performance Diagnosis and Screening", translated from *BIOforum*, pp. 179-185, (Apr. 1998).

Selvin, P., "Fluorescence Resonance Energy Transfer", *Meth. In Enzymology*, vol. 246, pp. 300-335, Academic Press (1995).

Seo, Tae Seok, "Four-color DNA sequencing by synthesis on a chip using photocleavable fluorescent nucleotides", *PNAS*, vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAS*, vol. 101, No. 15, pp. 5488-5493 (Apr. 13, 2004).

Shackelford, James F., "Intro. to Materials Science for Engineers," 3rd Edition, Prentice-Hall, Inc., Macmillan Publ. Co. (1992) (cited by Examiner E. Quan in related case).

Shendure et al., "Advanced sequencing technologies: Methods and goals," *Nature Reviews*, vol. 5, pp. 335-344 (2004).

Shoji, S. et al., "Smallest Dead Volume Microvalves for Integrated Chemical Analyzing Systems", *Proceedings of Transducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature*, vol. 321, pp. 674-679 (Jun. 1986).

Smith, L. et al., "The synthesis of oligonucleotides containing an aliphatic amino group at the 5' terminus: synthesis of fluoresscent DNA primers for use in DNA sequence analysis", *Nucleic Acid Res.*, vol. 13, No. 7, pp. 2399-2412 (1985).

Smith, S. et al., "Direct Mechanical Measurements of the Elasticity of Single DNA Molecules by Using Magnetic Beads", *Science* 258:1122-26 (1992).

Smits, 1., "Piezoelectric Micropump with Three Valves Working Peristaltically", *Sensors and Actuators*, vol. A21-A23, pp. 203-206 (1990).

Song et al., "Influence of the triplet excited state on the photobleaching kinetics of fluorescein in microscopy," Biophysics J., 70, 2959-2968 (1996).

Sproat, B. et al., "The synthesis of protected 5'-mercapto-2',5'-dideoxyribonucleoside- 3' -O-phosphoramidities; uses of 5' -mercapto-oligodeosyribonucleotides", *Nucleic Acids Res.*, 15(12):4837-48 (1987).

Stocki, S. et al., "Dynamics of Bacteriophage T4 DNA Polymerase Function: Identification of Amino Acid Residues that Affect Switching between Polymerase and 3'→5'-Exonuclease Activities", *J. Mol. Biol.*, 254, pp. 15-28 (1995).

Strausberg, R L, et al., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", *Thin Solid Films*, 284-285, pp. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", *Mol. Cell Probes*, vol. 6, No. 4, pp. 265-270 (1992).

Taylor, D. et al., "Characterization of chemisorbed monolayers by surface potential measurements", J. *Phys. D. Appl. Phys.* 24:1443-50 (1991).

Terry, S. et al., "A Gas Chromatogrphic Air Analyzer Fabricated on a Silicon Wafer", *IEEE Trans. on Electron Dev.*, vol. ED-26, No. 12, pp. 1880-1886 (1979).

Theisen, P. et al., "Fluorescent dye phosphoramidite labeling of oligonucleotides", *Nucleic Acids Symp. Ser.*, vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.*, vol. 33, pp. 435-454 (Mar. 1981).

Thompson, N. et al., "Immunoglobulin Surface-Binding Kinetics Studied by Total Internal Reflection with Fluorescence Correlation Spectroscopy",*Biophys. J.*, vol. 43, pp. 103-114 (Jul. 1983).

Thorsen, T. S.J. Maerkl, and S.R. Quake, "Microfluidic large-scale integration." Science, 298(5593): p. 580-4 (2002).

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.*, vol. 235, pp. 47-53 (1997).

Toneguzzo, F. et al., "Use of a Chemically Modified T7 DNA Polymerase for Manual and Automated Sequencing of Super coiled DNA", *BioTech*, vol. 6, No. 5, pp. 460-469 (1988).

Trager, R. S., "DNA sequencing—Venter's next goal: 1000 human genomes." Science, 298(5595): p. 947 (2002).

Tufte, O. et al., "Silicon Diffused-Element Piezoresistive Diaphragms", J. Applied Phys., vol. 31, No. 11, pp. 3322-3327 (Nov. 1962).

Tyagi, S. et al., "Multicolor molecular beacons for allele discrimination", Nat. Biotechnol., 16:49-53 (1998).

Ullman's Encyclopedia of industrial Chemistry, 6ID Edition, vol. 6, Sections 6 to 6.3, Subject: Carbon Black, Wiley-VCH (1999).

Unger et al., "Monolithic mocrofabricated valves and pumps by multilayer soft lithography," Science 288: 113-116 (2000).

Unger, M. et al., "Single-Molecule Fluorescence Observed with Mercury Lamp Illumination", BioTechniques, vol. 27, PD. 1008-1014 (Nov. 1999).

Vale, R. et al., "Direct observation of single kinesin molecules moving along microtubules", Nature, vol. 380, pp. 451-453, (Apr. 1996).

Van Dam, R.M. and S.R Quake, "Gene expression analysis with universal n-mer arrays." Genome Res, 12(1): p. 145-52 (2002).

Van De Pol, F. et al., "Micro-liquid handling devices: A Review", Micro System Technologies 90, 1st IntI. Conf. On Micro Electro, Opto, Mechanic Systems and Components, pp. 799-805, Berlin, Springer-Verlag, (1990).

Van Oijen et al., "Single molecule kinetics of λ exonuclease reveal base dependence and dynamic disorder," Science, 301, 1235-1238 (2003).

Venter, J.L., et al., "The sequence of the human genome." Science, 291(5507): p. 1304-1351 (2001).

Vielder, C. et al., "A Pneumatically Actuated Micro Valve With A Silicone Rubber Membrane For Integration With Fluid-Handling Systems", Proceedings of Transducers '95, pp. 284-286, Stockholm (1995).

Walker, M.G., et al., "Prediction of gene function by genome-scale expression analysis: Prostate cancer-associated genes.": Genome Researce, 9(12): p. 1198-1203 (1999).

Wang, G. et al., "Design and Synthesis of New Fluorogenic H1V Protease Substrates Based on Resonance Energy Transfer", Tetrahedron Lett., 31(45):6493-96 (1990).

Wang, M.D., et al., "Force and Velocity measured for single molecules of RNA polymerase." Science, 282(5390): p. 902-907 (1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", J. Biomed. Mater. Res., vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", IntI. Con£ on MEMS (MEMS 96), pp. 491-496 (1996).

Wedekind, P. et al., "Scanning microphotolysis: a new photobleaching technique based on fast intensity modulation of a scanned laser beam and confocal imaging", J. Microscopy, vol. 176, Pt. 1, pp. 23-33 (Oct. 1994).

Weir, et al., "Hybrigel Purification: A Novel Technique for Accelerated Preparation of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", Science, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme." Nucleosides & Nucleotides, 18(2): p. 197-201 (1999).

Werner et al "Progress towards single-molecule DNA sequencing: a one color demonstration." J Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", J. Bioi. Chem., 237(6):2834-41 (1982).

Winter et al., "Direct gene expression analysis," Curr. Pharm. Biotech., 5, p. 191-197 (2004).

Wu, et al., "Synthesis and Properties of Adenosine-5'-triphosphoro-γ-1-(5-sulfonic acid)naphthyl Ethylamide: A Fluorescent Nucleotide Substrate for DNA-Dependent RNA Polymerase from Escherichia coli," Archives of Biochemistry and Biophysics, vol. 246, No. 2, pp. 564-571 (1986).

Wuite, G. et al., "Single-molecule studies of the effect of template tension on T7 DNA polymerase activity", Nature, 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 550-575 (1998).

Xia, G., et al., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", Science, vol. 275, pp. 1106-1109, (Feb. 1997).

Xu, X. et al., "Long-Range Electrostatic Trapping of Single-Protein Molecules at a Liquid-Solid Interface", Science, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Actuators, vol. A64, No. 1, pp. 101-108 (1998).

Yazdi, N. et al., "Micromachined Inertial Sensors", Proceedings of the IEEE, vol. 86, No., pp. 1640-1659 (Aug. 1998).

Yershov, G. et al., "DNA analysis and diagnostics on oligonucleotide microchips", Proc. Natl. Acad. Sci. USA, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et aI., "Cyanine dye dUTP analogs for enzymatic labeling of DNA probes." Nucleic Acids Res, 22(15): p. 3226-32 (1994).

Zdeblick, M. et al., "A Microminiature Electric-To-Fluidic Valve", Transducers '87, reprinted in Micromechanics and MEMS Classic and Seminal Papers to 1990, IEEE Press, pp. 437-439 (1987).

Zhu, Z. et al., "Molecular Mechanism Controlling the Incorporation of Fluorescent Nucleotides into DNA by PCR", Cytometry, 28:206-211 (1997).

Zhu, Z. et al., "Directly labeled DNA probes using fluorescent nucleotides with different length linkers", Nucleic Acids Res., vol. 22, No. 16, pp. 3418-3422 (1994).

Zuckerman, R. et al., "Efficient methods for attachment of thiol specific probes to the 3' ends of synthetic oligodeoxyribonucleotides", Nucleic Acids Res., 15(13):5305-5321 (1987).

Therminator DNA Polymerase FAQ, http://www.neb.com/nebecomm/products/faqproductM0261.asp downloaded Jun. 1, 2005, 1 page.

\* cited by examiner

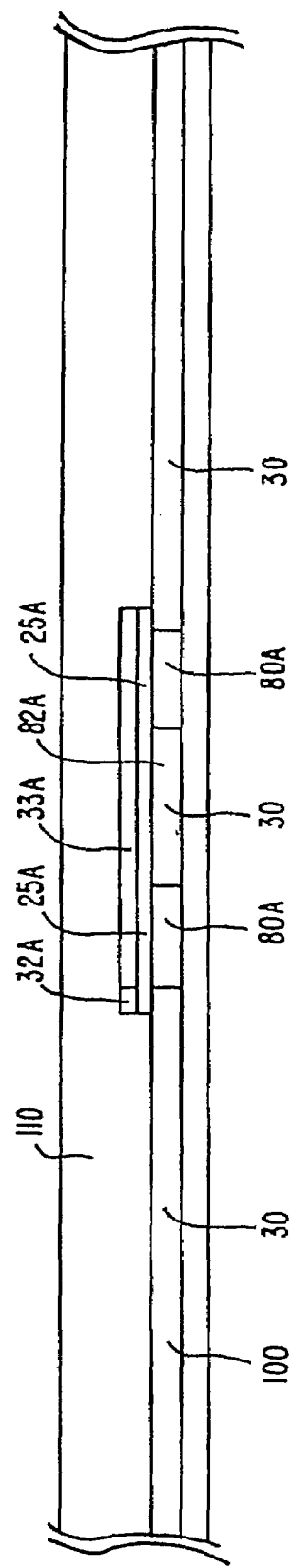

METHODS AND APPARATUSES FOR ANALYZING POLYNUCLEOTIDE SEQUENCES

REFERENCE TO OTHER APPLICATIONS

This non-provisional patent application claims the benefit of U.S. Provisional Application No. 60/526,162, filed Dec. 1, 2003 and is a continuation-in-part of U.S. patent application Ser. No. 09/908,830 filed Jul. 18, 2001, now U.S. Pat. No. 6,818,395, which is a divisional of U.S. patent application Ser. No. 09/707,737 filed Nov. 6, 2000, which claimed the benefit of U.S. provisional patent application No. 60/163,742 filed Nov. 4, 1999 and was a continuation-in-part of U.S. patent application Ser. No. 09/605,520 filed Jun. 27, 2000, which in turn claims the benefit of U.S. provisional patent application No. 60/141,503 filed Jun. 28, 1999, U.S. provisional patent application No. 60/147,199 filed Aug. 3, 1999, and U.S. provisional patent application No. 60/186,856 filed Mar. 3, 2000. Reference is also made to U.S. non-provisional application Ser. No. 11/002,739 filed on Dec. 1, 2004, by Quake et al. The text of each of the foregoing patent applications is hereby incorporated by reference.

GOVERNMENT INTEREST

Work described herein has been supported, in part, by National Institutes of Health Grant Nos. HG-01642 and 5T32-GM07616, and by Defense Advanced Research Projects Agency Grant No. DAAD19-001-0392 . The U.S. Government may therefore have certain rights in the invention.

FIELD OF THE INVENTION

The present invention relates to methods for high speed, high throughput analysis of polynucleotide sequences and apparatuses for carrying out such methods.

BACKGROUND OF THE INVENTION

Traditional DNA sequencing techniques share three essential steps in their approaches to sequence determination. First, a multiplicity of DNA fragments are generated from a DNA species which it is intended to sequence. These fragments are incomplete copies of the DNA species to be sequenced. The aim is to produce a ladder of DNA fragments, each a single base longer than the previous one. For example, with the Sanger method (Sanger et al., Proc. Natl. Acad. Sci. USA 74:5463, 1977), the target DNA is used as a template for a DNA polymerase to produce a number of incomplete clones. These fragments, which differ in respective length by a single base, are then separated on an apparatus which is capable of resolving single-base differences in size. The third and final step is the determination of the nature of the base at the end of each fragment. When ordered by the size of the fragments which they terminate, these bases represent the sequence of the original DNA species.

Automated systems for DNA sequence analysis have been developed, such as discussed in Toneguzzo et al., 6 Biotechniques 460, 1988; Kanbara et al., 6 Biotechnology 816, 1988; and Smith et al., 13 Nuc. Acid. Res. 13: 2399, 1985; U.S. Pat. No. 4,707,237 (1987). However, all these methods still require separation of DNA products by a gel permeation procedure and then detection of their locations relative to one another along the axis of permeation or movement through the gel. These apparatuses used in these methods are not truly automatic sequencers. They are merely automatic gel readers, which require the standard sequencing reactions to be carried out before samples are loaded onto the gel.

The disadvantages of the above methods are numerous. The most serious problems are caused by the requirement for the DNA fragments to be size-separated on a polyacrylamide gel. This process is time-consuming, uses large quantities of expensive chemicals, and severely limits the number of bases which can be sequenced in any single experiment, due to the limited resolution of the gel. Sanger dideoxy sequencing has a read length of approximately 500 bp, a throughput that is limited by gel electrophoresis (appropriately 0.2%).

Other methods for analyzing polynucleotide sequences have been developed more recently. In some of these methods broadly termed sequencing by synthesis, template sequences are determined by priming the template followed by a series of single base primer extension reactions (e.g., as described in WO 93/21340, WO 96/27025, and WO 98/44152). While the basic scheme in these methods no longer require separation of polynucleotides on the gel, they encounter various other problems such as consumption of large amounts of expensive reagents, difficulty in removing reagents after each step, misincorporation due to long exchange times, the need to remove labels from the incorporated nucleotide, and difficulty to detect further incorporation if the label is not removed. Many of these difficulties stem directly from limitations of the macroscopic fluidics employed. However, small-volume fluidics have not been available. As a result, these methods have not replaced the traditional gel-based sequencing schemes in practice. The skilled artisans are to a large extent still relying on the gel-based sequencing methods.

Thus, there is a need in the art for methods and apparatuses for high speed and high throughput analysis of longer polynucleotide sequences which can be automated utilizing the available scanning and detection technology. The present invention fulfills this and other needs.

SUMMARY OF THE INVENTION

The invention provides methods and apparatuses for analyzing a nucleic acid. In one embodiment, the invention provides a novel attachment scheme for a nucleic acid on a substrate. In general terms, according to this embodiment, a substrate is provides that comprises poly(dimethylsiloxane), a poly(ethylene glycol) layer and a polyelectrolyte multilayer. The substrate may be composes of poly(dimethylsiloxane) or may comprise a layer or coating of poly(dimethylsiloxane). The poly(ethylene glycol) layer is positioned between the poly(dimethylsiloxane) layer and serves to link the polyelectroyte multilayer to the poly(dimethylsiloxane). A nucleic acid is attached to the substrate either directly or through a chemical linkage, such as a streptavidin-biotin link. According to the invention, the novel surface chemistry provides a specific and tunable derivatization of poly(dimethylsiloxane).

In another aspect of the present invention, methods for analyzing the sequence of a target polynucleotide are provided. The methods include the steps of (a) providing a primed target polynucleotide linked to a microfabricated synthesis channel; (b) flowing a first nucleotide through the synthesis channel under conditions whereby the first nucleotide attaches to the primer, if a complementary nucleotide is present to serve as template in the target polynucleotide; (c) determining presence or absence of a signal, the presence of a signal indicating that the first nucleotide was incorporated into the primer, and hence the identity of the complementary base that served as a template in the target polynucleotide; (d)

removing or reducing the signal, if present; and (e) repeating steps (b)-(d) with a further nucleotide that is the same or different from the first nucleotide, whereby the further nucleotide attaches to the primer or a nucleotide previously incorporated into the primer.

In some methods, step (a) comprises providing a plurality of different primed target polynucleotides linked to different synthesis channels; step (b) comprises flowing the first nucleotide through each of the synthesis channels; and step (c) comprises determining presence or absence of a signal in each of the channels, the presence of a signal in a synthesis channel indicating the first nucleotide was incorporated into the primer in the synthesis channel, and hence the identity of the complementary base that served as a template in the target polynucleotide in the synthesis channel. In some methods, a plurality of different primed target polynucleotides are linked to each synthesis channels.

Some methods include the further steps of flushing the synthesis channel to remove unincorporated nucleotides. In some methods, steps (b)-(d) are performed at least four times with four different types of nucleotides. In some methods, steps (b)-(d) are performed until the identity of each base in the target polynucleotide has been identified.

In some methods, the nucleotides are labeled. The label can be a fluorescent dye, and the signal can be detected optically. The label can also be a radiolabel, and the signal can be detected with a radioactivity detector. In some methods, incorporation of nucleotides is detected by measuring pyrophosphate release.

In some methods, the synthesis channel is formed by bonding a microfluidic chip to a flat substrate. In some of these methods, the target polynucleotides are immobilized to the interior surface of the substrate in the synthesis channel. In some of these methods, the interior surface is coated with a polyelectrolyte multilayer (PEM). In some of these methods, the microfluidic chip is fabricated with an elastomeric material such as RTV silicone.

In another aspect of the present invention, methods for analyzing a target polynucleotide entails (a) pretreating the surface of a substrate to create surface chemistry that facilitates polynucleotide attachment and sequence analysis; (b) providing a primed target polynucleotide attached to the surface; (c) providing a labeled first nucleotides to the attached target polynucleotide under conditions whereby the labeled first nucleotide attaches to the primer, if a complementary nucleotide is present to serve as template in the target polynucleotide; (d) determining presence or absence of a signal from the primer, the presence of a signal indicating that the labeled first nucleotide was incorporated into the primer, and hence the identity of the complementary base that served as a template in the target polynucleotide; and (e) repeating steps (c)-(d) with a labeled further nucleotide that is the same or different from the first labeled nucleotide, whereby the labeled further nucleotide attaches to the primer or a nucleotide previously incorporated into the primer.

In some of these methods, the substrate is glass and the surface is coated with a polyelectrolyte multilayer (PEM). In some methods, the PEM is terminated with a polyanion. In some methods, the polyanion is terminated with carboxylic acid groups. In some methods, the target polynucleotide is biotinylated, and the PEM-coated surface is further coated with biotin and then streptavidin.

In still another aspect of the present invention, methods of analyzing a target polynucleotide are provided which include the steps of (a) providing a primed target polynucleotide; (b) providing a first type of nucleotide of which a fraction is labeled under conditions whereby the first nucleotide attaches to the primer, if a complementary nucleotide is present to serve as template in the target polynucleotide; (c) determining presence or absence of a signal from the primer, the presence of a signal indicating the first nucleotide was incorporated into the primer, and hence the identity of the complementary base that served as a template in the target polynucleotide; and (d) repeating steps (b)-(c) with a further type of nucleotide of which a fraction is labeled the same and which is the same or different from the first type of nucleotide, whereby the further nucleotide attaches to the primer or a nucleotide previously incorporated into the primer.

In some of these methods, the label used is a fluorescent label. In some of these methods, the removing or reducing step is performed by photobleaching. In some of these methods, the fraction of labeled nucleotides are less than 10%, less than 1%, less than 0.1%, or less than 0.01%.

In another aspect of the present invention, apparatuses for analyzing the sequence of a polynucleotide are provided. The apparatuses have (a) a flow cell with at least one microfabricated synthesis channel; and (b) an inlet port and an outlet port which are in fluid communication with the flow cell and which flowing fluids such as deoxynucleoside triphosphates and nucleotide polymerase into and through the flow cell. Some of the apparatuses additionally have (c) a light source to direct light at a surface of the synthesis channel; and (d) a detector to detect a signal from the surface.

In some of the apparatuses, the synthesis channel is formed by bonding a microfluidic chip to a flat substrate. In some apparatuses, the microfluidic chip also contain microfabricated valves and microfabricated pumps in an integrated system with the synthesis channel. In some of these apparatuses, a plurality of reservoirs for storing reaction reagents are also present, and the microfabricated valve and pump are connected to the reservoirs. In some apparatuses, the detector is a photon counting camera. In some of the apparatuses, the microfluidic chip is fabricated with an elastomeric material such as RTV silicone. The substrate of some of the apparatuses is a glass cover slip. The cross section of the synthesis channel in some of the apparatuses has a linear dimension of less than 100 μm×100 μm, less than 1 μm×100 μm, less than 1 μm×10 μm, or less than 0.1 μm×1 μm.

BRIEF DESCRIPTION OF THE DRAWINGS

FIG. 22D is a sectional elevation view corresponding to FIG. 22C, taken along line 28D-28D in FIG. 22C.

FIG. 29A specifically shows a flow layer and a control layer, as well as a derivatization tree and a sequencing tree defined by the microchannels.

DETAILED DESCRIPTION

I. Overview

Figure 1:
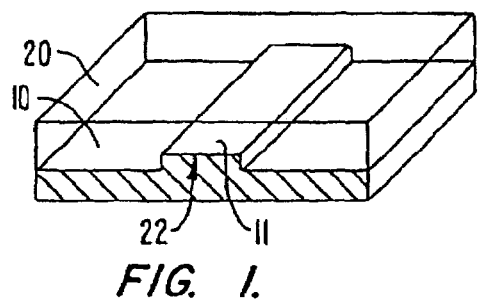
FIG. 1 is an illustration of a first elastomeric layer formed on top of a micromachined mold.

The present invention provides methods and apparatuses for analyzing polynucleotide sequences.

In some methods, the sequencing apparatuses comprise a microfabricated flow channel to which polynucleotide templates are attached. Optionally, the apparatuses comprise a plurality of microfabricated channels, and diverse polynucleotide templates can be attached to each channel. The apparatuses can also have a plurality of reservoirs for storing various reaction reagents, and pumps and valves for controlling flow of the reagents. The flow cell can also have a window to allow optical interrogation.

In these methods, single stranded polynucleotide templates with primers are immobilized to the surface of the microfabricated channel or to the surface of reaction chambers that are disposed along a microfabricated flow channel, e.g., with streptavidin-biotin links. After immobilization of the templates, a polymerase and one of the four nucleotide triphosphates are flowed into the flow cell, incubated with the template, and flowed out. If no signal is detected, the process is repeated with a different type of nucleotide.

These methods are advantageous over the other sequencing by synthesis methods discussed previously. First, use of microfabricated sequencing apparatuses reduces reagent consumption. It also increases reagent exchange rate and the speed of sequence analysis. In addition, the microfabricated apparatuses provides parallelization: many synthesis channels can be built on the same substrate. This allows analysis of a plurality of diverse polynucleotide sequences simultaneously. Further, due to the reduction of time and dead volume for exchanging reagents between different steps during the analysis, mismatch incorporation is greatly reduced. Moreover, the read length is also improved because there is less time for the polymerase to incorporate a wrong nucleotide and it is less likely that the polymerase falls off the template. All these advantages result in high speed and high throughput sequence analysis regimes.

In some methods of the present invention, the surface of a substrate (e.g., a glass cover slip) is pretreated to create optimal surface chemistry that facilitates polynucleotide template attachment and subsequent sequence analysis. In some of these methods, the substrate surface is coated with a polyelectrolyte multilayer (PEM). Following the PEM coating, biotin can be applied to the PEM, and followed by application of streptavidin. The substrate surface can then be used to attach biotinylated-templates. The PEM-coated substrate provides substantial advantages for immobilizing the template polynucleotides and for polymerase extension reaction. First, because PEM can easily be terminated with polymers bearing carboxylic acids, it is easy to attach polynucleotides. Second, the attached template is active for extension by polymerases—most probably, the repulsion of like charges prevents the template from "laying down" on the surface. Finally, the negative charge repels nucleotides, and nonspecific binding is low.

In some other methods of the present invention, only a small percentage of each type of nucleotides present in the extension reaction is labeled, e.g., with fluorescent dye. As a result, relatively small numbers of incorporated nucleotides are fluorescently labeled, interference of energy transfer is minimized, and the polymerase is less likely to fall off the template or be "choked" by incorporation of two labeled nucleotides sequentially.

Optionally, the incorporated fluorescent signals are extinguished by photobleaching. Employment of photobleaching strategy can reduce the number of steps (e.g., it may not be necessary to perform the removal of label after every extension cycle). These advantages lead to more accurate detection of incorporated signals, more efficient consumption of polymerase, and a fast sequencing method.

II. Sequencing Apparatuses

A. Basic Features of the Apparatuses

The apparatuses comprise microfabricated channels to which polynucleotide templates to be sequenced are attached. Optionally, the apparatuses comprise plumbing components (e.g., pumps, valves, and connecting channels) for flowing reaction reagents. The apparatuses can also comprise an array of reservoirs for storing reaction reagents (e.g., the polymerase, each type of nucleotides, and other reagents can each be stored in a different reservoir).

The microfabricated components of the apparatuses all have a basic "flow channel" structure. The term "flow channel" or "microfabricated flow channel" refers to recess in a structure which can contain a flow of fluid or gas. The polynucleotide templates are attached to the interior surface of microfabricated channels in which synthesis occurs. For consistency and clarity, the flow channels are termed "synthesis channel" when referring to such specific use. The microfabricated flow channels can also be actuated to function as the plumbing components (e.g., micro-pumps, micro-valves, or connecting channels) of the apparatuses.

In some applications, microfabricated flow channels are cast on a chip (e.g., a elastomeric chip). Synthesis channels are formed by bonding the chip to a flat substrate (e.g., a glass cover slip) which seals the channel. Thus, one side of the synthesis channel is provided by the flat substrate. Typically, the polynucleotide templates are attached to the interior surface of the substrate within the synthesis channel.

The plumbing components can be microfabricated as described in the present invention. For example, the apparatuses can contain in an integrated system a flow cell in which a plurality of synthesis channels are present, and fluidic components (such as micro-pumps, micro-valves, and connecting channels) for controlling the flow of the reagents into and out of the flow cell. Alternatively, the sequencing apparatuses of the present invention utilize plumbing devices described in, e.g., Zdeblick et al., A Microminiature Electric-to-Fluidic Valve, Proceedings of the 4th International Conference on Solid State Transducers and Actuators, 1987; Shoji et al., Smallest Dead Volume Microvalves for Integrated Chemical Analyzing Systems, Proceedings of Transducers '91, San Francisco, 1991; Vieider et al., A Pneumatically Actuated Micro Valve with a Silicon Rubber Membrane for Integration with Fluid Handling Systems, Proceedings of Transducers '95, Stockholm, 1995.

As noted above, at least some of the components of the apparatuses are microfabricated. Employment of microfabricated synthesis channels and/or microfabricated plumbing components significantly reduce the dead volume and decrease the amount of time needed to exchange reagents, which in turn increase the throughput. Microfabrication refers to feature dimensions on the micron level, with at least one dimension of the microfabricated structure being less than 1000 µm. In some apparatuses, only the synthesis channels are microfabricated. In some apparatuses, in addition to the synthesis channels, the valves, pumps, and connecting channels are also microfabricated. Unless otherwise specified, the discussion below of microfabrication is applicable to production of all microfabricated components of the sequencing apparatuses (e.g., the synthesis channels in which sequencing reactions occur, and the valves, pumps, and connecting channels for controlling reagents flow to the synthesis channels).

Various materials can be used to fabricate the microfabricated components (see, e.g., Unger et al., Science 288:113-116, 2000). Preferably, elastomeric materials are used. Thus, in some apparatuses, the integrated (i.e., monolithic) microstructures are made out of various layers of elastomer bonded together. By bonding these various elastomeric layers together, the recesses extending along the various elastomeric layers form flow channels through the resulting monolithic, integral elastomeric structure.

In general, the microfabricated structures (e.g., synthesis channels, pumps, valves, and connecting channels) have widths of about 0.01 to 1000 microns, and a width-to-depth ratios of between 0.1:1 to 100:1. Preferably, the width is in the range of 10 to 200 microns, a width-to-depth ratio of 3:1 to 15:1.

B. Microfabrication with Elastomeric Materials

1. Basic Methods of Microfabrication

Various methods can be used to produce the microfabricated components of the sequencing apparatuses of the present invention. Fabrication of the microchannels, valves, pumps can be performed as described in Unger et al., Science 288:113-116, 2000, which is incorporated herein by reference. In some methods (FIGS. 1 to 7B, pre-cured elastomer layers are assembled and bonded to produce a flow channel. As illustrated in FIG. 1, a first micro-machined mold 10 is provided. Micro-machined mold 10 can be fabricated by a number of conventional silicon processing methods, including but not limited to photolithography, ion-milling, and electron beam lithography. The micro-machined mold 10 has a raised line or protrusion 11 extending therealong. A first elastomeric layer 20 is cast on top of mold 10 such that a first recess 21 can be formed in the bottom surface of elastomeric layer 20, (recess 21 corresponding in dimension to protrusion 11), as shown.

Figure 2:
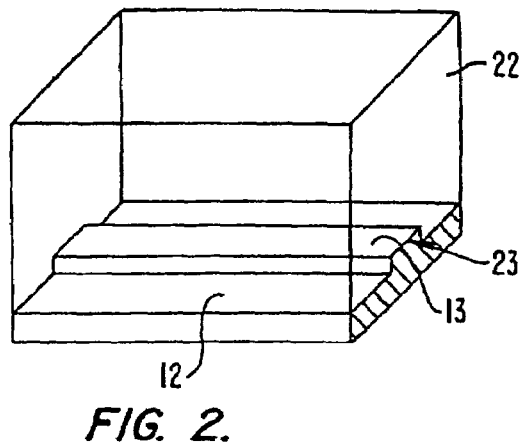
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 can be formed in its bottom surface corresponding to the dimensions of protrusion 13.

Figure 3:
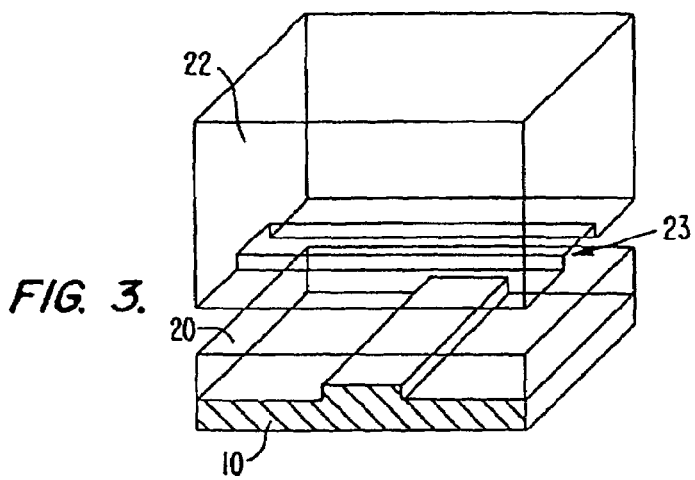
FIG. 3 is an illustration of the elastomeric layer of FIG. 2 removed from the micromachined mold and positioned over the top of the elastomeric layer of FIG. 1.
Figure 4:
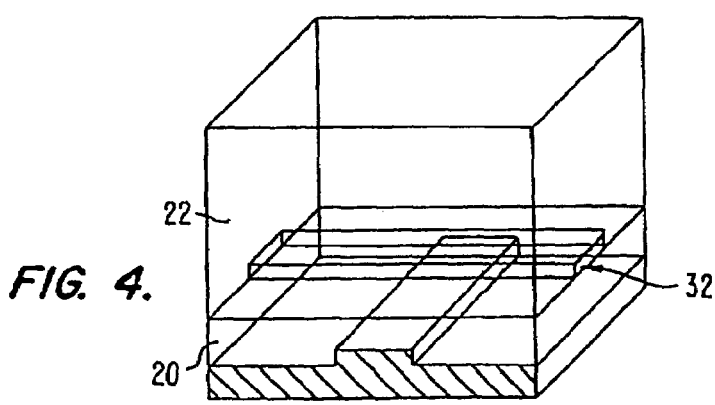
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 forms a flow channel 32.

Figure 5:
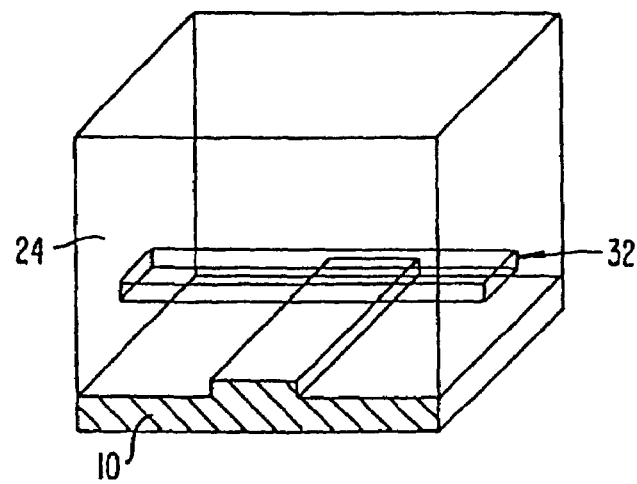
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
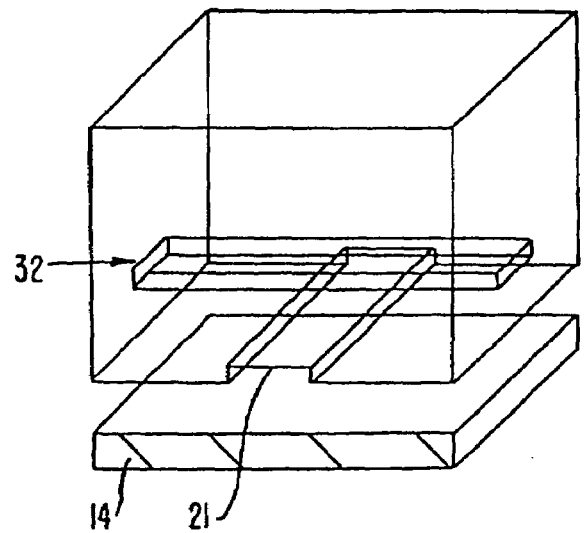
FIG. 6 is an illustration corresponding to FIG. 5, but showing the first micromachine mold removed and a planar substrate positioned in its place.
Figure 7A:
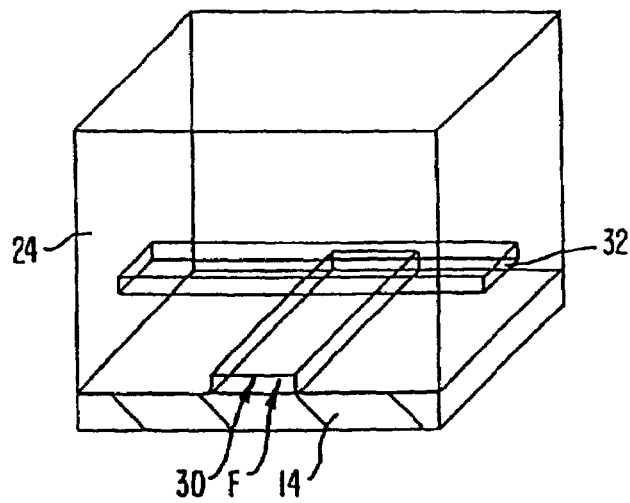
FIG. 7A is an illustration corresponding to FIG. 6, but showing the elastomeric structure sealed onto the planar substrate.
Figure 7B:
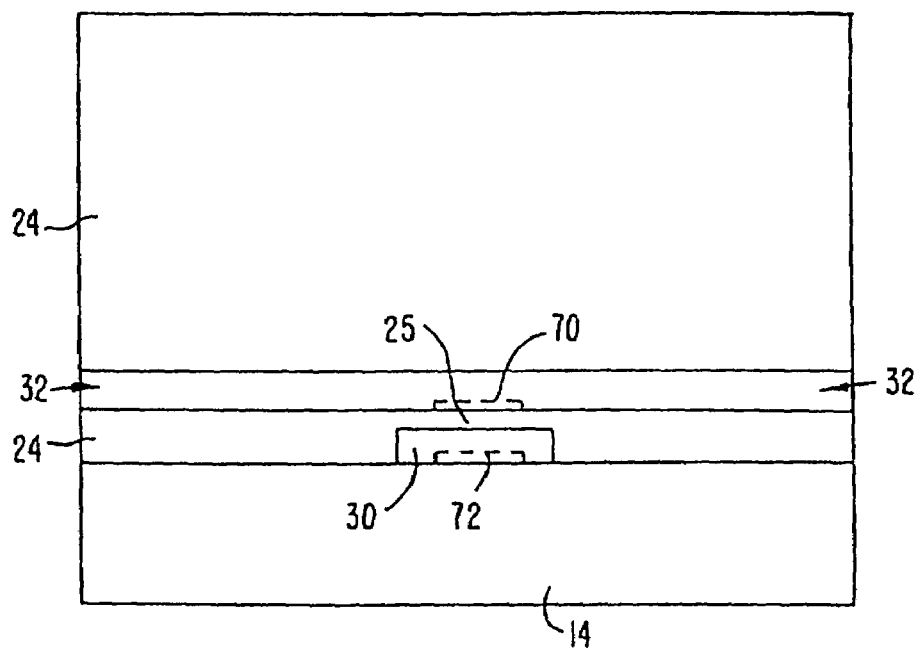
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 forms a flow channel 30.

The present elastomeric structures form a reversible hermetic seal with nearly any smooth planar substrate. An advantage to forming a seal this way is that the elastomeric structures can be peeled up, washed, and re-used. In some apparatuses, planar substrate 14 is glass. A further advantage of using glass is that glass is transparent, allowing optical interrogation of elastomer channels and reservoirs. Alternatively, the elastomer structure can be bonded onto a flat elastomer layer by the same method as described above, forming a permanent and high-strength bond. This can prove advantageous when higher back pressures are used.

In some methods, microfabrication involves curing each layer of elastomer "in place" (FIGS. 8 to 18). In these methods, flow and control channels are defined by first patterning sacrificial layer on the surface of an elastomeric layer (or other substrate, which can include glass) leaving a raised line of sacrificial layer where a channel is desired. Next, a second layer of elastomer is added thereover and a second sacrificial layer is patterned on the second layer of elastomer leaving a raised line of sacrificial layer where a channel is desired. A third layer of elastomer is deposited thereover. Finally, the sacrificial layer is removed by dissolving it out of the elastomer with an appropriate solvent, with the voids formed by removal of the sacrificial layer becoming the flow channels passing through the substrate.

Figure 8:
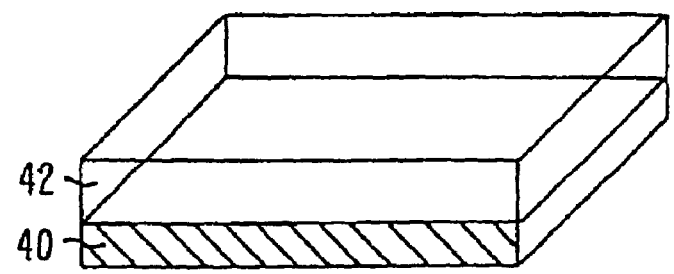
FIG. 8 is an illustration of a first elastomeric layer deposited on a planar substrate.
Figure 9:
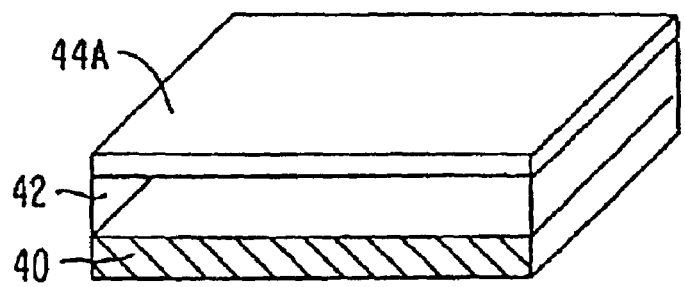
FIG. 9 is an illustration showing a first sacrificial layer deposited on top of the first elastomeric layer of FIG. 8.
Figure 10:
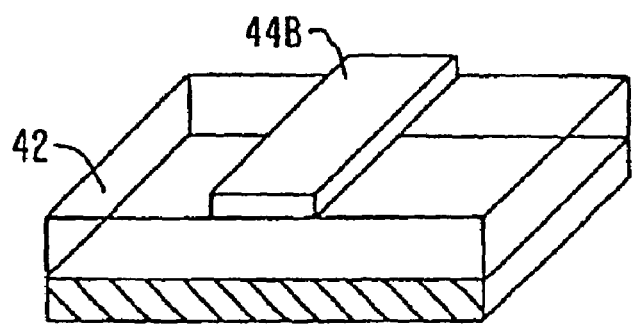
FIG. 10 is an illustration showing the system of FIG. 9, but with a portion of the first sacrificial layer removed, leaving only a first line of sacrificial layer.
Figure 11:
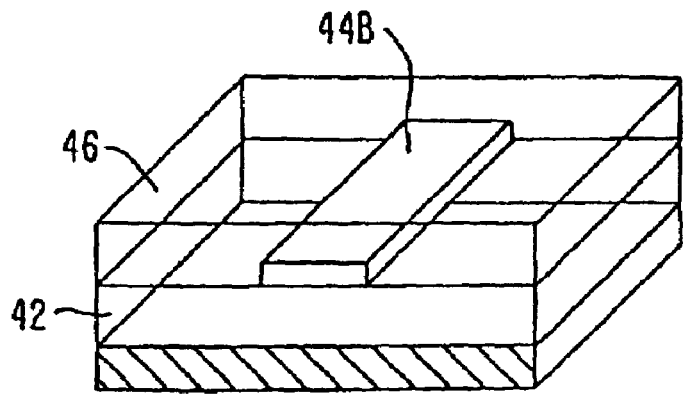
FIG. 11 is an illustration showing a second elastomeric layer applied on top of the first elastomeric layer over the first line of sacrificial layer of FIG. 10, thereby encasing the sacrificial layer between the first and second elastomeric layers.
Figure 12:
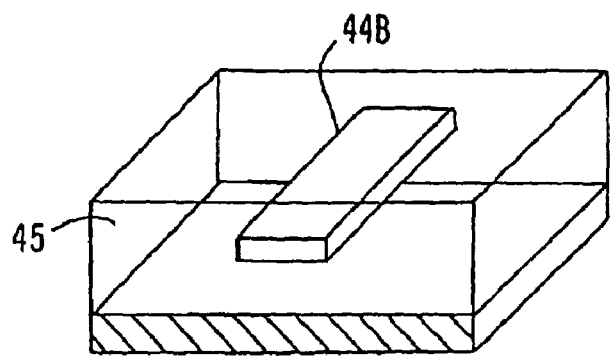
FIG. 12 corresponds to FIG. 11, but shows the integrated monolithic structure produced after the first and second elastomer layers have been bonded together.

Referring first to FIG. 8, a planar substrate 40 is provided. A first elastomeric layer 42 is then deposited and cured on top of planar substrate 40. Referring to FIG. 9, a first sacrificial layer 44A is then deposited over the top of elastomeric layer 42. Referring to FIG. 10, a portion of sacrificial layer 44A is removed such that only a first line of sacrificial layer 44B remains as shown. Referring to FIG. 11, a second elastomeric layer 46 is then deposited over the top of first elastomeric layer 42 and over the first line of sacrificial layer 44B as shown, thereby encasing first line of sacrificial layer 44B between first elastomeric layer 42 and second elastomeric layer 46. Referring to FIG. 12, elastomeric layers 46 is then cured on layer 42 to bond the layers together to form a monolithic elastomeric substrate 45.

Figure 13:
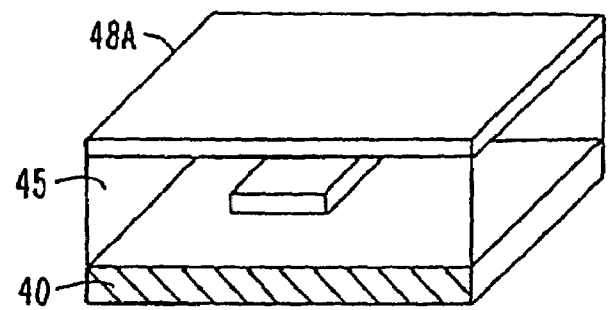
FIG. 13 is an illustration showing a second sacrificial layer deposited on top of the integral elastomeric structure of FIG. 12.
Figure 14:
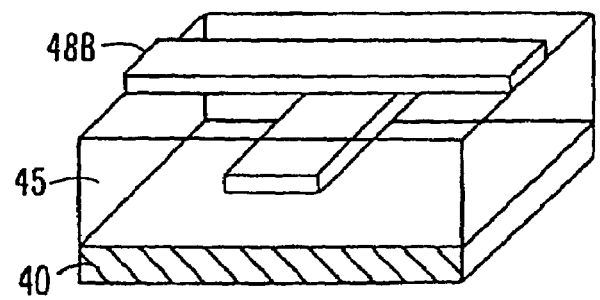
FIG. 14 is an illustration showing the system of FIG. 13, but with a portion of the second sacrificial layer removed, leaving only a second line of sacrificial layer.
Figure 15:
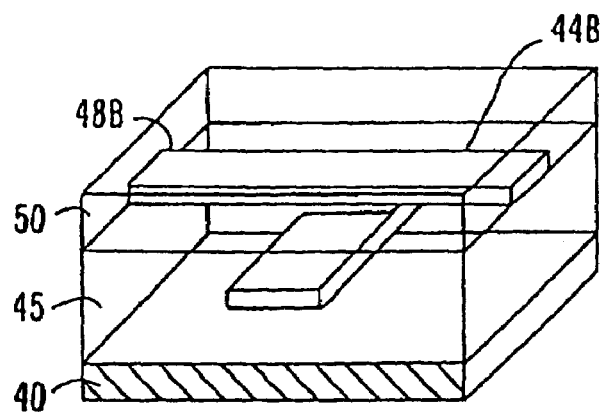
FIG. 15 is an illustration showing a third elastomer layer applied on top of the second elastomeric layer and over the second line of sacrificial layer of FIG. 14, thereby encapsulating the second line of sacrificial layer between the elastomeric structure of FIG. 12 and the third elastomeric layer.

Referring to FIG. 13, a second sacrificial layer 48A is then deposited over elastomeric structure 45. Referring to FIG. 14, a portion of second sacrificial layer 48A is removed, leaving only a second sacrificial layer 48B on top of elastomeric structure 45 as shown. Referring to FIG. 15, a third elastomeric layer 50 is then deposited over the top of elastomeric structure 45 (comprised of second elastomeric layer 42 and first line of sacrificial layer 44B) and second sacrificial layer 48B as shown, thereby encasing the second line of sacrificial layer 48B between elastomeric structure 45 and third elastomeric layer 50.

Figure 16:
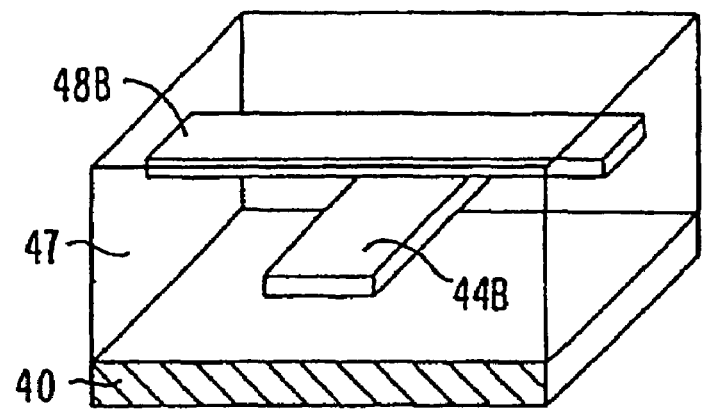
FIG. 16 corresponds to FIG. 15, but shows the third elastomeric layer cured so as to be bonded to the monolithic structure composed of the previously bonded first and second elastomer layers.
Figure 17:
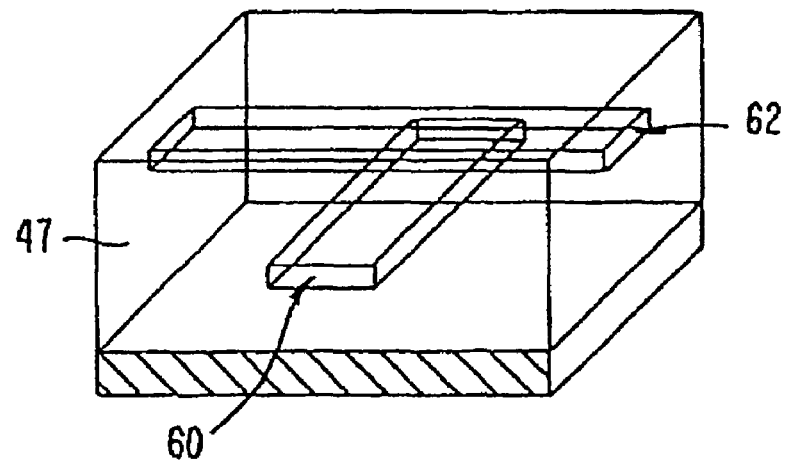
FIG. 17 corresponds to FIG. 16, but shows the first and second lines of sacrificial layer removed so as to provide two perpendicular overlapping, but not intersecting, flow channels passing through the integrated elastomeric structure.
Figure 18:
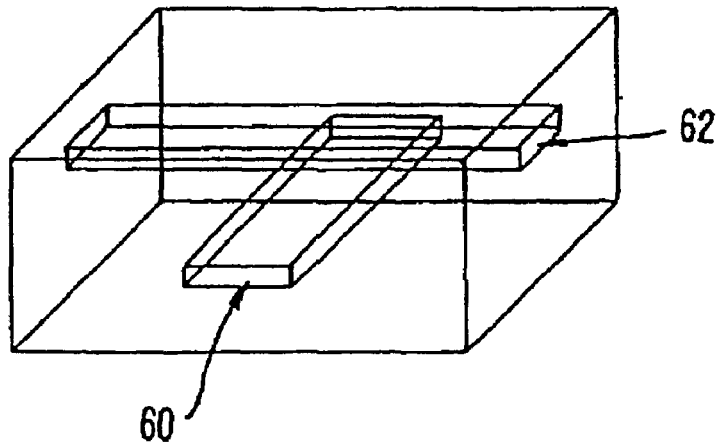
FIG. 18 is an illustration showing the system of FIG. 17, but with the planar substrate thereunder removed.
Figure 19:
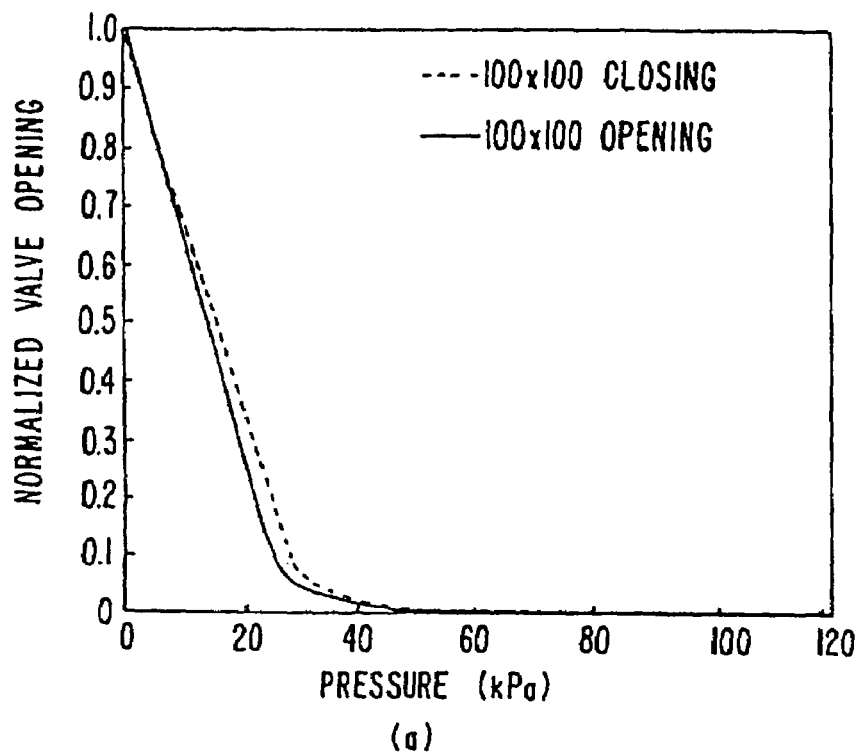
FIG. 19 illustrates valve opening vs. applied pressure for various flow channels.
Figure 19:
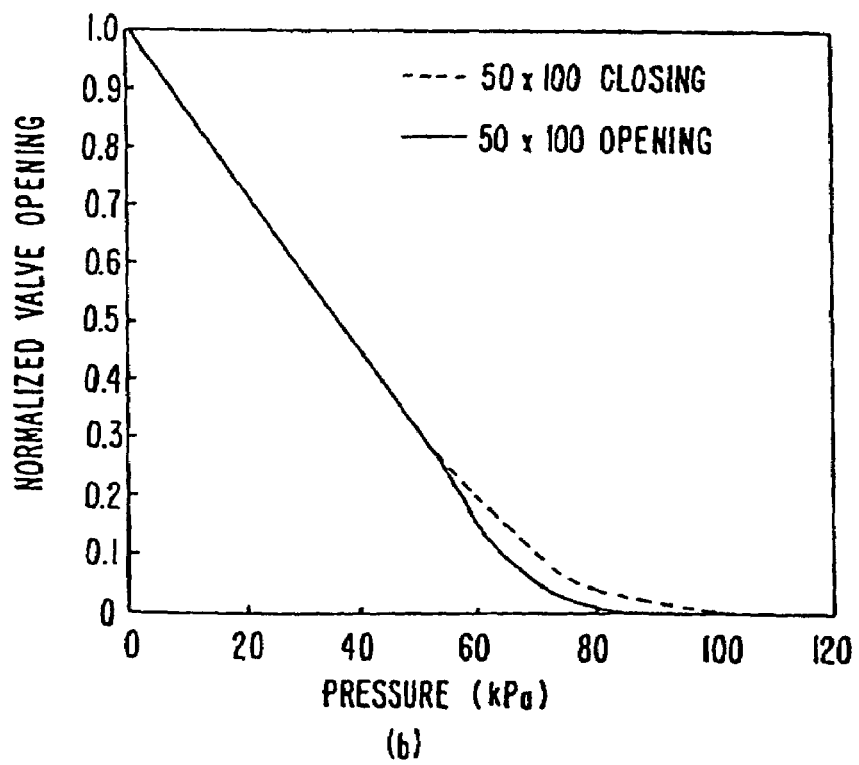
Figure 20:
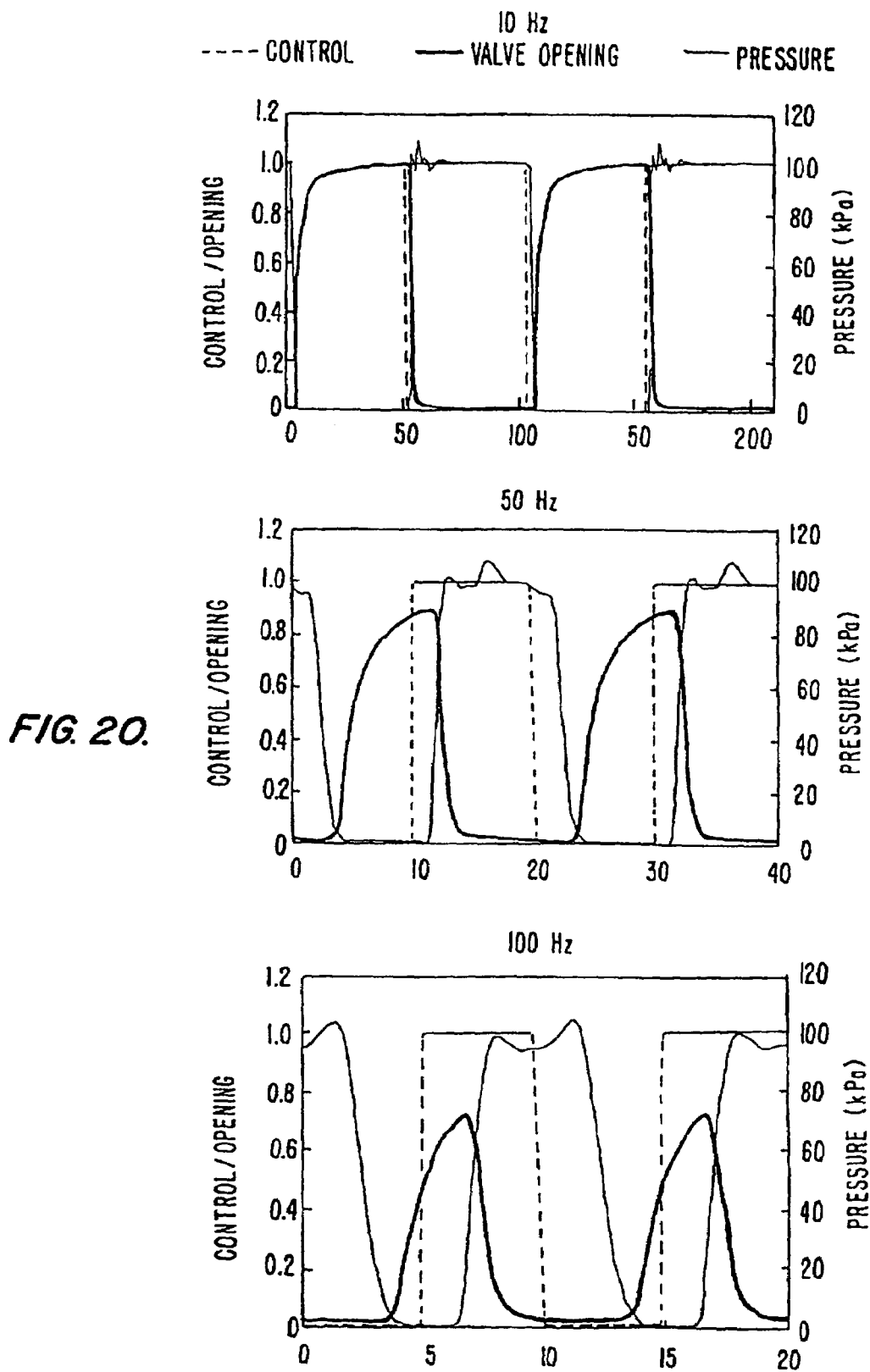
FIG. 20 illustrates time response of a 100 μm×100 μm×10 μm RTV microvalve.

Referring to FIG. 16, third elastomeric layer 50 and elastomeric structure 45 (comprising first elastomeric layer 42 and second elastomeric layer 46 bonded together) is then bonded together forming a monolithic elastomeric structure 47 having sacrificial layers 44B and 48B passing therethrough as shown. Referring to FIG. 17, sacrificial layers 44B and 48B are then removed (for example, by an solvent) such that a first flow channel 60 and a second flow channel 62 are provided in their place, passing through elastomeric structure 47 as shown. Lastly, referring to FIG. 18, planar substrate 40 can be removed from the bottom of the integrated monolithic structure.

2. Multilayer Construction

Soft lithographic bonding can be used to construct an integrated system which contains multiple flow channels. A heterogenous bonding can be used in which different layers are of different chemistries. For example, the bonding process used to bind respective elastomeric layers together can comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer can be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

A homogenous bonding can also be used in which all layers are of the same chemistry. For example, elastomeric structures are formed utilizing Sylgard 182, 184 or 186, or aliphatic urethane diacrylates such as (but not limited to) Ebecryl 270 or Irr 245 from UCB Chemical. For example, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In some applications, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Where encapsulation of sacrificial layers is employed to fabricate the elastomer structure as described above in FIGS. 8-18, bonding of successive elastomeric layers can be accomplished by pouring uncured elastomer over a previously cured elastomeric layer and any sacrificial material patterned-thereupon. Bonding between elastomer layers occurs due to interpenetration and reaction of the polymer chains of an uncured elastomer layer with the polymer chains of a cured elastomer layer. Subsequent curing of the elastomeric layer creates a bond between the elastomeric layers and create a monolithic elastomeric structure.

Referring to the first method of FIGS. 1 to 7B, first elastomeric layer 20 can be created by spin-coating an RTV mixture on microfabricated mold 12 at 2000 rpm's for 30 seconds yielding a thickness of approximately 40 microns. Second elastomeric layer 22 can be created by spin-coating an RTV mixture on microfabricated mold 11. Both layers 20 and 22 can be separately baked or cured at about 80° C. for 1.5 hours. The second elastomeric layer 22 can be bonded onto first elastomeric layer 20 at about 80° C. for about 1.5 hours.

Micromachined molds 10 and 12 can be patterned sacrificial layer on silicon wafers. In an exemplary aspect, a Shipley SJR 5740 sacrificial layer was spun at 2000 rpm patterned with a high resolution transparency film as a mask and then developed yielding an inverse channel of approximately 10 microns in height. When baked at approximately 200° C. for about 30 minutes, the sacrificial layer reflows and the inverse channels become rounded. In preferred aspects, the molds can be treated with trimethylchlorosilane (TMCS) vapor for about a minute before each use in order to prevent adhesion of silicone rubber.

3. Suitable Materials

Allcock et al, Contemporary Polymer Chemistry, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention can be fabricated from a wide variety of elastomers. For example, elastomeric layers 20, 22, 42, 46 and 50 can preferably be fabricated from silicone rubber. In some applications, microstructures of the present systems are fabricated from an elastomeric polymer such as GE RTV 615 (formulation), a vinyl-silane crosslinked (type) silicone elastomer (family). An important requirement for the preferred method of fabrication is the ability to bond multiple layers of elastomers together. In the case of multilayer soft lithography, layers of elastomer are cured separately and then bonded together. This scheme requires that cured layers possess sufficient reactivity to bond together. Either the layers can be of the same type, and are capable of bonding to themselves, or they can be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microstructures. Variations in the materials used most likely are driven by the need for particular material properties, i.e. solvent resistance, stiffness, gas permeability, or temperature stability.

Common elastomeric polymers include, but are not limited to, polyisoprene, polybutadiene, polychloroprene, polyisobutylene, poly(styrene-butadiene-styrene), the polyurethanes, and silicones. The following is a non-exclusive list of elastomeric materials which can be utilized in connection with the present invention: polyisoprene, polybutadiene, polychloroprene, polyisobutylene, poly(styrene-butadiene-s-tyrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride—hexafluoropropylene) copolymer (Viton), elastomeric compositions of polyvinylchloride (PVC), polysulfone, polycarbonate, polymethylmethacrylate (PMMA), and polytertrafluoroethylene (Teflon).

In addition, polymers incorporating materials such as chlorosilanes or methyl-, ethyl-, and phenylsilanes, and poly(dimethylsiloxane) (PDMS) such as Dow Chemical Corp. Sylgard 182, 184 or 186, or aliphatic urethane diacrylates such as (but not limited to) Ebecryl 270 or Irr 245 from UCB Chemical can also be used.

In some methods, elastomers can also be "doped" with uncrosslinkable polymer chains of the same class. For instance RTV 615 can be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "inert" polymer chains, so this is called "dilution". RTV 615 cures at up to 90% dilution, with a dramatic reduction in Young's modulus.

Other examples of doping of elastomer material can include the introduction of electrically conducting or magnetic species. Should it be desired, doping with fine particles of material having an index of refraction different than the elastomeric material (i.e. silica, diamond, sapphire) is also contemplated as a system for altering the refractive index of the material. Strongly absorbing or opaque particles can be added to render the elastomer colored or opaque to incident radiation. This can conceivably be beneficial in an optically addressable system.

C. Dimensions of the Microfabricated Structures

Some flow channels (30, 32, 60 and 62) preferably have width-to-depth ratios of about 10:1. A non-exclusive list of other ranges of width-to-depth ratios in accordance with the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 1 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels 30, 32, 60, and 62 have depths of about 1 to 100 microns. A non-exclusive list of other ranges of depths of flow channels in accordance with the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm 5 μm, 7.5 μm, 10 μm, 12.5 μm, 15 μm, 17.5 μm, 20 μm 22.5 μm, 25 μm, 30 μm, 40 μm, 50 μm, 75 μm, 100 μm, 150 μm, 200 μm, and 250 μm.

Figure 21:
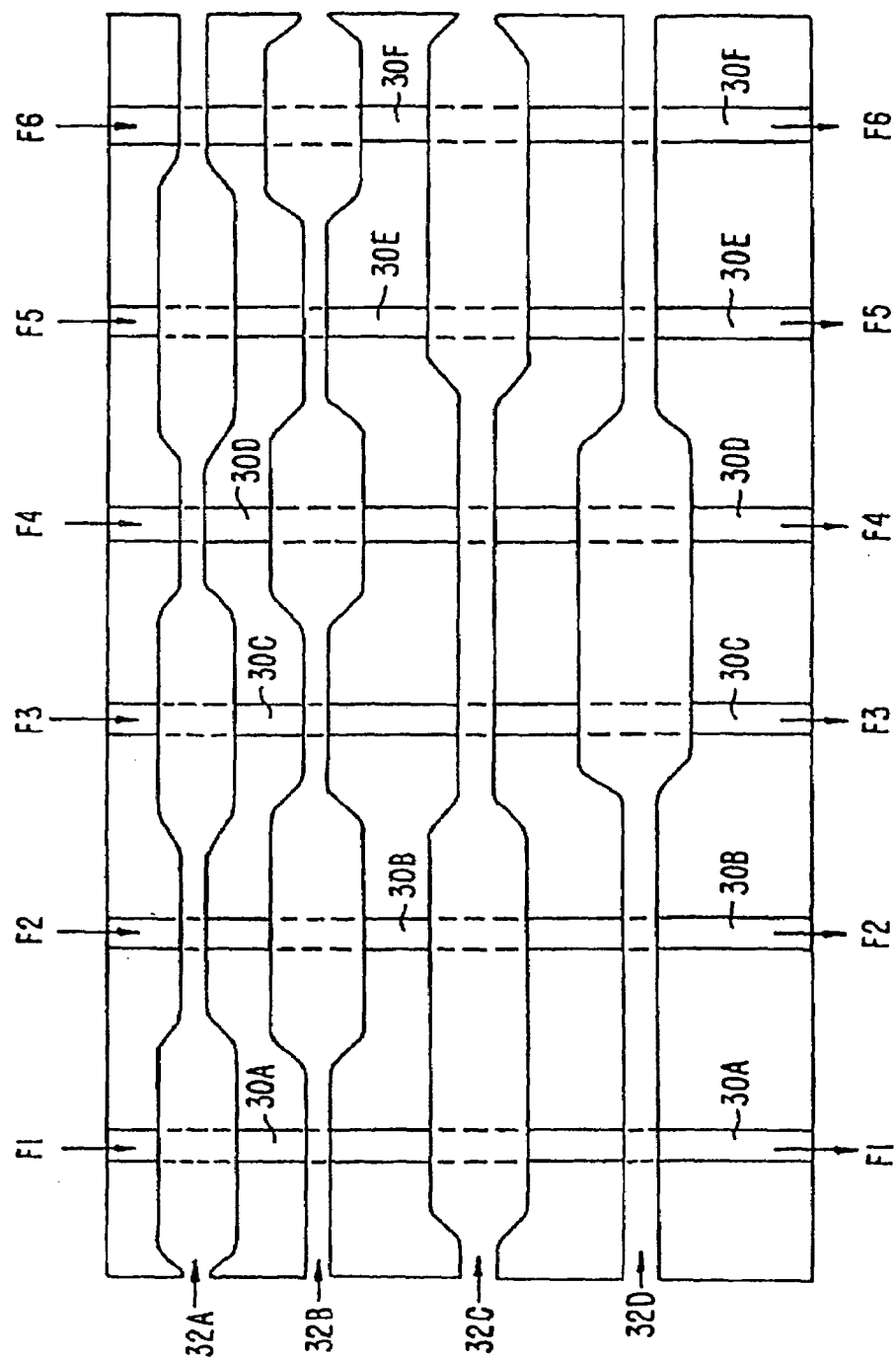
FIG. 21 is a schematic illustration of a multiplexed system adapted to permit flow through various channels.

The flow channels are not limited to these specific dimension ranges and examples given above, and can vary in width in order to affect the magnitude of force required to deflect the membrane as discussed at length below in conjunction with FIG. 21. For example, extremely narrow flow channels having a width on the order of 0.01 μm can be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

Elastomeric layer 22 can be cast thick for mechanical stability. In an exemplary embodiment, layer 22 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 µm, 0.02 µm, 0.03 µm, 0.05 µm, 0.1 µm, 0.2 µm, 0.3 µm, 0.5 µm, 1 µm, 2 µm, 3 µm, 5 µm, 7.5 µm, 10 µm, 12.5 µm, 15 µm, 17.5 µm, 20 µm, 22.5 µm, 25 µm 30 µm, 40 µm, 50 µm, 75 µm, 100 µm, 150 µm, 200 µm, 250 µm, 300 µm, 400 µm, 500 µm, 750 µm, and 1000 µm.

Similarly, first elastomeric layer 42 can have a preferred thickness about equal to that of elastomeric layer 20 or 22; second elastomeric layer 46 can have a preferred thickness about equal to that of elastomeric layer 20; and third elastomeric layer 50 can have a preferred thickness about equal to that of elastomeric layer 22.

D. Operation of the Microfabricated Components

Figure 7C:
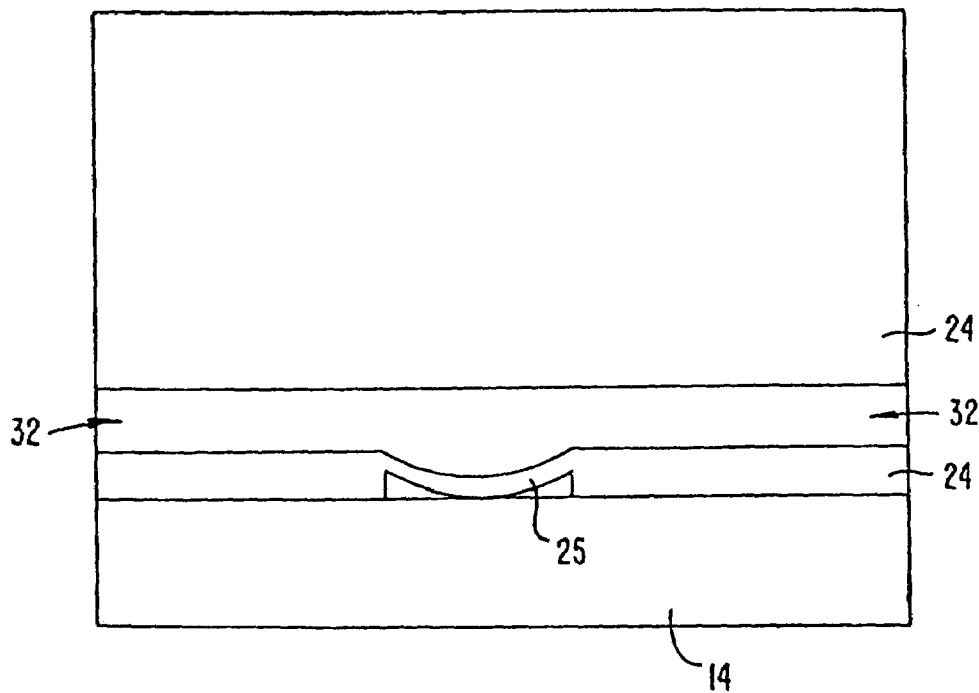
FIG. 7C corresponds to FIG. 7A, but shows a first flow channel closed by pressurization in second flow channel.

FIGS. 7B and 7C together show the closing of a first flow channel by pressurizing a second flow channel, with FIG. 7B (a front sectional view cutting through flow channel 32 in corresponding FIG. 7A), showing an open first flow channel 30; with FIG. 7C showing first flow channel 30 closed by pressurization of the second flow channel 32. Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7C, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired.

It is to be understood that exactly the same valve opening and closing methods can be achieved with flow channels 60 and 62. Since such valves are actuated by moving the roof of the channels themselves (i.e., moving membrane 25), valves and pumps produced by this technique have a truly zero dead volume, and switching valves made by this technique have a dead volume approximately equal to the active volume of the valve, for example about 100×100×10 µm=100 pL. Such dead volumes and areas consumed by the moving membrane are approximately two orders of magnitude smaller than known conventional microvalves. Smaller and larger valves and switching valves are contemplated in the present invention.

The extremely small volumes capable of being delivered by pumps and valves in accordance with the present invention represent a substantial advantage. Specifically, the smallest known volumes of fluid capable of being manually metered is around 0.1 µl. The smallest known volumes capable of being metered by automated systems is about ten-times larger (1 µl). Utilizing pumps and valves of the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

FIGS. 21a and 21b illustrate valve opening vs. applied pressure for a 100 µm wide first flow channel 30 and a 50 µm wide second flow channel 32. The membrane of this device was formed by a layer of General Electric Silicones RTV 615 having a thickness of approximately 30 µm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

The response of valves of the present invention is almost perfectly linear over a large portion of its range of travel, with minimal hysteresis. While valves and pumps do not require linear actuation to open and close, linear response does allow valves to more easily be used as metering devices. In some applications, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation can be easily determined from the pressure in the flow channel.

If actuation is linear, increased pressure in the flow channel can be countered by adding the same pressure (force per unit area) to the actuated portion of the valve.

E. Schematic Illustration of the Elastomeric Apparatuses

Figure 25:
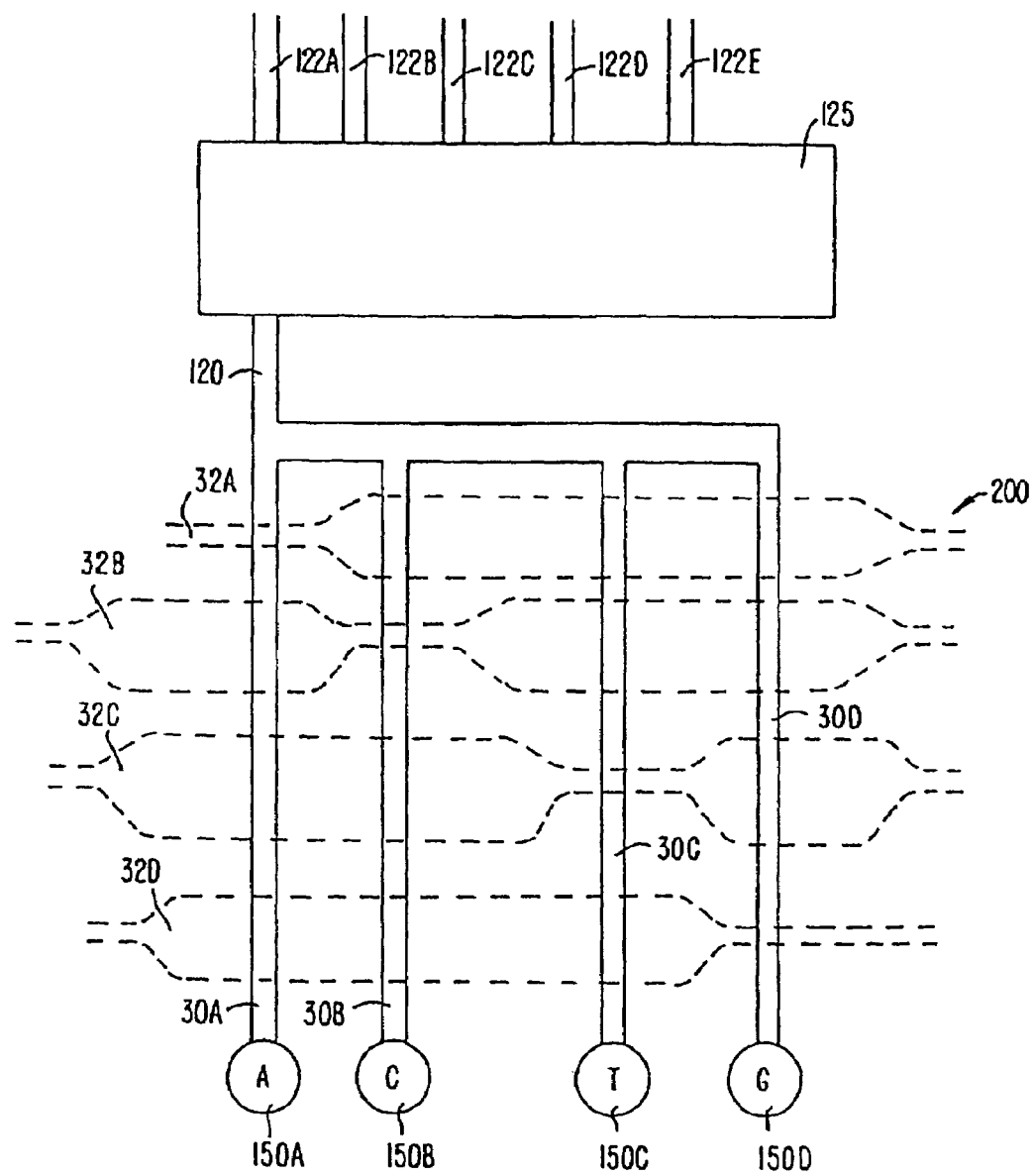
FIG. 25 is a schematic of an integrated system for analyzing polynucleotide sequences.

An exemplary sequencing system is illustrated in FIG. 25. Four reservoirs 150A, 150B, 150C and 150D have labeled nucleotides A, C, T and G respectively disposed therein. Four flow channels 30A, 30B, 30C and 30D are connected to reservoirs 150A, 150B, 150C and 150D. Four control lines 32A, 32B, 32C and 32D (shown in phantom) are disposed thereacross with control line 32A permitting flow only through flow channel 30A (i.e.: sealing flow channels 30B, 30C and 30D), when control line 32A is pressurized. Similarly, control line 32B permits flow only through flow channel 30B when pressurized. As such, the selective pressurization of control lines 32A, 32B, 32C and 32D sequentially selects a desired nucleotide (A, C, T or G) from a desired reservoir (150A, 150B, 150C or 150D). The fluid then passes through flow channel 120 into a multiplexed channel flow controller 125, which in turn directs fluid flow into one or more of a plurality of synthesis channels or reaction chambers 122A, 122B, 122C, 122D or 122E in which solid phase synthesis can be carried out.

Figure 26:
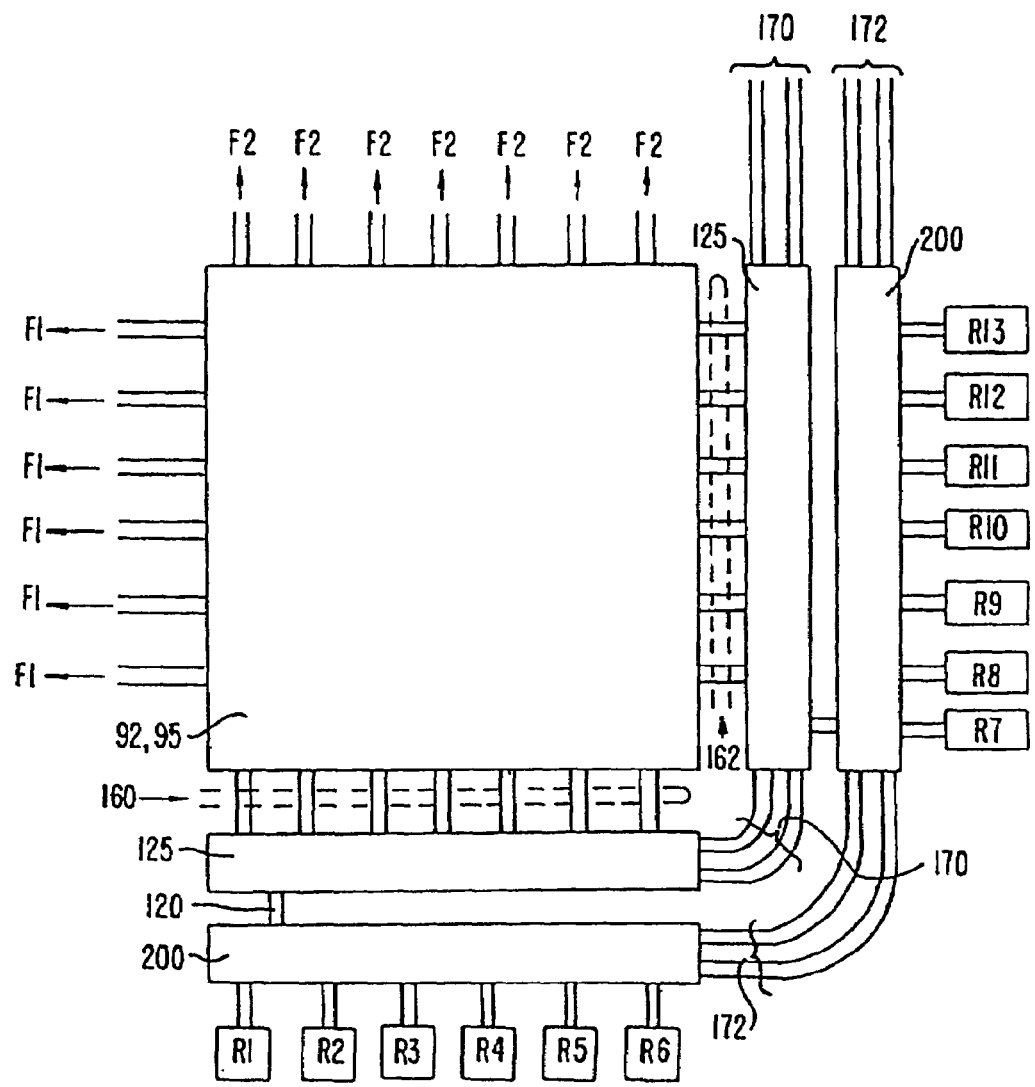
FIG. 26 is a schematic of a further integrated system for analyzing polynucleotide sequences.

FIG. 26 illustrates a further extension of the system shown in FIG. 25. It has a plurality of reservoirs R1 to R13. These reservoirs can contain the labeled nucleotides, nucleotide polymerase, or reagents for coating the surface of the synthesis channel and attaching polynucleotide templates (see below for further discussion). The reservoirs are connected to systems 200 as set forth in FIG. 25. Systems 200 are connected to a multiplexed channel flow controller 125, which is in turn connected to a plurality of synthesis channels or reaction chambers. An advantage of this system is that both of multiplexed channel flow controllers 125 and fluid selection systems 200 can be controlled by the same pressure inputs 170 and 172, provided a "close horizontal" and a "close vertical" control lines (160 and 162, in phantom) are also provided.

Some apparatuses comprise a plurality of selectively addressable reaction chambers that are disposed along a flow channel. In these apparatuses, the polynucleotide templates can be attached to the surface of the reaction chambers instead of the surface of the flow channels. An exemplary embodiment of such apparatuses is illustrated in FIGS. 22A, 22B, 22C and 22D. It is a system for selectively directing fluid flow into one or more of a plurality of reaction chambers disposed along a flow channel.

Figure 22A:
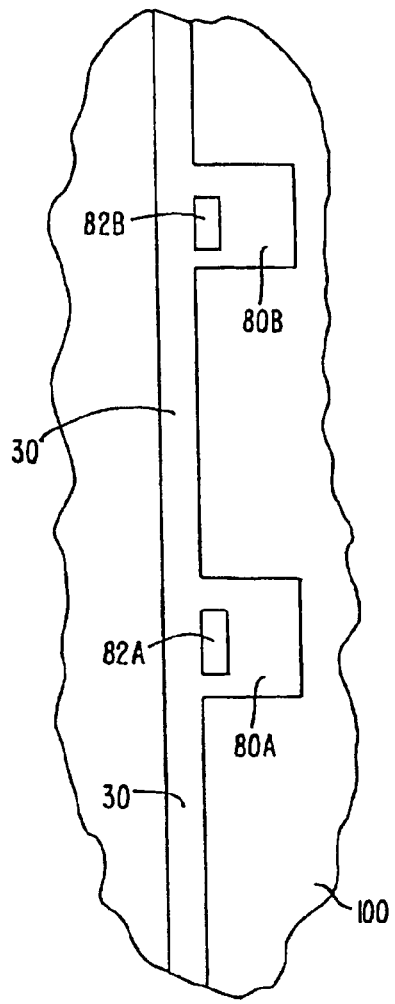
FIG. 22A is a plan view of a flow layer of an addressable reaction chamber structure.

FIG. 22A shows a top view of a flow channel 30 having a plurality of reaction chambers 80A and 80B disposed therealong. Preferably flow channel 30 and reaction chambers 80A and 80B are formed together as recesses into the bottom surface of a first layer 100 of elastomer.

Figure 22B:
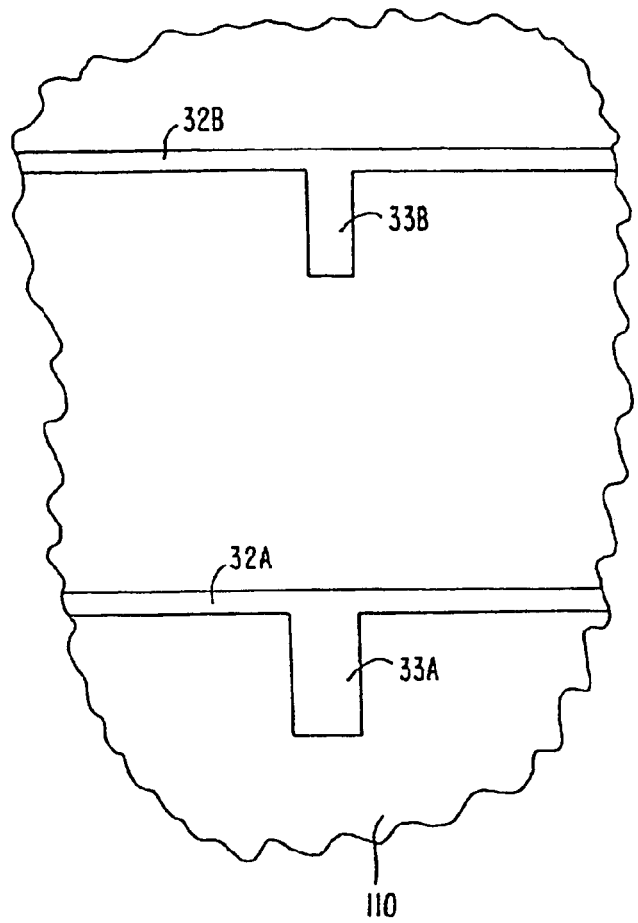
FIG. 22B is a bottom plan view of a control channel layer of an addressable reaction chamber structure.

FIG. 22B shows a bottom plan view of another elastomeric layer 110 with two control lines 32A and 32B each being generally narrow, but having wide extending portions 33A and 33B formed as recesses therein.

Figure 22C:
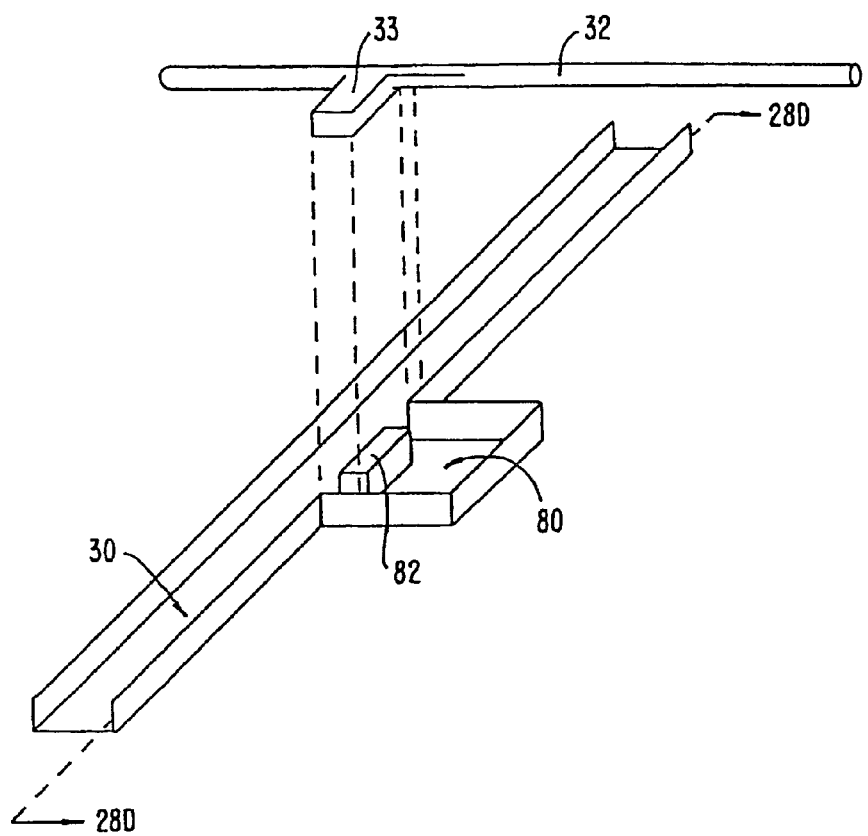
FIG. 22C is an exploded perspective view of the addressable reaction chamber structure formed by bonding the control channel layer of FIG. 22B to the top of the flow layer of FIG. 22A.

As seen in the exploded view of FIG. 22C, and assembled view of FIG. 22D, elastomeric layer 110 is placed over elastomeric layer 100. Layers 100 and 110 are then bonded together, and the integrated system operates to selectively direct fluid flow F (through flow channel 30) into either or both of reaction chambers 80A and 80B, as follows. Pressurization of control line 32A will cause the membrane 25 (i.e.: the thin portion of elastomer layer 100 located below extending portion 33A and over regions 82A of reaction chamber 80A) to become depressed, thereby shutting off fluid flow passage in regions 82A, effectively sealing reaction chamber 80 from flow channel 30. As can also be seen, extending portion 33A is wider than the remainder of control line 32A. As such, pressurization of control line 32A will not result in control line 32A sealing flow channel 30.

As can be appreciated, either or both of control lines 32A and 32B can be actuated at once. When both control lines 32A and 32B are pressurized together, sample flow channel 30 will enter neither of reaction chambers 80A or 80B.

Figure 23:
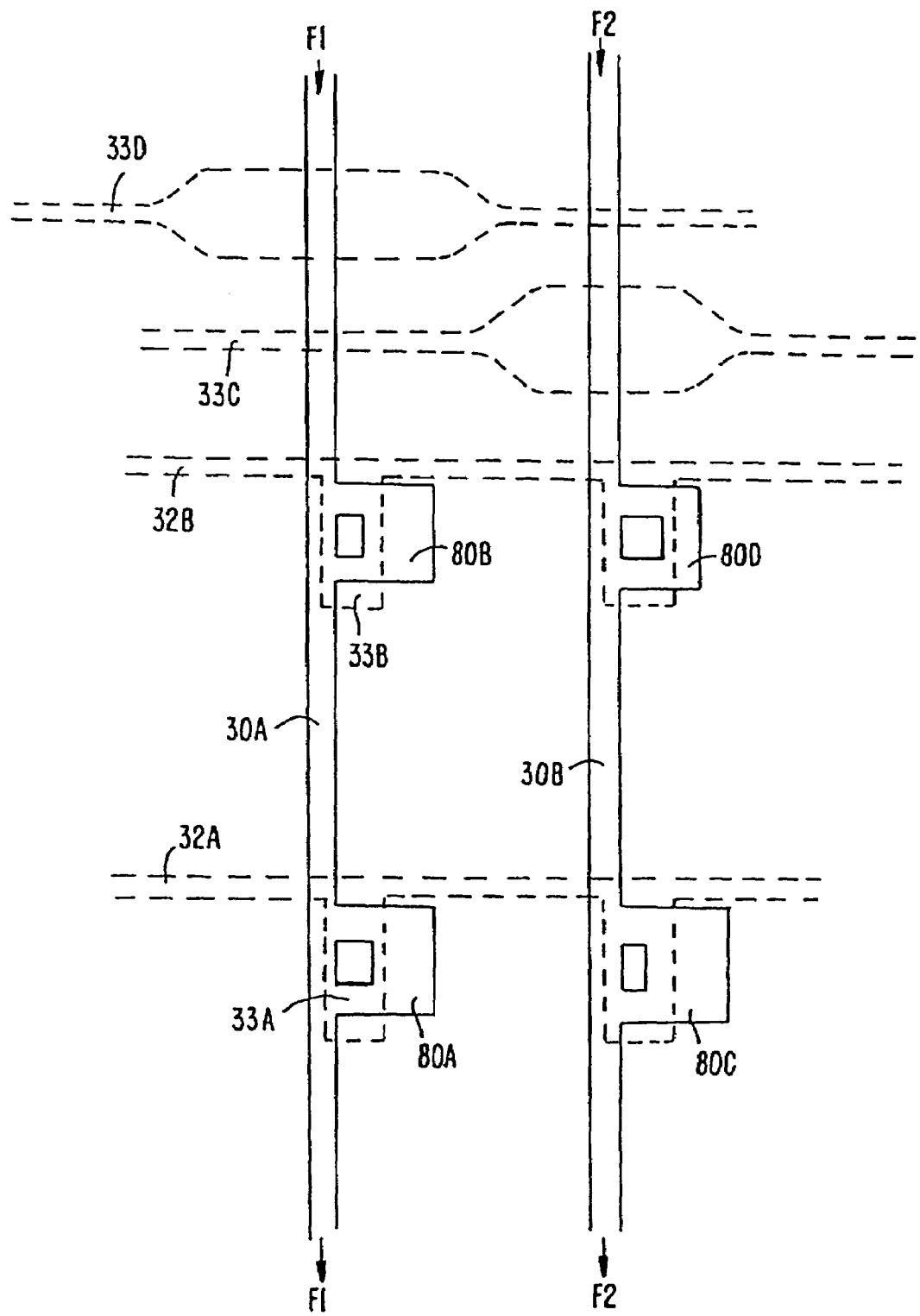
FIG. 23 is a schematic of a system adapted to selectively direct fluid flow into any of an array of reaction wells.

The concept of selectably controlling fluid introduction into various addressable reaction chambers disposed along a flow line (FIG. 22) can be combined with concept of selectably controlling fluid flow through one or more of a plurality of parallel flow lines (FIG. 21) to yield a system in which a fluid sample or samples can be sent to any particular reaction chamber in an array of reaction chambers. An example of such a system is provided in FIG. 23, in which parallel control channels 32A, 32B and 32C with extending portions 34 (all shown in phantom) selectively direct fluid flows F1 and F2 into any of the array of reaction wells 80A, 80B, 80C or 80D as explained above; while pressurization of control lines 32C and 32D selectively shuts off flows F2 and F1, respectively.

Figure 24:
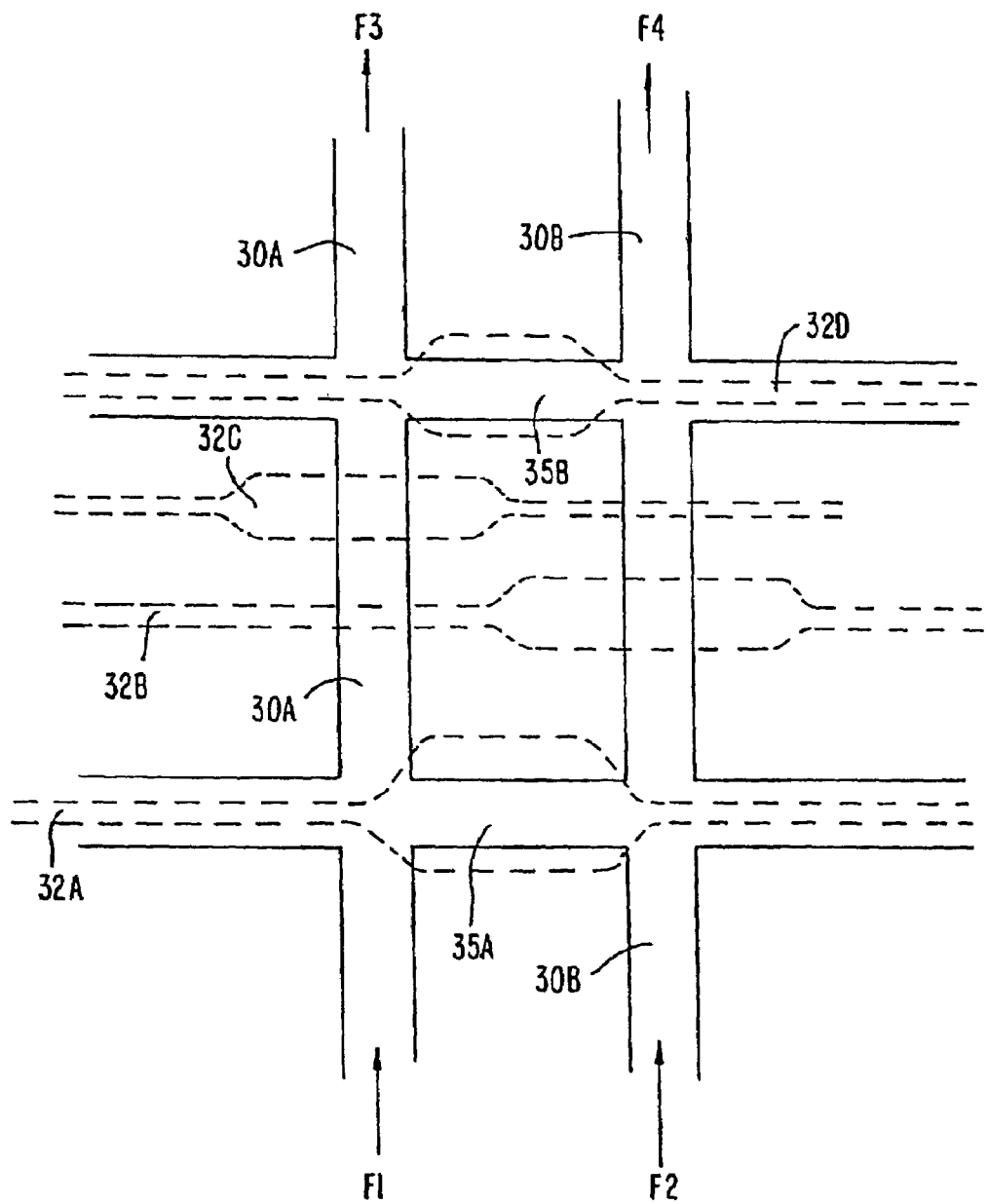
FIG. 24 is a schematic of a system adapted for selectable lateral flow between parallel flow channels.

In yet another embodiment, fluid passage between parallel flow channels is possible. Referring to FIG. 24, either or both of control lines 32A or 32D can be depressurized such that fluid flow through lateral passageways 35 (between parallel flow channels 30A and 30B) is permitted. In this aspect of the invention, pressurization of control lines 32C and 32D would shut flow channel 30A between 35A and 35B, and would also shut lateral passageways 35B. As such, flow entering as flow F1 would sequentially travel through 30A, 35A and leave 30B as flow F4.

F. Non-elastomer Based Apparatuses

As discussed above, while elastomers are preferred materials for fabricating the sequencing apparatuses of the present invention, non-elastomer based microfluidic devices can also be used in the apparatuses of the present invention. In some applications, the sequencing apparatuses utilize microfluidics based on conventional micro-electro-mechanical system (MEMS) technology. Methods of producing conventional MEMS microfluidic systems such as bulk micro-machining and surface micro-machining have been described, e.g., in Terry et al., A Gas Chromatographic Air Analyzer Fabricated on a Silicon Wafer, IEEE Trans. on Electron Devices, v. ED-26, pp. 1880-1886, 1979; and Berg et al., Micro Total Analysis Systems, New York, Kluwer, 1994.

Bulk micro-machining is a subtractive fabrication method whereby single crystal silicon is lithographically patterned and then etched to form three-dimensional structures. For example, bulk micromachining technology, which includes the use of glass wafer processing, silicon-to-glass wafer bonding, has been commonly used to fabricate individual microfluidic components. This glass-bonding technology has also been used to fabricate microfluidic systems.

Surface micro-machining is an additive method where layers of semiconductor-type materials such as polysilicon, silicon nitride, silicon dioxide, and various metals are sequentially added and patterned to make three-dimensional structures. Surface micromachining technology can be used to fabricate individual fluidic components as well as microfluidic systems with on-chip electronics. In addition unlike bonded-type devices, hermetic channels can be built in a relatively simple manner using channel walls made of polysilicon (see, e.g., Webster et al., Monolithic Capillary Gel Electrophoresis Stage with On-Chip Detector, in International Conference on Micro Electromechanical Systems, MEMS 96, pp. 491-496, 1996), silicon nitride (see, e.g., Mastrangelo et al., Vacuum-Sealed Silicon Micromachined Incandescent Light Source, in Intl. Electron Devices Meeting, IDEM 89, pp. 503-506, 1989), and silicon dioxide.

In some applications, electrokinetic flow based microfluidics can be employed in the sequencing apparatuses of the present invention. Briefly, these systems direct reagents flow within an interconnected channel and/or chamber containing structure through the application of electrical fields to the reagents. The electrokinetic systems concomitantly regulate voltage gradients applied across at least two intersecting channels. Such systems are described, e.g., in WO 96/04547 and U.S. Pat. No. 6,107,044.

An exemplary electrokinetic flow based microfluidic device can have a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection.

In some electrokinetic flow based apparatuses, at least three intersecting channels having at least four unintersected termini are present. In a basic cross channel structure, where a single horizontal channel is intersected and crossed by a single vertical channel, controlled electrokinetic transport operates to direct reagent flow through the intersection, by providing constraining flows from the other channels at the intersection. Simple electrokinetic flow of this reagent across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage).

Figure 27:
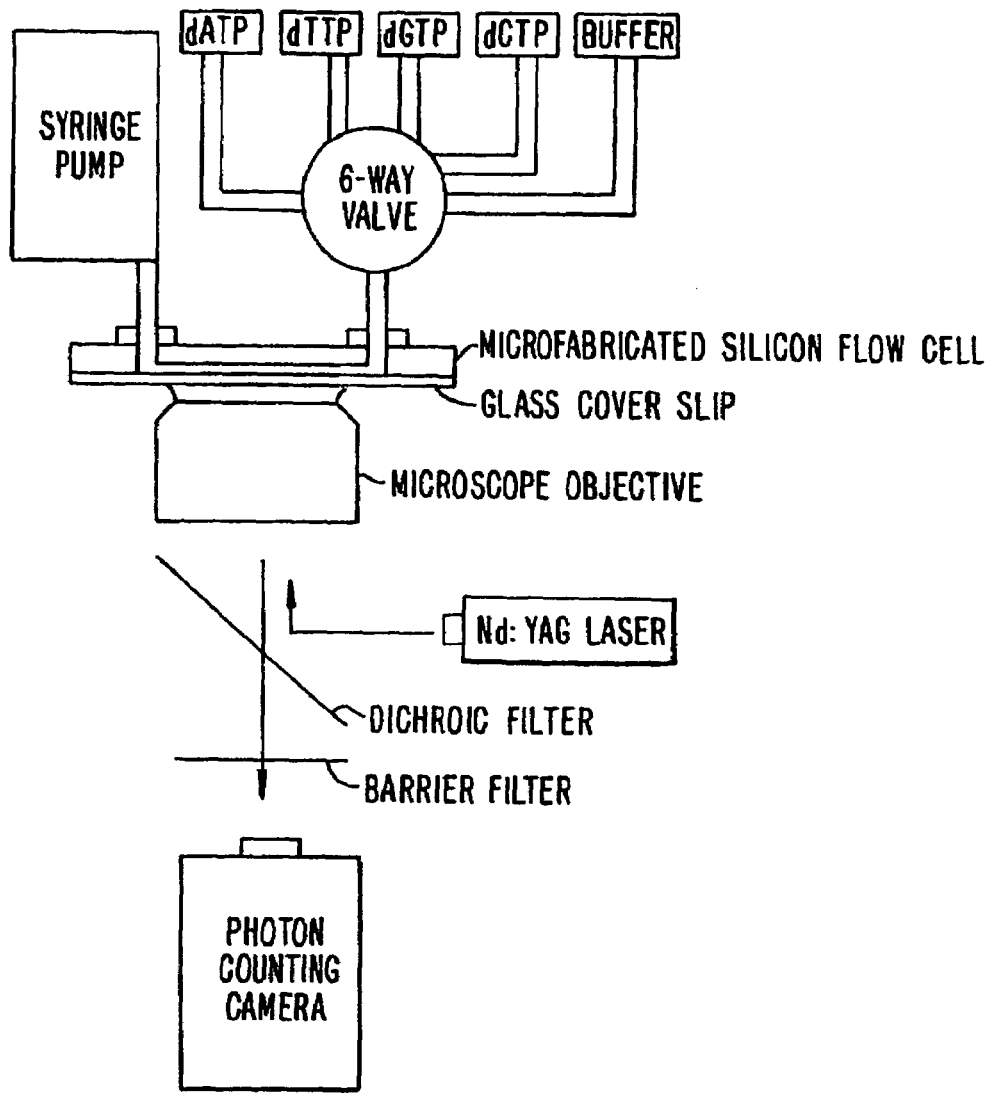
FIG. 27 is a schematic diagram of a sequencing apparatus.

In some other applications, the apparatus comprises a microfabricated flow cell with external mini-fluidics. Such an apparatus is illustrated in FIG. 27. The glass cover slip can be anodically bonded to the surface of the flow cell. The interrogation region is 100 μm×100 μm×100 μm, while the input and output channels are 100 μm×100 μm×100 μm. Holes for the attachment of plumbing are etched at the ends of the channels. For such apparatuses, the fluidics can be external. Plumbing can be performed with standard HPLC components, e.g., from Upchurch and Hamilton. In the interrogation region, the polynucleotide template is attached to the surface with standard avidin-biotin chemistry. Multiple copies of templates can be attached to the apparatus. For example, for a 7 kb template, the radius of gyration is approximately 0.2 μm. Therefore, about $10^5$ molecules can be attached while preventing the molecules from touching. Reagent switching can be accomplished with, e.g., an Upchurch six port injection valve and driven by, e.g., a Thar Designs motor. Fluid can be pumped with a syringe pump. The detection system can be an external optical microscope, with the objective being in close proximity to the glass cover slip.

III. Analysis of Polynucleotide Sequences

A. Template Preparation and Attachment to Surface of Synthesis Channel

1. The General Scheme

In some applications, the polynucleotides to be analyzed are first cloned in single-stranded M13 plasmid (see, e.g., Current Protocols In Molecular Biology, Ausubel, et al., eds., John Wiley & Sons, Inc. 1995; and Sambrook, et al., Molecular Cloning. A Laboratory Manual, Cold Spring Harbor Press, 1989). The single stranded plasmid is primed by 5'-biotinylated primers (see, e.g., U.S. Pat. No. 5,484,701), and double stranded plasmid can then be synthesized. The double stranded circle is then linearized, and the biotinylated strand is purified. In some methods, templates of around 100 bp in length are analyzed. In some methods, templates to be sequenced are about 1 kb in length. In other methods, templates that can be analyzed have a length of about 3 kb, 10 kb, or 20 kb.

Primer annealing is performed under conditions which are stringent enough to achieve sequence specificity yet sufficiently permissive to allow formation of stable hybrids at an acceptable rate. The temperature and length of time required for primer annealing depend upon several factors including the base composition, length and concentration of the primer, and the nature of the solvent used, e.g., the concentration of DMSO, formamide, or glycerol, and counter ions such as magnesium. Typically, hybridization with synthetic polynucleotides is carried out at a temperature that is approximately 5 to 10° C. below the melting temperature of the target-primer hybrid in the annealing solvent. Preferably, the annealing temperature is in the range of 55 to 75° C. and the primer concentration is approximately 0.2 μM. Under these preferred conditions, the annealing reaction can be complete in only a few seconds.

The single stranded polynucleotide templates to be analyzed can be DNA or RNA. They can comprise naturally occurring and or non-naturally occurring nucleotides. Templates suitable for analysis according to the present invention can have various sizes. For example, the template can have a length of 100 bp, 200 bp, 500 bp, 1 kb, 3 kb, 10 kb, or 20 kb. In other embodiments, methods and devices of the invention are useful in analyzing specific nucleotide variations, such a allelic variations, mutations and single-nucleotide polymorphisms (SNPs).

In some methods, the templates are immobilized to the surface of the synthesis channels (e.g., 122A-122E in FIG. 25). By immobilizing the templates, unincorporated nucleotides can be removed from the synthesis channels by a washing step. The templates can be immobilized to the surface prior to hybridization to the primer. The templates can also be hybridized to the primers first and then immobilize to the surface. Alternatively, the primers are immobilized to the surface, and the templates are attached to the synthesis channels through hybridization to the primers.

Various methods can be used to immobilize the templates or the primers to the surface of the synthesis channels or reaction chambers. The immobilization can be achieved through direct or indirect bonding of the templates to the surface. The bonding can be by covalent linkage. See, Joos et al., Analytical Biochemistry 247:96-101, 1997; Oroskar et al., Clin. Chem 42:1547-1555, 1996; and Khandjian, Mole. Bio. Rep. 11: 107-115, 1986. The bonding can also be through non-covalent linkage. For example, Biotin-streptavidin (Taylor et al., J. Phys. D. Appl. Phys. 24:1443, 1991) and digoxigenin and anti-digoxigenin (Smith et al., Science 253: 1122, 1992) are common tools for attaching polynucleotides to surfaces and parallels. Alternatively, the bonding can be achieved by anchoring a hydrophobic chain into a lipidic monolayer or bilayer.

When biotin-streptavidin linkage is used to immobilize the templates, the templates are biotinylated, and one surface of the synthesis channels are coated with streptavidin. Since streptavidin is a tetramer, it has four biotin binding sites per molecule. Thus, in order to coat a surface with streptavidin, the surface can be biotinylated first, and then one of the four binding sites of streptavidin can be used to anchor the protein to the surface, leaving the other sites free to bind the biotinylated template (see, Taylor et al., J. Phys. D. Appl. Phys. 24:1443, 1991). Such treatment leads to a high density of streptavidin on the surface of the synthesis channel, allowing a correspondingly high density of template coverage. Reagents for biotinylating a surface can be obtained, for example, from Vector laboratories.

In some applications, the substrate or synthesis channel is pretreated to create surface chemistry that facilitates attachment of the polynucleotide templates and subsequent synthesis reactions. In some methods, the surface is coated with a polyelectrolyte multilayer (PEM). Attachment of templates to PEM-coated surface can be accomplished by light-directed spatial attachment (see, e.g., U.S. Pat. Nos. 5,599,695, 5,831, 070, and 5,959,837). Alternatively, the templates can be attached to PEM-coated surface entire chemically (see below for detail). In some methods, non-PEM based surface chemistry can be created prior to template attachment.

2. Attachment of Diverse Templates to a Single Channel

While diverse polynucleotide templates can be each immobilized to and sequenced in a separate synthesis channel, multiple templates can also be sequenced in a single microfluidic synthesis channel. In the latter scenario, the templates are attached at different locations along the flow path of the channel. This can be accomplished by a variety of different methods, including hybridization of primer capture sequences to oligonucleotides immobilized at different points on the substrate, and sequential activation of different points down the channel towards template immobilization.

Methods of creation of surfaces with arrays of oligonucleotides have been described, e.g., in U.S. Pat. Nos. 5,744,305, 5,837,832, and 6,077,674. Such a surface can be used as a substrate that is to be bond to a microfluidic chip and form the synthesis channel. Primers with two domains, a priming domain and a capture domain, can be used to anchor templates to the substrate. The priming domain is complementary to the target template. The capture domain is present on the non-extended side of the priming sequence. It is not complementary to the target template, but rather to a specific oligonucleotide sequence present on the substrate. The target templates can be separately hybridized with their primers, or (if the priming sequences are different) simultaneously hybridized in the same solution. Incubation of the primer/template duplexes in the flow channel under hybridization conditions allows attachment of each template to a unique spot. Multiple synthesis channels can be charged with templates in this fashion simultaneously.

Another method for attaching multiple templates in a single channel is to sequentially activate portions of the substrate and attach template to them. Activation of the substrate can be achieved by either optical or electrical means. Optical illumination can be used to initiate a photochemical deprotection reaction that allows attachment of the template to the surface (see eg., U.S. Pat. Nos. 5,599,695, 5,831,070, and 5,959,837) For instance, the substrate surface can be derivatized with "caged biotin", a commercially available derivative of biotin that becomes capable of binding to avidin only after being exposed to light. Templates can then be attached by exposure of a site to light, filling the channel with avidin solution, washing, and then flowing biotinylated template into the channel. Another variation is to prepare avidinylated substrate and a template with a primer with a caged biotin moiety; the template can then be immobilized by flowing into the channel and illumination of the solution above a desired area. Activated template/primer duplexes are then attached to the first wall they diffused to, yielding a diffusion limited spot.

Electrical means can also be used to direct template to specific points in the channel. By positively charging one electrode in the channel and negatively charging the others, a field gradient can be created which drives the template to a single electrode, where it can attach (see, e.g., U.S. Pat. Nos. 5,632,957, 6,051,380, and 6,071,394). Alternatively, it can be achieved by electrochemically activating regions of the surface and changing the voltage applied to the electrodes.

3. Channel Coatings

In certain methods, the synthesis channels are coated or treated with various agents to enhance certain aspects of the assay. For example, depending upon the nature of the material from which the channels are formed, it can be useful to coat the channels with an agent that protects against or prevents components of the assay (for example cells, proteins, peptides, substrates, small molecules) from adhering to the walls of the channels or to the sides of the wells through which these agents are introduced into the device. One function of these coatings is to help ensure the biological integrity of the introduced sample. Another function is to prevent physical interactions between cells and the walls of the channel that might affect cellular responses or functions in undesired ways. Examples of suitable coating agents include, but are not limited to, poly(ethylene glycol) (PEG), diacrylated poly(ethylene glycol) (DAPEG), TEFLON, parylene, acrylamides, silanes, and other agents to form self assembled monolayers.

Similarly channels can be modified with a variety of agents to achieve other purposes such as separation and sorting functions, with the goal being to prepare the flow channels in accordance with the particular application being conducted. More specifically, by properly selecting the bulk matrix of the flow channel (i.e., the particular choice of elastomers to utilize in constructing the flow channels), surface chemistry (i.e., modification of the properties of microchannels created within the elastomer) and the specific modification of regions of the elastomer surface (e.g., by covalent and/or non-covalent attachment of proteins, peptides, nucleic acids (or their analogs), lipids, carbohydrates) can facilitate the "tuning" of the device to a given application or combination of applications. Methods for modification of elastomer surfaces include, but are not limited to: (1) copolymerization with functional groups during elastomer curing (an example of bulk modification), (2) oxygen plasma treatment (3) modification of plasma treated surfaces with silanizing reagents (e.g., 3-aminopropyltriethoxysi-lane, N-(2-aminoethyl)-3-aminopropyltrimethoxysilane, dimethylchlorosilane or hexamethyldisilazane) which form self-assembled monolayers on the elastomer surface (which can be used to treat individual flow channels), (4) use of photochemical crosslinking reagents to create patterns of reactive groups on the elastomer surface (e.g., aryl azide derivatives or quinone-based derivatives), (5) passive modification of the elastomer surface by adsorption.

Adsorption also enables one to create secondary or tertiary layers of modification that offer improved properties over primary adsorption. As a specific example, one can use antibodies against an antigen to create a primary, coating of channel walls. If antigen is then bound to the bound antibody, one can then create a secondary layer of specifically bound antigen. Antigen bound in this way can be "presented" to the interior of the flow channel in a more appropriate way than as a passively adsorbed primary layer. Schemes for creating a plurality of layers composed of proteins, nucleic acids, lipids or carbohydrates or combinations thereof will be apparent to the skilled practitioner.

Channels can also be coated with materials that specifically bind to assay components and/or reaction products such as products produced by a cell or during an enzymatic assay, for instance. One example of such a coating is one in which the channel is coated with a metal or a metal-derivatized material. Reaction products bearing a metal chelate tag thus become bound to the metal-coated wall or material. Of course, a wide variety of other binding pairs could also be utilized as substitutes for the metal chelating agent and metal. Assays utilizing such metal-derivatized materials is discussed in greater detail infra on the section on enzymatic assays (see also U.S. Pat. No. 6,146,842).

4. Exemplary Surface Chemistry for Attaching Templates: PEM Coating

In some methods, the surface of synthesis channels are coated with PEM prior to attachment of the templates (or primers). A PEM coating may be used alternatively or in addition to other substrate coatings. For example, a substrate may comprise or be coated with poly(dimethylsiloxane), further coated with poly(ethylene glycol), and yet further coated with PEM. Such attachment scheme can be both an ex-situ process or an in situ process. With the ex-situ protocol, the surface of the flat substrate is coated with PEM first, followed by attachment of the templates. The elastomeric microfluidic chip is then bonded to the substrate to form and seal the synthesis channel. With the in-situ protocol, the microfluidic chip is attached to the flat substrate first, and a PEM is then constructed in the channels. The templates are then attached inside the channels. In still some other applications, the microfluidic chip can be bonded to the flat substrate at any point in the template attachment process, and the remaining steps can be completed inside the microfluidic channels.

Preferably, the in-situ protocol is used. The method described here leads to low nonspecific binding of labeled (e.g., with fluorescent dye) nucleotides and good seal of the microfluidic components and the synthesis channels. A good seal between the microfluidic components and the synthesis channels allows the use of higher pressures, which in turn increases flow rates and decreases exchange times. The various methods for attaching the templates to the surface of the synthesis channel are discussed in detail below.

An exemplified scheme of the ex situ protocol is as follows. First, the surface of a glass cover slip is cleaned and then coated with a polyelectrolyte multilayer (PEM). Following biotinylation of the carboxylic acid groups, streptavidin is then applied to generate a surface capable of capturing biotinylated molecules. Biotinylated polynucleotide templates are then added to the coated glass cover slip for attachment. The surface chemistry thus created is particularly suited for sequencing by synthesis with fluorescent nucleotides, because it generates a strong negatively-charged surface which repels the negatively-charged nucleotides. Detailed procedures for cleaning the cover slips, coating of polyelectrolyte multilayer, and attachment of the templates are described below.

Figure 28:
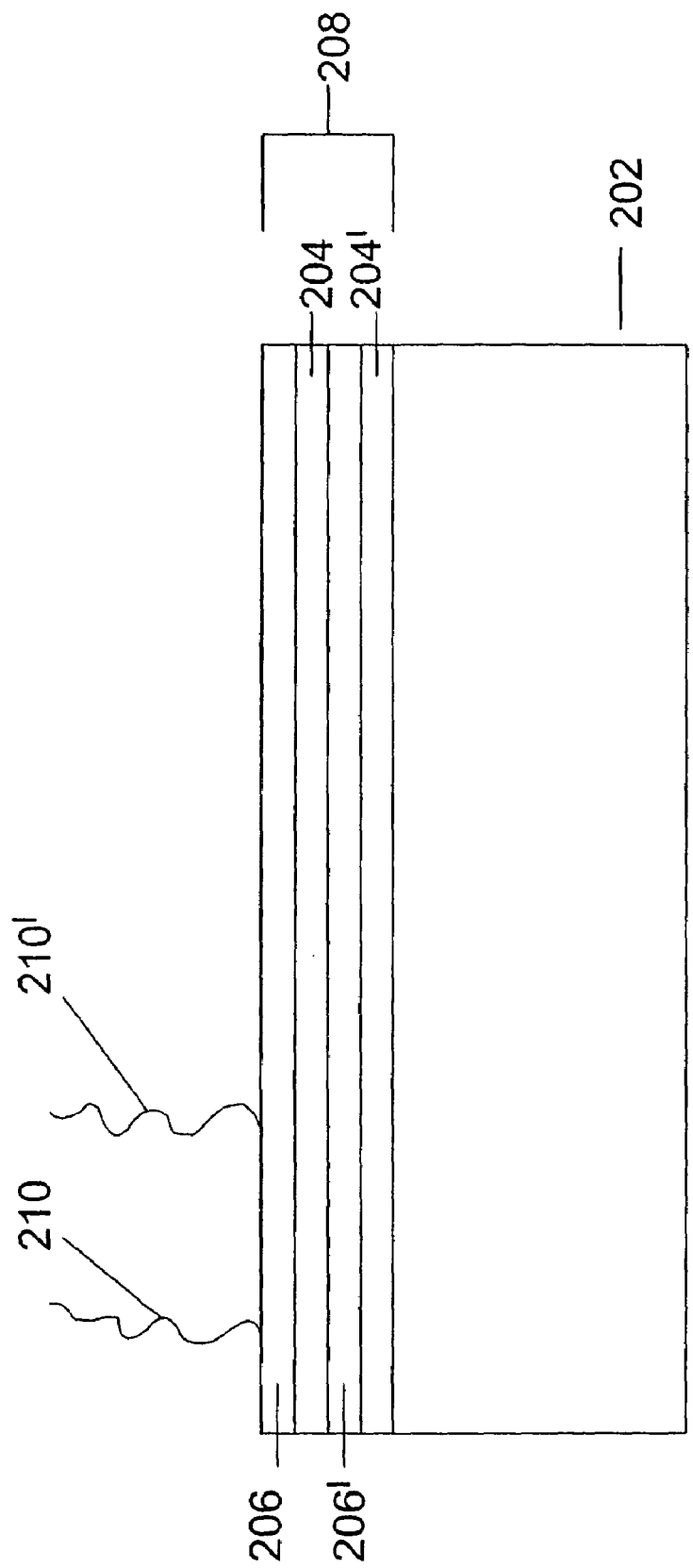
FIG. 28 is an embodiment of a polyelectrolyte multilayer having polynucleotides attached thereto.

PEM formation proceeds by the sequential addition of polycations and polyanions, which are polymers with many positive or negative charges, respectively. Upon addition of a polycation to a negatively-charged surface, the polycation deposits on the surface (FIG. 28, 202), forming a thin polymer layer (FIGS. 28, 204 and 204') and reversing the surface charge. Similarly, a polyanion deposited on a positively charged surface forms a thin layer of polymer (FIGS. 28, 206 and 206') and leaves a negatively charged surface. Alternating exposure to the poly(+) and poly(−) generates a polyelectrolyte multilayer structure (FIG. 28, 208) with a surface charge determined by the last polyelectrolyte added; in the case of incompletely-charged surfaces, multiple-layer deposition also tends to increase surface charge to a well defined and stable level. PEM formation has been described by Decher et al. (Thin Solid Films, 210:831-835, 1992)".

Carboxylic acid groups are negatively charged at pH 7, and are a common target for covalent bond formation. By terminating the surface with carboxylic acid groups, a surface which is both strongly negatively-charged and chemically reactive can be generated. In particular, amines can link to them to form amide bonds, a reaction that can be catalyzed by carbodiimides. A molecule with biotin at one end, a hydrophilic spacer, and an amine at the other end is used to terminate the surface with biotin.

An avidin molecule is capable of binding up to four biotin molecules. This means that avidin, and its derivative Streptavidin, is capable of converting a biotin-terminated surface to a surface capable of capturing biotin. Streptavidin, which carries a slight negative charge, is used to attached the polynucleotide templates (FIGS. 28, 210 and 210') to be analyzed to the surface by using a biotinylated primer. A buffer with a high concentration of multivalent salt is used in order to screen the repulsion of the negatively charged surface for the negatively-charged DNA.

To coat the polyelectrolyte multilayer, the glass cover slips are first cleaned with HP $H_2O$ ($H_2O$ deionized to 18.3 MOhm-cm and filtered to 0.2 μm) and a RCA Solution (6:4:1 mixture of HP $H_2O$, (30% $NH_4OH$), and (30% $H_2O_2$)). The cover slips are then sonicated in 2% Micro 90 detergent for 20 minutes. After rinsing thoroughly with HP $H_2O$, the cover slips are stirred in gently boiling RCA solution for at least 1 hour, and rinsed again with HP $H_2O$.

After cleaning, the glass cover slips are submerged in PAII solution (Poly(allylamine) (PAII, +): 2 mg/ml in HP $H_2O$, adjusted to pH 7.0) and agitate for at least 10 minutes. The cover slips are then removed from PAII and washed with HP $H_2O$ by submerging in HP $H_2O$ with agitation for at least three times. The treatment continues by agitation in a PAcr solution (Poly(acrylic acid) (PAcr, −): 2 mg/ml in HP $H_2O$, adjusted to pH 7.0) for at least 10 minutes and washing with HP $H_2O$. The treatment steps are then repeated once.

After PEM coating, the PEM coated glass is incubated with a EDC/BLCPA solution for 30 minutes. The EDC/BLCPA solution is prepared by mixing equal amounts of 50 mM EDC solution (in MES buffer) and 50 mM BLCPA (in MES buffer) and diluting to 5 mM in MES buffer. The glass is then rinsed with 10 mM Tris-NaCl and incubated with 0.1 mg/ml streptavidin solution for 1 hour. After washing with 10 mM Tris-NaCl, the glass is incubated with a solution containing the polynucleotide template ($10^{-7}$ M in Tris 100 mM $MgCl_2$) for 30 minutes. The glass is again rinsed thoroughly with 10 mM Tris-NaCl.

For in-situ attachment, the microfluidic substrate is bonded to the glass cover slip by HCl-assisted bonding. Essentially, the chips are first washed with a surfactant (e.g., first with HP $H_2O$, then in 0.1% Tween 20, then rinse again with HP $H_2O$). The washed microfluidic chips are then put on the glass cover slips with a few microliters of dilute HCl (e.g., 1% HCl in HP $H_2O$), followed by baking at 37° C. for 1-2 hours. Such treatment enhances the bond strength to glass (e.g., >20 psi pressure) without increasing nonspecific adsorption.

Following HCl treatment, PEM formation, biotinylation, streptavidinylation, and template attachment can be performed using essentially the same reagents and methods as described above for ex-situ attachment, except the solutions are injected through the channels by pressure instead of just being aliquoted onto the substrate surface.

Coating the microchannel surface with the PEM technique is significant for analyzing polynucleotide sequences according to the present invention. In general, the method used to attach the template to the surface should fulfill several requirements in order to be useful in a sequencing-by-synthesis application. First, it must be possible to attach reasonable quantities of polynucleotide templates. In addition, the attached templates should remain active for polymerase action. Further, nonspecific binding of fluorescent nucleotides should be very low.

If insufficient numbers of template molecules are bound, the signal-to-noise ratio of the technique is too low to allow useful sequencing. Binding large quantities of templates is insufficient, however, if the primer/target duplex cannot be extended by a polymerase. This is a problem for surface chemistry based on building off amine-bearing surfaces: amines are positively charged at normal pH. This means that the negatively-charged DNA backbone can non-specifically stick to the surface, and that the polymerase is sterically impeded from adding nucleotides. Finally, if there is significant nonspecific binding of fluorescent nucleotides to the surface, it becomes impossible to distinguish between signal due to incorporation and signal due to nonspecific binding.

When the nucleotides are fluorescently labeled, they generally have relatively strong nonspecific binding to many surfaces because they possess both a strongly polar moiety (the nucleotide, and in particular the triphosphate) and a relatively hydrophobic moiety (the fluorescent dye). A surface bearing positively-charged groups (i.e. amines) invariably has a very high nonspecific binding due to the attraction of the triphosphate group (which is strongly negatively charged) to the positively-charged amines. Neutral surfaces generally have strong nonspecific binding due to the action of the fluorescent nucleotide as a surfactant (i.e. assembling with nonpolar moiety towards the uncharged (more hydrophobic) surface and polar end in the aqueous phase). A surface bearing negative charges can repel the negatively charged fluorescent nucleotides, so it has the lowest nonspecific binding. Glass is such a surface, but the surface silanols that give it its negative charge in water are a difficult target to attach DNA to directly. Typical DNA attachment protocols use silanization (often with aminosilanes) to attach template; as discussed earlier amino groups lead to unacceptable levels of nonspecific binding.

A polyelectrolyte multilayer terminated with carboxylic acid-bearing polymer fulfills all three criteria. First, it is easy to attach polynucleotide to because carboxylic acids are good targets for covalent bond formation. Second, the attached template is active for extension by polymerases—most probably, the repulsion of like charges prevents the template from "laying down" on the surface. Finally, the negative charge repels the fluorescent nucleotides, and nonspecific binding is low.

The attachment scheme described here is easy to generalize on. Without modification, the PEM/biotin/streptavidin surface that is produced can be used to capture or immobilize any biotinylated molecule. A slight modification can be the use of another capture pair, i.e. substituting digoxygenin (dig) for biotin and labeling the molecule to be immobilized with anti-digoxygenin (anti-dig). Reagents for biotinylation or dig-labeling of amines are all commercially available.

Another generalization is that the chemistry is nearly independent of the surface chemistry of the support. Glass, for instance, can support PEMs terminated with either positive or negative polymer, and a wide variety of chemistry for either. But other substrates such as silicone, polystyrene, polycarbonate, etc, which are not as strongly charged as glass, can still support PEMs. The charge of the final layer of PEMs on weakly-charged surfaces becomes as high as that of PEMs on strongly-charged surfaces, as long as the PEM has sufficiently-many layers. For example, PEM formation on $O_2$-plasma treated silicone rubber has been demonstrated by the present inventors. This means that all the advantages of the glass/PEM/biotin/Streptavidin/biotin-DNA surface chemistry can be applied to other substrates.

Although the above discussion describes the immobilization of polynucleotide templates by attachment to the surface of flow channels or the surface of reaction chambers disposed along flow channels, other methods of template immobilization can also be employed in the methods of the present invention. In some methods, the templates can be attached to microbeads, which can be arranged within the microfluidic system. For instance, commercially-available latex microspheres with pre-defined surface chemistry can be used. The polynucleotide templates can be attached either before or after the microbeads are inducted into the microfluidic system. Attachment of template before beads are added allows a reduction in system complexity and setup time (as many templates can be attached to different aliquots of beads simultaneously). Attachment of template to beads in situ can allow easier manipulation of surface chemistry (as bead surface chemistry can be manipulated in bulk and externally to the microfluidic device). Beads should be held in place within the flow system for this technique to be effective. Methods to achieve this include, e.g., flowing the beads into orifices too small for them to flow through (where they would become "wedged in"), the creation of "microscreens" (i.e. barriers in the channel with apertures too small for beads to pass through), and insertion of the beads into hollows in the channels where they are affixed by simple Van der Waals forces.

B. Primer Extension Reaction

Once templates are immobilized to the surfaces of synthesis channels, primer extension reactions are performed (E. D. Hyman, Anal. Biochem., 174, p. 423, 1988). If part of the template sequence is known, a specific primer can be constructed and hybridized to the template. Alternatively, a linker can be ligated to the template of unknown sequence in order to allow for hybridization of a pimer. The primer can be hybridized to the template before or after immobilization of the template to the surface of the synthesis channel.

In some methods, the primer is extended by a nucleic acid polymerase in the presence of a single type of labeled nucleotide. Label is incorporated into the template/primer complex only if the labeled nucleotide added to the reaction is complementary to the nucleotide on the template adjacent the 3' end of the primer. The template is subsequently washed to remove any unincorporated label, and the presence of any incorporated label is determined. A radioactive label can be determined by counting or any other method known in the art, while fluorescent labels can be induced to fluoresce, e.g., by excitation.

In some applications of the present invention, a combination of labeled and non-labeled nucleotides are used in the analysis. Because there are multiple copies of each template molecule immobilized on the surface of the synthesis channel, a small percentage of labeled nucleotides is sufficient for detection by a detection device (see below). For example, for fluorescently labeled nucleotides, the percentage of labeled nucleotide can be less than 20%, less than 10%, less than 5%, less than 1%, less than 0.1%, less than 0.01%, or even less than 0.001% of the total labeled and unlabeled nucleotides for each type of the nucleotides.

1. Labeled Nucleotides

In some methods, at least one and usually all types of the deoxyribonucleotides (dATP, dTTP, dGTP, dCTP, dUTP/dTTP) or nucleotides (ATP, UTP, GTP, and CTP) are labeled. Various labels which are easily detected include radioactive labels, optically detectable labels, spectroscopic labels and the like. Preferably, fluorescent labels are used. The different types of nucleotides can be labeled with the same kind of labels. Alternatively, a different kind of label can be used to label each different type of nucleotide.

In some methods, fluorescent labels are used. the fluorescent label can be selected from any of a number of different moieties. The preferred moiety is a fluorescent group for which detection is quite sensitive. For example, fluorescein- or rhodamine-labeled nucleotide triphosphates are available (e.g., from NEN DuPont).

Fluorescently labeled nucleotide triphosphates can also be made by various fluorescence-labeling techniques, e.g., as described in Kambara et al. (1988) "Optimization of Parameters in a DNA Sequenator Using Fluorescence Detection," Bio/Technol. 6:816-821; Smith et al. (1985) Nucl. Acids Res, 13:2399-2412; and Smith et al. (1986) Nature 321:674-679. Fluorescent labels exhibiting particularly high coefficients of destruction can also be useful in destroying nonspecific background signals.

2. Blocking Agents

In some methods during the primer extension step, a chain elongation inhibitor can be employed in the reaction (see, e.g., Dower et al., U.S. Pat. No. 5,902,723. Chain elongation inhibitors are nucleotide analogues which either are chain terminators which prevent further addition by the polymerase of nucleotides to the 3' end of the chain by becoming incorporated into the chain themselves. In some methods, the chain elongation inhibitors are dideoxynucleotides. Where the chain elongation inhibitors are incorporated into the growing polynucleotide chain, they should be removed after incorporation of the labeled nucleotide has been detected, in order to allow the sequencing reaction to proceed using different labeled nucleotides. Some 3'→5' exonucleases, e.g., exonuclease III, are able to remove dideoxynucleotides.

Other than chain elongation inhibitors, a blocking agent or blocking group can be employed on the 3' moiety of the deoxyribose group of the labeled nucleotide to prevent non-specific incorporation. Optimally, the blocking agent should be removable under mild conditions (e.g., photosensitive, weak acid labile, or weak base labile groups), thereby allowing for further elongation of the primer strand with a next synthetic cycle. If the blocking agent also contains the fluorescent label, the dual blocking and labeling functions are achieved without the need for separate reactions for the separate moieties. For example, the labeled nucleotide can be labeled by attachment of a fluorescent dye group to the 3' moiety of the deoxyribose group, and the label is removed by cleaving the fluorescent dye from the nucleotide to generate a 3' hydroxyl group. The fluorescent dye is preferably linked to the deoxyribose by a linker arm which is easily cleaved by chemical or enzymatic means.

Examples of blocking agents include, among others, light sensitive groups such as 6-nitoveratryloxycarbonyl (NVOC), 2-nitrobenzyloxycarbonyl (NBOC), ..alpha., ..alpha.-dimethyl-dimethoxybenzyloxycarbonyl (DDZ), 5-bromo-7-nitroindolinyl, o-hydroxy-2-methyl cinnamoyl, 2-oxymethylene anthraquinone, and t-butyl oxycarbonyl (TBOC). Other blocking reagents are discussed, e.g., in U.S. Ser. No. 07/492,462; Patchornik (1970) J. Amer. Chem. Soc. 92:6333; and Amit et al. (1974) J. Org. Chem. 39:192. Nucleotides possessing various labels and blocking groups can be readily synthesized. Labeling moieties are attached at appropriate sites on the nucleotide using chemistry and conditions as described e.g., in Gait (1984) Oligonucleotide Synthesis: A Practical Approach, IRL Press, Oxford.

3. Polymerases

Depending on the template, either RNA polymerase or DNA polymerases can be used in the primer extension. For analysis of DNA templates, many DNA polymerases are available. Examples of suitable DNA polymerases include, but are not limited to, Sequenase 2.0®, T4 DNA polymerase or the Klenow fragment of DNA polymerase 1, or Vent polymerase. In some methods, polymerases which lack 3'→5' exonuclease activity can be used (e.g., T7 DNA polymerase (Amersham) or Klenow fragment of DNA polymerase I (New England Biolabs)). In some methods, when it is desired that the polymerase have proof-reading activity, polymerases lacking 3'→5' exonuclease activity are not used. In some methods, thermostable polymerases such as ThermoSequenase™ (Amersham) or Taquenase™ (ScienTech, St Louis, Mo.) are used.

The nucleotides used in the methods should be compatible with the selected polymerase. Procedures for selecting suitable nucleotide and polymerase combinations can be adapted from Ruth et al. (1981) Molecular Pharmacology 20:415-422; Kuteladze, T., et al. (1984) Nuc. Acids Res., 12:1671-1686; Chidgeavadze, Z., et al. (1985) FEBS Letters, 183:275-278.

The polymerase can be stored in a separate reservoir in the apparatus and flowed into the synthesis channels prior to each extension reaction cycle. The enzyme can also be stored together with the other reaction agents (e.g., the nucleotide triphosphates). Alternatively, the polymerase can be immobilized onto the surface of the synthesis channel along with the polynucleotide template.

4. Removal of Blocking Group and Labels

By repeating the incorporation and label detection steps until incorporation is detected, the nucleotide on the template adjacent the 3' end of the primer can be identified. Once this has been achieved, the label should be removed before repeating the process to discover the identity of the next nucleotide.

Removal of the label can be effected by removal of the labeled nucleotide using a 3'→5' exonuclease and subsequent replacement with an unlabeled nucleotide. Alternatively, the labeling group can be removed from the nucleotide. In a further alternative, where the label is a fluorescent label, it is possible to neutralize the label by bleaching it with radiation. Photobleaching can be performed according to methods, e.g., as described in Jacobson et al., "International Workshop on the Application of Fluorescence Photobleaching Techniques to Problems in Cell Biology", Federation Proceedings, 42:72-79, 1973; Okabe et al., J Cell Biol 120:1177-86, 1993; and Close et al., Radiat Res 53:349-57, 1973.

If chain terminators or 3' blocking groups have been used, these should be removed before the next cycle can take place. 3' blocking groups can be removed by chemical or enzymatic cleavage of the blocking group from the nucleotide. For example, chain terminators are removed with a 3'→5' exonuclease, e.g., exonuclease III. Once the label and terminators/blocking groups have been removed, the cycle is repeated to discover the identity of the next nucleotide.

Removal of the blocking groups can be unnecessary if the labels are removable. In this approach, the chains incorporating the blocked nucleotides are permanently terminated and no longer participate in the elongation processes. So long as these blocked nucleotides are also removed from the labeling process, a small percentage of permanent loss in each cycle can also be tolerated.

In some methods, other than labeled nucleotides, nucleotide incorporation is monitored by detection of pyrophosphate release (see, e.g., WO98/13523, WO98/28440, and Ronaghi et al., Science 281:363, 1998). For example, a pyrophosphate-detection enzyme cascade is included in the reaction mixture in order to produce a chemoluminescent signal. Also, instead of deoxynucleotides or dideoxynucleotides, nucleotide analogues are used which are capable of acting as substrates for the polymerase but incapable of acting as substrates for the pyrophosphate-detection enzyme. Pyrophosphate is released upon incorporation of a deoxynucleotide or dideoxynucleotide, which can be detected enzymatically. This method employs no wash steps, instead relying on continual addition of reagents.

C. Detection of Incorporated Signals and Scanning System

1. Optical Detection

Methods for visualizing single molecules of DNA labeled with an intercalating dye include, e.g., fluorescence microscopy as described in Houseal et al., Biophysical Journal 56:507, 1989. While usually signals from a plurality of molecules are to be detected with the sequencing methods of the present invention, fluorescence from single fluorescent dye molecules can also be detected. For example, a number of methods are available for this purpose (see, e.g., Nie et al., Science 266: 1013, 1994; Funatsu et al., Nature 374: 555, 1995; Mertz et al., Optics Letters 20: 2532, 1995; and Unger et al., Biotechniques 27:1008, 1999). Even the fluorescent spectrum and lifetime of a single molecule before it photobleaches can be measured (Macklin et al., Science 272: 255, 1996). Standard detectors such as a photomultiplier tube or avalanche photodiode can be used. Full field imaging with a two stage image intensified CCD camera can also used (Funatsu et al., supra).

The detection system for the signal or label can also depend upon the label used, which can be defined by the chemistry available. For optical signals, a combination of an optical fiber or charged couple device (CCD) can be used in the detection step. In those circumstances where the matrix is itself transparent to the radiation used, it is possible to have an incident light beam pass through the substrate with the detector located opposite the substrate from the polynucleotides.

For electromagnetic labels, various forms of spectroscopy systems can be used. Various physical orientations for the detection system are available and discussion of important design parameters is provided, e.g., in Jovin, Adv. in Biochem. Bioplyms.

Incorporated signals can be detected by scanning the synthesis channels. The synthesis channels can be scanned simultaneously or serially, depending on the scanning method used. The signals can be scanned using a CCD camera (TE/CCD512SF, Princeton Instruments, Trenton, N.J.) with suitable optics (Ploem, J. S., in Fluorescent and Luminescent Probes for Biological Activity, Mason, T. W., Ed., Academic Press, London, pp. 1-11, 1993), such as described in Yershov et al. (Proc. Natl. Acad. Sci. 93:4913, 1996), or can be imaged by TV monitoring (Khrapko et al., DNA Sequencing 1:375, 1991). For radioactive signals (e.g., $^{32}$P), a phosphorimager device can be used (Johnston et al., Johnston, R. F., et al., Electrophoresis 11:355, 1990; and Drmanac et al., Drmanac, R., et al., Electrophoresis 13:566, 1992). These methods are particularly useful to achieve simultaneous scanning of multiple probe-regions.

For fluorescence labeling, the synthesis channels can be serially scanned one by one or row by row using a fluorescence microscope apparatus, such as described in U.S. Pat. Nos. 6,094,274, 5,902,723, 5,424,186, and 5,091,652. In some methods, standard low-light level cameras, such as a SIT and image intensified CCD camera, are employed (see, Funatsu et al., Nature 374, 555, 1995). An ICCD can be preferable to a cooled CCD camera because of its better time resolution. These devices are commercially available (e.g., from Hammamatsu).

Alternatively, only the intensifier unit from Hammamatsu or DEP are used and incorporated into other less expensive or home built cameras. If necessary, the intensifier can be cooled. For example, CCD camera can be purchased from Phillips, who offer a low priced, low noise (40 electron readout noise per pixel) model. A home built camera allows greater flexibility in the choice of components and a higher performance device. The advantage of using a camera instead of an avalanche photodiode is that one can image the whole field of view. This extra spatial information allows the development of new noise reduction techniques. For example, one can use the fact that signals are expected from certain spatial locations (i.e., where the polynucleotide template is attached) in order to reject noise. In some applications, fluorescent excitation is exerted with a Q-switched frequency doubled Nd YAG laser, which has a KHz repetition rate, allowing many samples to be taken per second. For example, a wavelength of 532 nm is ideal for the excitation of rhodamine. It is a standard device that has been used in the single molecule detection scheme (Smith et al., Science 253:1122, 1992). A pulsed laser allows time resolved experiments, which are useful for rejecting extraneous noise. In some methods, excitation can be performed with a mercury lamp and signals from the incorporated nucleotides can be detected with an inexpensive CCD camera (see, e.g., Unger et al., Biotechniques 27:1008, 1999.

The scanning system should be able to reproducibly scan the synthesis channels in the apparatuses. Where appropriate, e.g., for a two dimensional substrate where the synthesis channels are localized to positions thereon, the scanning system should positionally define the synthesis channels attached thereon to a reproducible coordinate system. It is important that the positional identification of synthesis channels be repeatable in successive scan steps.

Various scanning systems can be employed in the apparatuses of the present invention. For example, electrooptical scanning devices described in, e.g., U.S. Pat. No. 5,143,854, are suitable for use with the apparatuses of the present invention. The system could exhibit many of the features of photographic scanners, digitizers or even compact disk reading devices. For example, a model no. PM500-A1 x-y translation table manufactured by Newport Corporation can be attached to a detector unit. The x-y translation table is connected to and controlled by an appropriately programmed digital computer such as an IBM PC/AT or AT compatible computer. The detection system can be a model no. R943-02 photomultiplier tube manufactured by Hamamatsu, attached to a preamplifier, e.g., a model no. SR440 manufactured by Stanford Research Systems, and to a photon counter, e.g., an SR430 manufactured by Stanford Research System, or a multichannel detection device. Although a digital signal can usually be preferred, there can be circumstances where analog signals would be advantageous.

The stability and reproducibility of the positional localization in scanning determine, to a large extent, the resolution for separating closely positioned polynucleotide clusters on a 2 dimensional substrate. Since the successive monitoring at a given position depends upon the ability to map the results of a reaction cycle to its effect on a positionally mapped cluster of polynucleotides, high resolution scanning is preferred. As the resolution increases, the upper limit to the number of possible polynucleotides which can be sequenced on a single matrix also increases. Crude scanning systems can resolve only on the order of 1000 µm, refined scanning systems can resolve on the order of 100 µm, more refined systems can resolve on the order of about 10 µm, and with optical magnification systems a resolution on the order of 1.0 µm is available. The limitations on the resolution can be diffraction limited and advantages can arise from using shorter wavelength radiation for fluorescent scanning steps. However, with increased resolution, the time required to fully scan a matrix can increased and a compromise between speed and resolution can be selected. Parallel detection devices which provide high resolution with shorter scan times are applicable where multiple detectors are moved in parallel.

In some applications, resolution often is not so important and sensitivity is emphasized. However, the reliability of a signal can be pre-selected by counting photons and continuing to count for a longer period at positions where intensity of signal is lower.

Although this decreases scan speed, it can increase reliability of the signal determination.

Various signal detection and processing algorithms can be incorporated into the detection system. In some methods, the distribution of signal intensities of pixels across the region of signal are evaluated to determine whether the distribution of intensities corresponds to a time positive signal.

2. Non-Optical Detection

Other than fluorescently labeled nucleotides and optical detection devices, other methods of detecting nucleotide incorporation are also contemplated in the present invention, including the use of mass spectrometry to analyze the reaction products, the use of radiolabeled nucleotides, and detection of reaction products with "wired enzymes".

In some methods, mass spectrometry is employed to detect nucleotide incorporation in the primer extension reaction. A primer extension reaction consumes a nucleotide triphosphate, adds a single base to the primer/template duplex, and produces pyrophosphate as a by-product. Mass spectrometry can be used to detect pyrophosphate in the wash stream after a nucleotide has been incubated with the template and polymerase. The absence of pyrophosphate indicates that the nucleotide was not incorporated, whereas the presence of pyrophosphate indicates incorporation. Detection based on pyrophosphate release have been described, e.g., in WO98/13523, WO98/28440, and Ronaghi et al., Science 281:363, 1998.

In some methods, radiolabeled nucleotides are used. Nucleotides can be radiolabeled either in the sugar, the base, or the triphosphate group. To detect radioactivity, small radioactivity sensor can be incorporated in the substrate on which the microfluidic chip is mounted. A CCD pixel, for instance, serves as a good detector for some radioactive decay processes. Radiolabeling of the sugar or base produces an additive signal: each incorporation increases the amount of radiolabel in the primer-template duplex. If the nucleotide is labeled in the portion that is released as pyrophosphate (e.g., dNTP with $\alpha$- or $\gamma$-$^{32}$P), the radioactive pyrophosphate can be detected in the wash stream. This radioactivity level is not additive, but rather binary for each attempted nucleotide addition, so subsequent addition poses no read length limit. Due to the small reagent consumption and contained nature of microfluidics, the total radioactivity used in such a system is relatively minimal, and containment is relatively simple.

In some methods, non-optical detection of pyrophosphate release makes use of "wired redox enzymes" as described, e.g., in Heller et al., Analytical Chemistry 66:2451-2457, 1994; and Ohara et al., Analytical Chemistry 65:3512-3517, 1993. Briefly, enzymes are covalently linked to a hydrogel matrix containing redox active groups capable of transporting charge. The analyte to be detected is either acted on directly by a redox enzyme (either releasing or consuming electrons) or consumed as a reagent in an enzymatic cascade that produces a substrate that is reduced or oxidized by a redox enzyme. The production or consumption of electrons is detected at a metal electrode in contact with the hydrogel. For the detection of pyrophosphate, an enzymatic cascade using pyrophosphatase, maltose phosphorylase, and glucose oxidase can be employed. Pyrophosphatase converts pyrophosphate into phosphate; maltose phosphorylase converts maltose (in the presence of phosphate) to glucose 1-phosphate and glucose. Then, glucose oxidase converts the glucose to gluconolactone and $H_2O_2$; this final reaction is the redox step which gives rise to a detectable current at the electrode. Glucose sensors based on this principle are well known in the art, and enzymatic cascades as described here have been demonstrated previously. Other enzymatic cascades besides the specific example given here are also contemplated the present invention. This type of detection scheme allows direct electrical readout of nucleotide incorporation at each reaction chamber, allowing easy parallelization.

3. Fluorescent Photobleaching Sequencing

In some methods, polynucleotide sequences are analyzed with a fluorescent photobleaching method. In this methods, fluorescently labeled nucleotides are used in the primer extension. Signals from the incorporated nucleotides are removed by photobleaching before next extension cycle starts.

The polynucleotide templates can be prepared as described above (e.g., cloning in single-stranded M13 plasmid). Biotinylated templates are attached to surface of the synthesis channel that has been pretreated with the PEM technique as discussed above. After the primed, single stranded DNA is immobilized to the synthesis channel in the flow cell. A polymerase and one nucleotide triphosphate, e.g. dATP, are flowed into the flow cell. A high fidelity polymerase with no exonuclease proofreading ability is preferred. In some methods, only a fraction (e.g., less than 10%, 5%, 1%, 0.1%, 0.01%, or 0.001%) of each type of the nucleotide triphosphates is fluorescently labeled (e.g., rhodamine-labeled nucleotide triphosphates from NEN DuPont). For example, if the first base of DNA sequence following the primer is T, then the polymerase incorporates the dATP's and some fraction of the DNA molecules become fluorescently labeled. If the first base is anything else, no fluorescent molecules become incorporated. The reagents are then flowed out of the flow cell, and the fluorescence of the DNA is measured. If no fluorescence is detected, the procedure is repeated with one of the other nucleotide triphosphates. If fluorescence is detected, the identity of the first base in the sequence has been determined. The fluorescence signal is photobleached and extinguished before the procedure is then repeated for the next base in the template sequence.

The fluorescence can be excited with, e.g., a Q-switched frequency doubled Nd YAG laser (Smith et al., Science 253: 1122, 1992). This is a standard device used in the single molecule detection scheme that measures the fluorescent spectrum and lifetime of a single molecule before it photobleached. It has a kHz repetition rate, allowing many samples to be taken per second. The wavelength can be e.g., 532 nm that is ideal for the excitation of rhodamine. A pulsed laser allows time resolved experiments and is useful for rejecting extraneous noise.

Detection of the incorporated label can be performed with a standard low-light level cameras, such as a SIT or a image intensified CCD camera (Funatsu et al, supra). An Intensified CCD (ICCD) camera is preferable to a cooled CCD camera because of its better time resolution. These devices are available from, e.g., Hammamatsu. However, because these cameras are extremely expensive, a detection device can be made by building just the intensifier unit from Hammamatsu into a CCD camera. Optionally, the intensifier can be cooled. The CCD camera is available from Phillips, e.g., a low priced, low noise model (40 electron readout noise per pixel). A customarily built camera allows greater flexibility in the choice of components and a higher performance device. The advantage of using a camera instead of an avalanche photodiode is that the whole field of view can be imaged. This extra spatial information allows the development of new noise reduction techniques. For example, the fact that signals are expected from certain spatial locations (i.e. where the DNA is attached) can be used to reject noise.

D. Other Considerations

A combination of factors affect the read length and throughput of the sequencing analysis according to the present invention. First, all of the unincorporated labeled nucleotides should be removed from the synthesis channel or reaction chamber after each cycle. Since only relatively small number of incorporated dye molecules are to be detected, the reagent exchange should be leave substantially fewer unincorporated labeled nucleotides than the number of nucleotides to be detected. Second, the rate of reagent exchange is limited by fluid mechanic considerations. Turbulent flow should be avoided in order to preserve effective reagent exchange, and the fluid flow shear forces should be small enough in order to not break the DNA or dislocate the enzyme. Third, the kinetics of nucleotide incorporation and enzyme-DNA complex formation should be considered.

The present invention teaches how to determine acceptable flow rate of fluids in the apparatuses. According to the invention, flow rate in the apparatuses with microfabricated flow channels having a depth of 100 μm is typically 0.1-1 cm/sec.

For microfabricated flow channels with a depth of 10 μm, the flow rate is usually in the range of 1-10 cm/sec. Fluid flow in the apparatuses remains laminar as long as the Reynolds number $R=\rho \upsilon \iota/\eta << 1$, where $\rho$ is the density of the fluid, $\upsilon$ is the velocity, $\iota$ is the dimension of the chamber, and $\eta$ is the viscosity (see, e.g., Landau et al., Fluid Mechanics, Pergamon Press, New York, 1989). The limiting velocity is in the order of 1 cm/sec for a 100 μm channel depth. For microchannels with a depth of 10 μm, the limit is 10 cm/sec.

The ultimate limit on the rate at which fluid can be exchanged is determined by the effect of drag and shear flows on the polynucleotide template and the polymerase. The velocity profile of constrained flow is parabolic ($v(\tau)-V_{ave}(1-(\tau/R)_2)$), causing a shear force. Single molecule experiments with double stranded DNA have shown that one can apply forces of up to F=50 pN without breaking or causing irreversible damage to DNA (see, e.g., Smith et al., Science 271: 795, 1996; and Cluzel et al., Science 271: 792, 1996), and a similar order of magnitude is expected for single stranded DNA. The drag coefficient of DNA $\alpha=6\pi R_5$ can be estimated from the radius of gyration $R_5=0.3$ μm. Then the maximum fluid velocity allowed is determined by solving the equation:

$$v_{max}(R-R_g)=F/\alpha$$

The maximum average velocity before shearing of DNA becomes a problem is 140 cm/sec.

Another consideration is to prevent the polymerase from falling off the template or becoming damaged. With RNA polymerase, it has been shown that the stalling force for RNA polymerase, at which it might receive irreversible damage, is 14 pN (Yin et al., Science 270:1653, 1995). Since one the drag coefficient of a DNA polymerase can be estimated from its size, a similar calculation as for the DNA shear leads to a maximum velocity of 500 cm/sec.

The time to remove all of the free nucleotides can be calculated by including the effects of diffusion into hydrodynamic calculation of the fluid flow. There are a great variety of products available, including electronic switching valves with very small dead volumes. For example, a six port valve from Upchurch with electric motor from Thar Designs has a dead volume of 2 μl and switching time of 166 msec. Combined with 0.0025" I.D. tubing and the estimated 1 μl capacity of the microfabricated flow cell, 4 μl of material should be exchanged for each step in the process. A syringe or peristaltic pump can give very high flow rates, the limiting factor is low Reynolds number. The inverse rate constant to get rid of all of the nucleotides is $$\tau=(LR/V_{ave})^{2/3}(D)^{-1/3}$$

where L is the linear dimension of the device and D is the diffusion constant of the nucleotides. Plugging in approximate numbers gives a time of $\tau=15$ sec. To reduce the nucleotide concentration from in the order of millimolar to 1 labeled nucleotide per detection region, which is a reduction of approximately $10^{-7}$. The amount of time to completely flush the device is $\ln(10^{-7})\tau=4$ minutes.

For apparatuses with microfabriated flow channel depth of 10 μm and microfabricated valves incorporated on chip, the dead volume is reduced and throughput increased. The valves can provide an essentially zero dead volume and 10 msec switching time. This and the reduced dimensions of the device leads to a drastic increase of throughput: the time to flush the reagents (e.g., nucleotides) from the system is reduced to 0.8 sec. The overall throughput is approximately 1 base per second. Table 1 summarizes the various factors affecting throughput of apparatuses with microfabricated flow channels having a depth of 100 μm or 10 μm.

TABLE I

Parameters affecting throughput of the sequencing apparatuses

|  | I | II |
| --- | --- | --- |
| Channel depth (μm) | 100 | 10 |
| Dead Volume (μl) | 4 | $10^{-3}$ |
| Turbulence vel. (cm/sec) | 1 | 10 |
| DNA Shear (cm/sec) | 140 | 14 |
| Polymerase stall (cm/sec) | 1000 | 100 |
| Reagent exchange (sec) | 240 | 0.8 |

Note that in apparatus I, the limiting factor is the fluid velocity that causes turbulent flow. In apparatuses II, shear forces on the DNA also becoming limiting. The reagent exchange time is expected to improve by a factor of 100 in apparatus II.

The DNA polymerases can fall off of the DNA. If enzyme is replenished, it takes time for the enzyme to find and bind to a free DNA site. This could affect throughput of the apparatuses. The attrition rate of the polymerase can be determined according to methods described in the art. For example, using the kinetics of the T4 DNA polymerase as nominal values (Taylor et al., J. Phys. D. Appl. Phys. 24:1443, 1991), an on-rate of 11 $\mu M^{-1}$ $sec^{-1}$ was obtained. Hence a 1 μM concentration of enzyme gives an on rate of 11 $sec^{-1}$, and after 1 second, 99.3% of the DNA have polymerase bound. In the absence of nucleotides (for example, during fluorescence measurement) the polymerase falls off of the DNA with a time constant of 0.2 $sec^{-1}$ (Yin et al., Science 270:1653, 1995). In other words, after 5 seconds without nucleotides, this can become a source of attrition. It can be compensated for by the addition of fresh polymerase with every sequencing cycle of the device.

For the high throughput device (e.g., apparatus II in Table I), the reagent exchange is fast enough that polymerase falling off has no significant effect on the throughput. Also, the rate of incorporation of nucleotides by the polymerase is typically about 300 bases per second. This is not a rate limiting factor for the device throughput.

Read length of the sequencing analysis can be affected by various factors. However, photobleaching is unlikely to cause any chemical changes to the polynucleotide template that prevent the attachment of the next base. During the photobleaching, the dye molecule is held off from the DNA on a linker arm, and it gives off so few photons that the interaction cross section is negligible. Any attrition of the labeled nucleotides also does not present any significant problem. The statistics of the photobleaching scheme are robust enough to allow sequencing to continue in spite of any attrition of the labeled nucleotides. For example, if 0.1% of the bases are labeled, then after 3000 bases the attrition is 95% if incorporation of a labeled nucleotide terminates strand extension completely. In other word, if one starts with $10^5$ molecules, then on the first base one expects to get a fluorescent signal from 100 dye molecules. By the 3000th base, the signal is reduced to only 5 dye molecules. This is still detectable, since the lower limit of detection is one dye molecule.

It should also be noted that the attrition are discussed above is an extreme scenario because there is little reason to expect total attrition for each incorporated base. Attrition is more likely to occur when the polymerase incorporates two successive labeled nucleotides. If 1% of the bases are labeled, the chance of incorporating two labeled nucleotides next to each other is $1\%^2=0.01\%$. Then the attrition rate after 3000 bases is 25%. In other words, the signal only decreases by 25% by the 3000th base. Thus, attrition does not cause a problem in this sequencing scheme.

Another factor that can affect read length is misincorporation. If the DNA polymerase is starved for the proper nucleotide, it can incorporate the wrong nucleotide. Misincorporation efficiencies have been measured to be three to five orders of magnitude below the efficiency for proper nucleotide incorporation (Echols et al., Ann. Rev. Biochem 60:477, 1991). Misincorporation can be minimized by only exposing the DNA polymerase-DNA complexes to nucleotides for as much time as is needed to incorporate the proper nucleotide. For a high fidelity DNA polymerase, misincorporation happens with a frequency of about $10^{-4}$. If dephasing due to misincorporation is treated as total attrition, the attrition is only 25% after 3 kb, i.e., the signal is reduced to 75% of its original. Thus, misincorporation does not hinder a 3 kb or perhaps longer read length.

G. EXAMPLES

Certain embodiments of the invention are described in the following non-limiting examples, as well as in Kartalov et al., Nucl. Acids Res. 32:2873-79, which is incorporated by reference herein.

EXAMPLE 1

PDMS-DAPEG-PEM Surface Chemistry

This set of experiments demonstrates a non-UV-based, specific and tunable anchoring of DNA to poly(dimethylsiloxane) (PDMS) in which the DNA remains sterically available for enzymatic biochemical reactions and fluorescence background from non-specific binding is suppressed through polyelectrolyte multilayer (PEM) surface chemistry. In general terms, these experiments utilize a microfluidic chip having a PDMS layer as a floor for the flow channels, and PEM linked to the PDMS with diacrylated poly(ethylene glycol) (DAPEG).

Microfluidic Chip Fabrication

PDMS microfluidic chips with integrated micromechanical valves were built using soft lithography as described herein with the following modifications. Silicon wafers were exposed to hexamethyldisilazane (HMDS) (ShinEtsuMicroSi, Phoenix, Ariz.) vapors for 3 minutes. Photoresist 5740 (MicroChem Corp., Newton, Mass.) was spun at 2500 rpm for 60 seconds on a Model WS-400A-6NPP/LITE spinner from Laurel Technologies Corp. The wafers were baked at 105° C. for 90 seconds on a hotplate. UV exposure through black-and-white transparency masks was done at 180 mW/cm² for 25 seconds on a mask aligner (Karl Suss America Inc., Waterbury, Vt.). The molds were then developed for 3 minutes in a solution of 5:1=deionized water:2401 MicroChem developer. The flow layer molds were baked at 100° C. for 30 minutes on a hotplate to melt the Photoresist 5740 and round the flow channels. The molds were characterized on Alpha-Step 500 (KLA-Tencor, Mountain View, Calif.). The channel height was between 9 and 11 μm, while main flow channel width was between 95 and 105 μm. The control channel profile was oblong, while flow channel profile was parabolic. Except for the height measurements and the flow channel rounding, the mold fabrication was conducted in a class-10,000 clean room.

The molds were exposed to tetramethylchlorosilane (TMCS) (Aldrich) vapors for 3 minutes. PDMS (Sylgard 184; Dow Corning, K. R., Anderson, Santa Clara, Calif.) in 5:1 and 20:1 ratios were mixed and degassed using HM-501 hybrid mixer and cups from Keyence Corp. (Long Beach, Calif.). Then 35 grams of the 5:1 was poured onto the control mold in a plastic Petri dish wrapped with aluminum foil. Five grams of the 20:1 was spun over the flow mold at 2500 rpm for 60 seconds on Spincoater P6700 (Specialty Coating Systems, Indianapolis, Ind.). Both were baked in an 80° C. oven for 30 minutes. The control layer was taken off its mold and cut into respective chip pieces. Control line ports were punched using a 20-gauge luer-stub adapter (Beckton-Dickinson, Franklin Lakes, N.J.). Control layer pieces were washed with ethanol, blown dry and aligned on top of the flow layer under a stereoscope. The result was baked in an 80° C. oven for 1 hour. Chip pieces were then cut out and peeled off the flow layer mold. Flow line ports were punched with the same 20-gauge luer-stub adapter. Meanwhile, 5:1 Sylgard was spun at 5000 rpm for 60 seconds over RCA-cleaned 22 mm #1 coverslips. The coverslips were then baked in an 80° C. oven for 30 minutes. Chip pieces were washed in ethanol and blown dry before binding to the PDMS layer on the coverslips. The assembled chips underwent final bake in an 80° C. oven for 2 hours.

Surface Chemistry Preparation

The flow channels of the PDMS chip were filled with a mixture of DAPEG (diacrylated poly(ethylene glycol) SR610, Sartomer, Exton, Pa.) and the Pt catalyst (hydrogen hexachloroplatinate, Aldrich) at the volumetric ratio of 200:1=DAPEG:catalyst. In the presence of the Pt catalysts, the PDMS polymerized as SiH groups reacted with vinyl groups, leaving unreacted SiH groups on the surface. The chip was then baked in an oven at 80° C. for 30 minutes. The DAPEG mixture was flushed out of the microchannels with high purity water. Alternating layers of polyethyleneimine (PEI) (Sigma Corp., P-3143) and polyacrylic acid (PAcr) (Aldrich) were built using 5 minute feeds of 20 mg/ml solutions at pH 8. Next, the surface was biotinylated using a biotinylation kit from Pierce Biotechnology, Inc. (Rockford, Ill.). This was followed by deposition of Streptavidin Plus (ProZyme, Inc., San Leandro, Calif.) at 1 mg/ml in Trisb (Tris 10 mM (NaCl 10 mM) pH 8) and biotinylated DNA at 7 μM in TrisMg (Tris 10 mM (NaCl 10 mM, MgCl₂ 100 mM) pH 8).

Figure 29A:
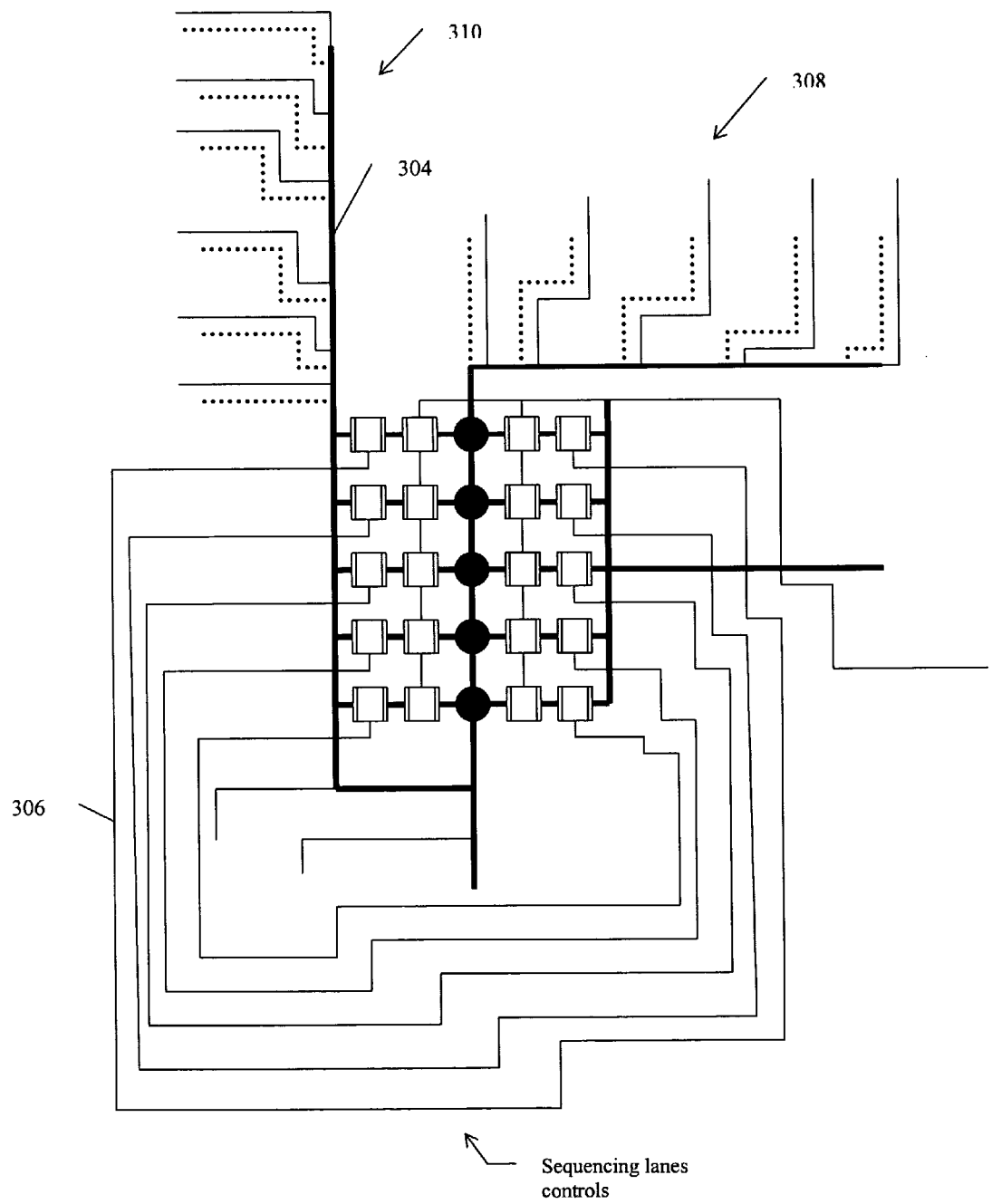
FIG. 29A is a schematic representation of a microchannel system of an embodiment of a microchip according to the invention.
Figure 29B:
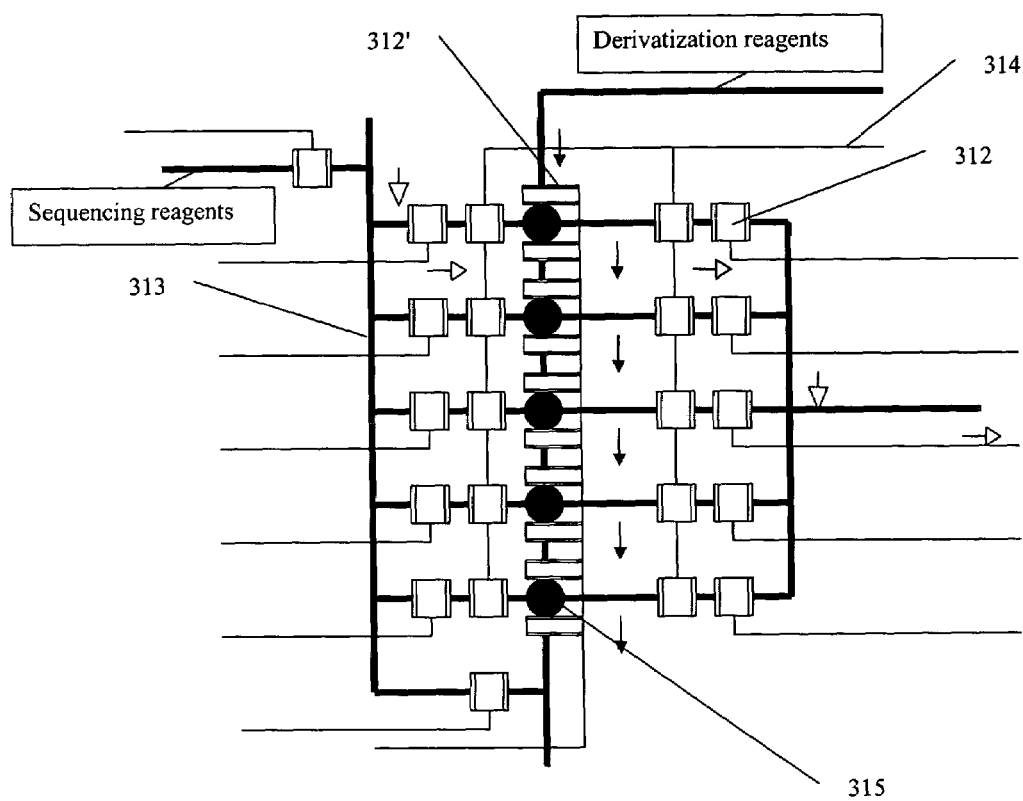
FIG. 29B is a schematic representation of a valve system corresponding to the microchannel system of FIG. 29A.

An embodiment of a microfluidic chip fabricated according to this Example is shown schematically in FIGS. 29A and 29B. More specifically, FIG. 29A shows microchannels defining a flow layer (304) and a control layer (306), as well as a derivatization tree (308) and a sequencing tree (310). FIG. 29B shows a valve system corresponding to the microchannel system of FIG. 29A. The valves (312, 312') are formed where wide control segments (313) cross over flow segments (314) and control the flow of reagents into and out of the sequencing chambers. The derivatization reagents build up the surface chemistry in all sequencing chambers (315) at the same time. This parallelism is used in applications where a large number of chambers mustundergo multi-step in-situ derivatizations. The sequencing reagents, such as nucleotides and polymerase, are fed to individually addressable sequencing chambers. In FIG. 29B, open arrows indicate the flow of sequencing reagents during operation and closed arrows indicate the flow of derivatization reagents during operation. As shown in FIGS. 29A and 29B, five separate sequencing experiments can be run in the same device after a single parallel chemistry-build up procedure.

Set-up and Detection System

In the following set of experiments, the microfluidic chip was housed in an aluminum holder, which was itself placed in a machined attachment to the translation stage of an inverted Olympus IX50 microscope. 23-Gauge steel tubes from New England Small Tube Corp. (Litchfield, N.H. 03052) were plugged into the control channel ports of the chip. The other ends of the tubes were connected through tygon tubing (Cole-Parmer, Vernon Hills, Ill.) to Lee-valve arrays (Fluidigm Corp., South San Francisco, Calif.) operated by LabView software on a PC computer. The same types of steel tubes and tygon plumbing were used to supply reagents to the flow channel ports of the chip.

The microscope was equipped with a mercury lamp (HBO 103 W/2 Osram), an Olympus Plan 10× objective (NA 0.25), an Olympus PlanApo 60× objective (NA 1.4) and a cooled CCD camera (SBIG ST-71, Santa Barbara Instrument Group). Fluorescence detection was conducted using the following filter sets: Alexa Fluor 555 (ex D470/40, 500 DCLP, em D535/50), TAMRA, Lissamine and Cy3 (ex D540/25, dichroic 565 DCLP, em D605/55), both from Chroma Technology Corp., Brattleboro, Vt.

Background Shielding

To demonstrate the background shielding effect of the PDMS-DAPEG-PEM surface chemistry, negatively terminated PEM was built on top of DAPEG-treated microchannel surfaces in a PDMS chip as described above. Next, 1 μM dUTP-Cy3 (Amersham BioSciences, Piscataway, N.J.) in Trisb was fed through the microchannel for a few minutes. After flushing with Trisb, pictures were taken and the average counts per pixel in the microchannel were obtained. An additional layer of PEI was built up to make the surface positively charged. Then, the dUTP-Cy3 feed, flushing and detection were repeated. Since the tagged nucleotide is negatively charged, positively terminated surfaces attached 267 times more nucleotide than their negatively terminated counterparts, while control experiments showed PEM would not assemble onto PDMS in the absence of DAPEG.

Further experiments demonstrated that increasing the number of PEM layers increases the surface charge density, which improves the background shielding. Four to twelve alternating layers were used, showing inversely-related decrease in non-specific attachment.

Biotinylation Demonstration

To test biotinylation, the chambers of the same device were biotinylated over varying times. The DAPEG-PEM surface chemistry was built with eight PEM layers in a PDMS microfluidic chip as described above. Then, a biotinylation mixture was fed at 5 mM for 1, 2, 4, 8 and 16 min into lanes 1 through to 5, respectively, followed in each case by a 2 minute flushing of MES 10 mM buffer. Next, pictures of all chambers were taken as background signals before the fluorophore feed, using a rhodamine fluorescence filter set. Streptavidin Alexa Fluor 555 from Molecular Probes was fed at 1 mg/ml in Trisb for 2.5 minutes from the derivatization tree into all chambers simultaneously by keeping the derivatization valve array closed. All unattached streptavidin was washed away with Tris buffer and pictures were taken again with the same filter set. The net signal was extracted and converted into streptavidin surface density using a simple bulk calibration by volume fluorescence signal from a known probe concentration. The same calibration method was used henceforth.

Tagged streptavidin saturated the biotin surface sites, providing a measurement of the biotin density. A linear dependence with time was observed, mapping the biotinylation progress. The DNA surface density in the PDMS microchannel is tunable using this linear relationship.

Surface Chemistry Stability

In the following experiments, DNA1 is an 89mer biotinylated DNA template (Biotin-5'-tcatcag tcatcag tcatcag tcatcag tcatcag tcatcag tcatcag tcatcag tcatcag tcatcag tcatcACACG-GAGGTTCTA-3'SEQ ID NO: 1) annealed to a 14mer primer tagged with the Cy3 fluorescent dye (Cy3-5'-TAGAACCTC-CGTGT-3'SEQ ID NO: 2). DNA2 is a 99mer biotinylated DNA template (biotin-5'-tttgcttcttattc tttgcttcttattc tttgcttct-tattc tttgcttcttattc tttgcttcttattc tttgcttcttattc ttacacggaggttcta SEQ ID NO: 3) annealed to the same type of primer. All DNA was from Operon Co., Alameda, CA. The sequencing feeds contained: A (10 μM dATP-Lis, 2 μM dATP, polymerase), C (10 μM ddCTP-TAMRA, 0.2 μM dCTP, polymerase), G (10 μM ddGTP-TAMRA, 3.3 μM dGTP, polymerase), U (8 μM ddUTP-TAMRA, 28 nM dTTP, polymerase), all in 1× Sequenase reaction buffer with 15mM DTT. All tagged nucleotides were from PerkinElmer (Boston, MA). All standard nucleotides were from Boehringer Mannheim (Germany). In all cases, the polymerase used was Sequenase Version 2.0 DNA Polymerase from USB Corp. (Cleveland, OH).

To test surface chemistry stability with continuous flow, DNA1 was anchored in a device of the same layout as described above, using 16 PEM layers. Then Trisb was continuously flushed through one of the sequencing chambers, while data was simultaneously taken every 5 minutes. The surface density of emitting fluorophores versus real time of continuous flushing was observed and compared with the expected signal based on photobleaching experiments conducted without flushing. The measured signal is consistent with the prediction, so any loss of signal is attributable to bleaching of the Cy3 tag on the DNA rather than loss of DNA off the surface due to anchorage failure. Hence, the surface chemistry was stable over at least 1.5 hours of continuous flushing.

To test surface chemistry stability over time, we anchored DNA2 in a device of the same layout as described above, using 12 PEM layers. Next, from time to time, Trisb was flushed for 1 minute through all chambers simultaneously and then images of them were taken using the optical system described above. The emitting fluorophores surface densities from different chambers were plotted, which showed a consistency throughout the device, demonstrating the uniformity of conditions in the array, as well as the reproducibility of the results. Further, the signal was observed to be consistent with the bleaching prediction. Thus, the falloff across exposures was not due to loss of material off the surface but due to fluorescence bleaching. Finally, the real-time data showed the anchorage was stable over at least 14 hours at room temperature.

Stability of Sequencing Reagents

To test sequencing reagents stability over time, DNA1 was anchored in a device of the same layout as described above, using 14 PEM layers. After fluorescence detection confirmed the successful attachment of DNA in one of the microchambers, the Cy3 tags there were bleached. Next, ddGTP-TAMRA (100 μM in 1× Sequenase reaction buffer with 5 mM DTT) was fed into that chamber only, followed by a Trisb flush and fluorescence detection. Then, another solution containing 0.5 U/μl polymerase, but otherwise identical to the first solution, was fed into the same chamber, followed by a Trisb flush and fluorescence detection. Later, the same procedure was repeated with the next chamber, and so on. In each case, the polymerase successfully extended the tagged nucleotide and non-specific attachment was deminimus. As this experiment was done with a single load of reagents, the time relationship of the results across different chambers showed that the polymerase and nucleotide remained active over at least 2 hours at room temperature with no visible loss in activity.

Taken together, these experiments showed that the device and reagents are stable and capable of performing nucleotide incorporation over many hours.

Sequencing Demonstration

In this experiment, DNA1 was anchored in a device prepared as described above, using 16 PEM layers. After fluorescence detection confirmed the successful attachment of DNA, the Cy3 tags in one of the chambers were bleached. Next, a feed containing polymerase, a nucleotide, and its tagged analog, was followed by a Trisb flush and fluorescence detection. Because the tag (in this example, the dye molecules) attached to the nucleotides could hinder the polymerase activity due to steric effects, the feeds contained a mixture of a nucleotide and its tagged analog instead of the tagged analog alone. Under suitably chosen feed concentrations, only a fraction of the DNA population would extend with tagged nucleotides, while most of the DNA would build up with a standard nucleotide and thus would remain available for further extension without steric hindrance. Hence, the readout could proceed to further bases at the expense of a small portion of the DNA population per successful incorporation.

Figure 30:
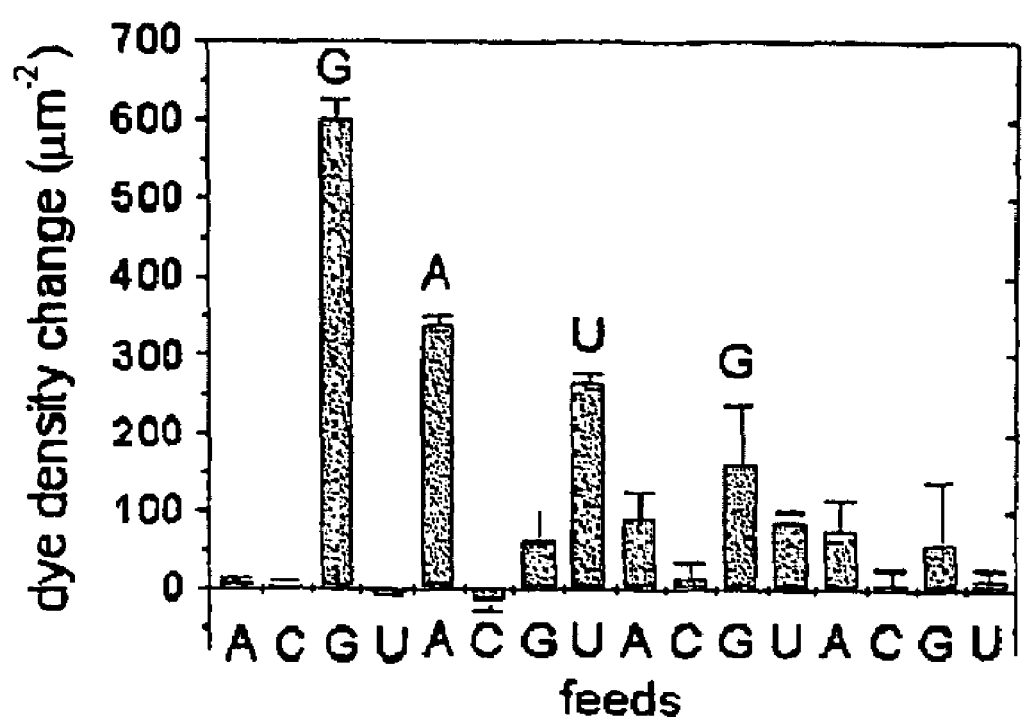
FIG. 30 shows the results from the sequencing reaction described in Example 1.

The process was iterated with different feeds in the same chamber, to collect the sequencing data. The net increase in the fluorescent signal after each feed was converted into a corresponding change in fluorophore surface density based on individual reagent calibrations. Next, the same experiment with the same sequence of feeds was repeated in another chamber of the same device, except for withholding the polymerase in all feeds. The similarly extracted data showed the level of non-specific attachment and was subtracted from the previous data to produce the final results for this experiment (FIG. 30). The measured sequence, GAUG, exactly corresponds to the beginning of the known template sequence of CTACTG, demonstrating successful sequencing of 4 consecutive base pairs in a single microfluidic chamber. The plumbing and surface chemistry described in this Example are general and can serve as the basis platform for other sequencing schemes, such as, for example, pyrosequencing.

EXAMPLE 2

Multiplexor Method

Figure 31:
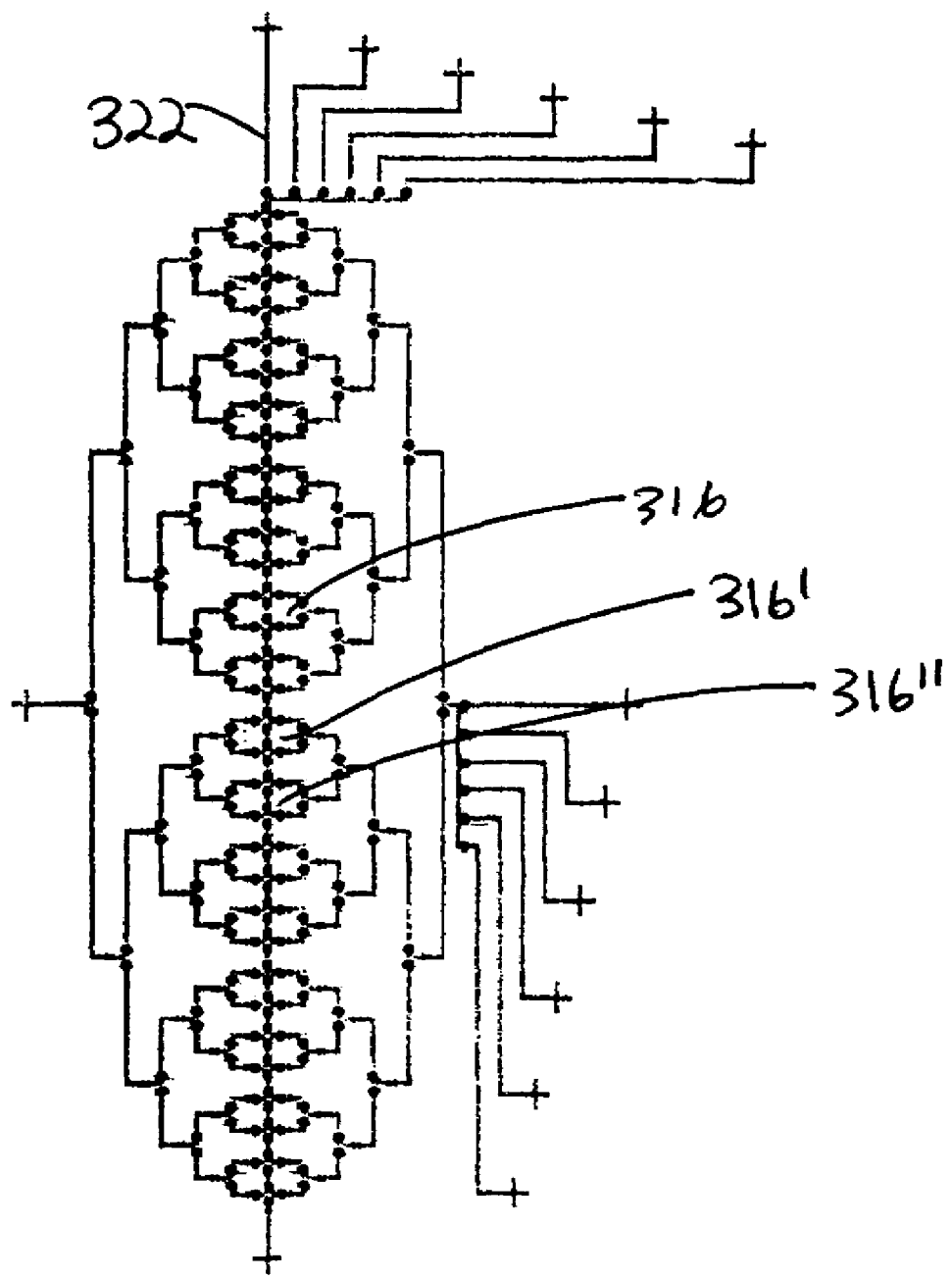
FIG. 31 is a schematic representation of a multiplexor embodiment of the invention.

According to one aspect of the invention, the number of chambers can be increased to increase the total read length by the same factor. FIG. 31 shows the layout of a multiplexor device comprising 16 chambers (316, 316', 316"). During the interrogation step, sequencing is conducted through the multiplexor in a single chamber as described above. Once a base is determined, the primers in all chambers are built up to that base by feeding the conjugate standard nucleotides and polymerase down the main channel (322). Alternating between interrogation and buildup produces total read length equal to number of chambers times the read length per single chamber. In addition, the independence of buildup and interrogation feeds means that different polymerases can be used for each feed (for example, more promiscuous and less-sterically-sensitive ones for interrogation, and stricter ones for buildup).

In another embodiment, the read length can be doubled in an array of the same size by performing two sequencing runs instead of one of the same duration. Interrogations are done with only two types of nucleotides. Positive incorporations are treated as before, but two consecutive negative results are followed by buildup of a mix of standard nucleotides of the other two types. This identifies gaps in the read sequence, which are filled by repeating the same process with opposite choice of nucleotide.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein All publications, figures, patents and patent applications cited herein are hereby expressly incorporated by reference for all purposes to the same extent as if each was so individually denoted.

What is claimed is:

1. A surface for nucleic acid sequencing, said surface comprising a plurality of chemical layers including a poly(dimethylsiloxane) layer, a poly(ethylene glycol) layer, a polyelectrolyte multilayer comprising a tunable negatively charged final layer, a nucleic acid linkage layer and a nucleic acid layer,
   wherein said poly(ethylene glycol) layer is positioned between said poly(dimethylsiloxane) layer and said polyelectrolyte multilayer, and
   wherein said nucleic acid linkage layer attaches said nucleic acid layer to said polyelectrolyte multilayer.

2. The surface of claim 1 wherein said nucleic acid layer comprises a plurality of polynucleotides and wherein each polynucleotide is individually optically resolvable.

3. The surface of claim 2 wherein said nucleic acid linkage layer comprises biotin-streptavidin or digoxygenin-anti-digoxygenin.

4. The surface of claim 1 wherein said poly(ethylene glycol) is diacrylated poly(ethylene glycol).

* * * * *

UNITED STATES PATENT AND TRADEMARK OFFICE
CERTIFICATE OF CORRECTION

| | | |
|---|---|---|
| PATENT NO. | : 7,501,245 B2 | Page 1 of 1 |
| APPLICATION NO. | : 11/002479 | |
| DATED | : March 10, 2009 | |
| INVENTOR(S) | : Stephen Quake and Emil P. Kartalov | |

It is certified that error appears in the above-identified patent and that said Letters Patent is hereby corrected as shown below:

On the Title Page
The assignee was incorrectly listed as Helicos BioScience Corp. Please remove Helicos BioScience Corp. as the assignee on this patent. Please insert the following assignee information:

Item (73)
--California Institute of Technology
1200 E. California Boulevard
MS 201-85
Pasadena, California 91125--

Signed and Sealed this

Fourth Day of May, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 89
<212> TYPE: DNA
<213> ORGANISM: Artificial Sequence
<220> FEATURE:
<223> OTHER INFORMATION: Description of Artificial Sequence: Synthetic
      DNA template

<400> SEQUENCE: 1
tcatcagtca tcagtcatca gtcatcagtc atcagtcatc agtcatcagt catcagtcat        60
cagtcatcag tcatcacacg gaggttcta                                          89

<210> SEQ ID NO 2
<211> LENGTH: 14
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
tagaacctcc gtgt                                                        14

<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Synthetic
      DNA template

<400> SEQUENCE: 3
tttgcttctt attctttgct tcttattctt tgcttcttat tctttgcttc ttattctttg     60
cttcttattc tttgcttctt attcttacac ggaggttcta                          100
```